(12) United States Patent
Minassian et al.

(10) Patent No.: US 7,670,773 B2
(45) Date of Patent: Mar. 2, 2010

(54) MECP2E1 GENE

(75) Inventors: Berge A. Minassian, Toronto (CA); John B. Vincent, Toronto (CA)

(73) Assignees: Centre for Addiction and Mental Health, Toronto, Ontario (CA); The Hospital for Sick Children, Toronto, Ontario (CA)

( * ) Notice: Subject to any disclaimer, the term of this patent is extended or adjusted under 35 U.S.C. 154(b) by 0 days.

(21) Appl. No.: 11/352,153

(22) Filed: Feb. 9, 2006

(65) Prior Publication Data

US 2006/0194257 A1 Aug. 31, 2006

Related U.S. Application Data

(63) Continuation of application No. PCT/CA2005/000198, filed on Feb. 17, 2005.

(60) Provisional application No. 60/544,311, filed on Feb. 17, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 6,709,817 B1 | 3/2004 | Zoghbi et al. | |
| 2002/0137067 A1 | 9/2002 | Beaudet et al. | |
| 2003/0082606 A1 | 5/2003 | Lebo et al. | |
| 2005/0227229 A1 | 10/2005 | Lebo et al. | |

FOREIGN PATENT DOCUMENTS

JP 2001292775 10/2001

OTHER PUBLICATIONS

Hardy et al., 1998, Review, Science, 1998, 282: 1075-1079.*
Abdolmaleky et al., Am J Pharmacogenomics, 2005, 5: 149-160, Abstract.*
Kato, Epilepsy Research, 2006, 70S: S87-S95.*
Muhle et al., Pediatrics, 2004, 113: e472-e486.*
Peippo et al., Clinical Dysmorphology, 2006, 15: 47-54.*
Kleefstra et al., European Journal of Human Genetics, 2004, 12: 24-28.*
Ylisaukko-oja et al., American Journal of Medical Genetics, 2005, 132A: 121-124.*
Amir et al., J Med Genet, 2005, 42: e15.*
Mnatzakanian et al., Nature Genetics, 2004, 36: 339-341.*
Evans et al., European Journal of Human Genetics, 2005, 13: 124-126.*
Poirier et al., European Journal of Human Genetics, 2005, 13: 523-524.*
Bloecker, H., et al., Accession No. BX538060, GenBank Database, [online] Jun. 17, 2003, [retrieved on May 17, 2006] retrieved from the Internet http://www.ncbi.nlm.nih.gov/entrez/viewer.fcgi?db=nucleotide&val=31874178.
Bloecker, H., et al., Accession No. CAD97991, GENPEPT Database, [online] Jun. 17, 2003, [retrieved on May 17, 2006] retrieved from the Internet http://www.ncbi.nlm.nih.gov/entrez/viewer.fcgi?db=protein&val=31874179.
Kass, S.U., et al., Accession No. AF051768, GenBank Database [online] Jan. 5, 1999 [retrieved on May 17, 2006] retrieved from the Internet http://www.ncbi.nlm.nih.gov/entrez/viewer.fcgi?db=nucleotide&val=4105998.
Kass, S.U., et al., Accession No. AAD02651, GENPEPT Database, [online] Jan. 5, 1999 [retrieved on May 17, 2006] retrieved from the Internet http:/www.ncbi.nlm.nih.gov/entrez/viewer.fcgi?db=protein&val=4105999.
Coenraads, M., "Researchers Confirm Novel Form of the Rett Syndrome Protein," *Rett Syndrome Research Foundation: Press Releases: Mar. 22, 2004*, pp. 1-2, [retrieved on May 17, 2006] Retrieved from the Internet http://www.rsrf.org/about_rsrf/1.5.2.html.
Chen, R. Z., et al., "Deficiency of Methyl-CpG Binding Protein-2 in CNS Neurons Results in a Rett-like Phenotype in Mice," *Nature Genetics*, vol. 27, pp. 327-331 (2001).
Kriaucionis, S., et al., "The Major Form of MeCP2 has a Novel N-terminus Generated by Alternative Splicing," *Nucleic Acids Research*, vol. 32, No. 5, pp. 1818-1823 (2004).
Evans, J. C., et al., "Variation in Exon 1 Coding Region and Promotor of MECP2 in Rett Syndrome and Controls," *European Journal of Human Genetics*, vol. 13, pp. 124-126 (2005).
Kim, S., et al., "Novel *de novo* Nonsense Mutation of MECP2 in a Patient with Rett Syndrome," *Human Mutation*, Mutation in Brief #307 Online (2000).
Erlandson, A., et al., "Multiplex Ligation-Dependent Probe Amplification (MLPA) Detects Large Deletions in the MECP2 Gene of Swedish Rett Syndrome Patients," *Genetic Testing*, vol. 7, No. 4, pp. 329-332 (2003).
Bienvenu, T., et al., "MECP2 Mutations Account for most Cases of Typical Forms of Rett Syndrome," *Human Molecular Genetics*, vol. 9, No. 9, pp. 1377-1384 (2000).
Nicolao, P., et al., "DHPLC Analysis of the MECP2 Gene in Italian Rett Patients," *Human Mutation*, vol. 18, pp. 132-140 (2001).
Mnatzakanian, G. N., et al., "A Previously Unidentified MECP2 Open Reading Frame Defines a New Protein Isoform Relevant to Rett Syndrome," *Nature Genetics*, vol. 36, No. 4, pp. 339-341 (2004).
Vacca, M., et al., "Mutation Analysis of the MECP2 Gene in British and Italian Rett Syndrome Females," *J. Mol. Med.*, vol. 78, pp. 648-655 (2000).

(Continued)

*Primary Examiner*—Ileana Popa
(74) *Attorney, Agent, or Firm*—Hamilton, Brook, Smith & Reynolds, P.C.

(57) ABSTRACT

The invention is a novel MECP2E1 splice variant and its corresponding polypeptide. The invention also includes methods of using these nucleic acid sequences and proteins in medical diagnosis and treatment of neuropsychiatric disorders or development disorders.

12 Claims, 6 Drawing Sheets
(3 of 6 Drawing Sheet(s) Filed in Color)

OTHER PUBLICATIONS

Cheadle, J. P., et al., "Long-Read Sequence Analysis of the MECP2 Gene in Rett Syndrome Patients: Correlation of Disease Severity with Mutation Type and Location," *Human Molecular Genetics*, vol. 9, No. 7, pp. 1119-1129 (2000).

Bourdon, V., et al., "A Detailed Analysis of the MECP2 Gene: Prevalence of Recurrent Mutations and Gross DNA Rearrangements in Rett Syndrome Patients," *Hum. Genet*, vol. *108*, pp. 43-50 (2001).

Charman, T., et al., "Dimensional Phenotypic Analysis and Functional Categorisation of Mutations Reveal Novel Genotype-Phenotype Associations in Rett Syndrome," *European Journal of Human Genetics*, vol. *13*, pp. 1121-1130 (2005).

Christodoulou, J., et al., "RettBASE: The IRSA MECP2 Variation Database—a New Mutation Database in Evolution," *Human Mutation*, vol. *21*, pp. 466-472 (2003).

Amir, R. E., et al., "Rett Syndrome is Caused by Mutations in X-Linked MECP2, Encoding Methyl-CpG-Binding Protein 2," *Nature Genetics*, Vol. *23*, pp. 185-188 (1999).

Willard, H. F. and Hendrich, B.D., "Breaking the Silence in Rett Syndrome," *Nature Genetics*, vol. *23*, pp. 127-128 (1999).

Buyse, I. M. and Hendrich, B.D., "Diagnostic Testing for Rett Syndrome by DHPLC and Direct Sequencing Analysis of the MECP2 Gene: Identification of Several Novel Mutations and Polymorphisms," *Am. J. Hum. Genet.*, vol. *67*, pp. 1428-1436 (2000).

Thistlethwaite, W. A., et al., "Rapid Genotyping of Common MeCP2 Mutations with an Electronic DNA Microchip Using Serial Differential Hybridization," *Journal of Molecular Diagnostics*, vol. *5*, No. 2, pp. 121-126 (2003).

Hammer, S., et al., "The Phenotypic Consequences of MECP2 Mutations Extend Beyond Rett Syndrome," *Mental Retardation and Developmental Disabilities Research Reviews*, vol. *8*, pp. 94-98 (2002).

Meloni, I., et al., "A Mutation in the Rett Syndrome Gene, MECP2, Causes X-Linked Mental Retardation and Progressive Spasticity in Males," *Am. J. Hum. Genet.*, vol. *67*, pp. 982-985 (2000).

Samaco, R. C., et al., "Multiple Pathways Regulate MeCP2 Expression in Normal Brain Development and Exhibit Defects in Autism-Spectrum Disorders," *Human Molecular Genetics*, vol. *13*, No. 6, pp. 629-639 (2004).

Beyer, K. S., et al., "Mutation Analysis of the Coding Sequence of the MECP2 Gene in Infantile Autism," *Hum. Genet.*, vol. *111*, pp. 305-309 (2002).

Shi, J., et al., Detection of Heterozygous Deletions and Duplications in the MECP2 Gene in Rett Syndrome by Robust Dosage PCR (RD-PCR), *Human Mutation, Mutation in Brief #809 Online*, (2005).

Fyfe, S., et al., "InterRett and RettBASE: International Rett Syndrome Association Databases for Rett Syndrome," *Journal of Child Neurology*, vol. *18*, Issue 10, pp. 709-713 (2003).

Archer, H. L., et al., "Gross Rearrangements of the MECP2 Gene Are Found in Both Classical and Atypical Rett Syndrome Patients," *J. Med. Genet.*, vol. *43*, pp. 451-456 (2006).

Van Esch, H., et al., "Duplication of the MECP2 Region is a Frequent Cause of Severe Mental Retardation and Progressive Neurological Systems in Males," *Am. J. Hum. Genet.*, vol. *77*, pp. 442-453 (2005).

Boulanger, S., et al., "Evaluation of the Multiplex Ligation-Dependent Probe Amplification Technology in the Diagnosis of Rett Syndrome," *Am. J. Hum. Genet.*, vol. *73*, No. 5, pp. 572 (2003).

Aber, K. M., et al., "Methly-CpG-Binding Protein 2 Is Localized In The Postsynaptic Compartment: An Immunchemical Study Of Subcellular Fractions," *Neuroscience*, 116, 77-80 (2003).

Bienvenu, T., et al., "ARX, A Novel Prd-class-homeobox Gene Highly Expressed in the Telencephalon, Is Mutated in X-linked Mental Retardation," *Hum. Mol. Gen.*, 11(8): 981-991 (2002).

Brown, L. Y. and Brown, S. A., "Alanine Tracts: The Expanding Story of Human Illness and Trinucleotide Repeats," *Trends Genet.*, 20(1): 51-58 (2004).

Cohen, D., et al., "MECP2 Mutation in a Boy With Language Disorder and Schizophrenia," *Am. J. Psychiatry, Letters to the Editor*, 159:1 148-149 (2002).

Collins, A. L., et al., "Mild Overexpression of MeCP2 Causes a Progressive Neurological Disorder in Mice," *Hum. Mol. Gen.*, 13(21): 2679-2689 (2004).

Coy, J. F., et al., "A Complex Pattern of Evolutionary Conservation and Alternative Polyadenylation within the Long 3'-Untranslated Region of the Methyl-CpG-Binding Protein 2 Gene (MeCP2) Suggests a Regulatory Role in Gene Expression," *Hum. Mol. Genetics*, 8(7): 1253-1262 (1999).

D'Esposito, M., et al., "Isolation, Physical Mapping and Northern Analysis of the X-Linked Human Gene Encoding Methyl CpG-Binding Protein, MECP2," *Mann. Genome.*, 7, 533-535 (1996).

Grenskov, K., et al., "Screening of the ARX Gene in 682 Retarded Males," *Eur. J. Hum. Genet.*, 12: 701-705 (2004).

Hagberg, B., "Clinical Manifestations and Stages of Rett Syndrome," *Mental Retardation and Developmental Disabilities Research Reveiws*, 8:61-65 (2002).

Hardingham, G. E., et al., "A Calcium Microdomain Near NMDA Receptors: On Switch for ERK-dependent Synapse-to-Nucleus Communication," *Nature Neuroscience*, 4(6): 565-566 (2001).

Inoue, K. and Keegstra, K., "A Polyglycine Stretch is Necessary for Proper Targeting of the Protein Translocation Channel Precursor to the Outer Envelope Membrane of Chloroplasts," *The Plant Journal*, 34: 661-669 (2003).

Miltenberger-Miltenyi, G. and Laccone, F., "Mutations and Polymorphisms in the Human Methyl CpG-Binding Protein MECP2," *Human Mutation*, 22:107-115 (2003).

Orrico, A., et al., "MECP2 Mutation in Male Patients with Nonspecific X-linked Mental Retardation," *Febs Letters*, 481: 285-288 (2000).

Reichwald, K., et al., "Comparative Sequence Analysis of the MECP2-Locus in Human and Mouse Reveals New Transcribed Regions," *Mamm. Genome.*, 11: 182-190 (2000).

Schouten, J. P., et al., "Relative Quantification of 40 Nucleic Acid Sequences by Multiplex Ligation-Dependent Probe Amplification," *Nucleic Acids Research*, 30(12): e57 (2002).

Shahbazian, M. D., et al., "Insight into Rett Syndrome: MeCP2 Levels Display Tissue-and-Cell-Specific Differences and Correlate with Neuronal Maturation," *Hum. Mol. Gene.*, 11(2): 115-124 (2002).

Stancheva, I., et al., "A Mutant form of MeCP2 Protein Associated with Human Rett Syndrome Cannot Be Displaced from Methylated DNA by Notch in Xenopus Embryos," *Mol. Cell.*, 12: 425-435 (2003).

Utsch, B., et al., "A Novel Stable Polyalanine [Poly(A)] Expansion in the HOXA13 Gene Associated with Hand-Foot-Genital Syndrome: Proper Function of Poly(A)-Harbouring Transcription Factors Depends On a Critical repeat Length?," *Hum. Genet.* 110:488-494 (2002).

Muhle, R., et al., "The Genetics of Autism," *Pediatrics*, 113:472-486 (2006).

Kato, M., "A New Paradigm for West Syndrome Based on Molecular and Cell Biology," *Epilepsy Research*, 70:87-95 (2006).

Abdolmaleky, H.M. et al., "Genetics and Epigenetics in Major Psychiatric Disorders: Dilemmas, Achievements, Applications, and Future Scope," *Am. J. Pharmacogenomics*, 5:149-160 (2005).

Hardy, J., and K. Gwinn-Hardy, "Genetic Classification of Primary Neurodegenerative Disease," *Science*, 282:1075-1079 (1998).

\* cited by examiner

A.

B.

C.

US 7,670,773 B2

MECP2E1 GENE

RELATED APPLICATIONS

This application is a continuation of International Application No. PCT/CA2005/000198 which designated the United States and was filed on Feb. 17, 2005, published in English, which claims the benefit of U.S. Provisional Application No. 60/544,311, filed on Feb. 17, 2004. The entire teachings of the above applications are incorporated herein by reference.

BACKGROUND OF THE INVENTION

Neuropsychiatric disorders account for six of the ten highest impact diseases worldwide, according to the World Health Organization. Cost to the US economy is $100 billion one of every four persons entering physician offices has a diagnosable mental disorder.

Rett syndrome (RTT) (OMIM #312750) is characterized by onset, in girls, of a gradual slowing of neurodevelopment in the second half of the first year of life towards stagnation by age four, followed by regression and loss of acquired fine motor and communication skills. A pseudostationary period follows during which a picture of preserved ambulation, aberrant communication and stereotypic hand wringing approximates early autism. Regression, however, remains insidiously ongoing and ultimately results in profound mental retardation.

Up to 80% of patients with RTT have mutations in exons 3 and 4 of the 4-exon MECP2 gene (FIG. 1a) encoding the MeCP2 transcriptional repressor. Mutations in the remaining 20% of patients has remained elusive. In the known transcript of the gene all four exons are utilized, the translation start site is in exon 2, and exon 1 and most of exon 2 form the 5' untranslated region (UTR). For clarity, this transcript is named MECP2E2 (previously MECP2A), and its encoded protein MeCP2E2 (previously MeCP2A).

No mutation specific to the MeCP2E2-defining exon 2 has been found to date despite several hundred patients analyzed for mutations in this exon These studies did not include exon 1 as it was considered non-coding.

Non-inactivating MECP2 mutations have also been associated with phenotypes that overlap RTT such as mental retardation and autism. There is a need for the identification of further mutations to account for the remaining 20% of RTT patients so that methods of diagnosing and treating RTT can be identified.

Mutations in the Rett syndrome gene, MECP2, have also been found among autism patients as well as in patients with childhood onset psychosis, Angelman syndrome, non-syndromic mental retardation and neo-natal encepalopathy, demonstrating that there may be diverse phenotypic consequences of mutations in MECP2.

SUMMARY OF THE INVENTION

The present inventors have identified a novel open reading frame of the MECP2 gene, that is called MECP2E1. Inspection of the 5'UTR revealed that, whereas exon 2 has a number of in-frame stops upstream of the ATG, exon 1 contains an open reading frame across its entire length including an ATG. This open reading frame encodes a transcript composed of exons 1, 3 and 4 of the MECP2 gene. MECP2E1 is similar to MECP2E2 (GenBank accession #NM_004992, (SEQ ID NO:1), except with nucleotides 71-193 absent, corresponding to the splicing out of exon 2.

Accordingly, the present invention provides an isolated nucleic acid molecule comprising a sequence encoding the MeCP2E1 protein. The invention also includes the corresponding polypeptide, MeCP2E1.

In one embodiment, the purified and isolated nucleic acid molecule comprises
   (a) a nucleic acid sequence encoding a protein as shown in SEQ ID No. 4;
   (b) a nucleic acid sequence complementary to (a);
   (c) a nucleic acid sequence that has substantial homology to (a) or (b);
   (d) a nucleic acid sequence that is an analog to a nucleic acid sequence of (a), (b), or (c);
   (e) a fragment of (a) to (d) that is at least 15 bases, preferably 20 to 30 bases, and which will hybridize to a nucleic acid sequence of (a), (b), (c) or (d) under stringent hybridization conditions; or
   (f) a nucleic acid molecule differing from any of the nucleic acids of (a) to (c) in codon sequences due to the degeneracy of the genetic code.

In a specific embodiment of the invention, an isolated nucleic acid molecule is provided having a sequence as shown in SEQ ID No. 3 or a fragment or variant thereof.

The inventors have found that patients with a neuropsychiatric disorder or developmental disorder such as Rett's syndrome and mental retardation, had mutations in exon 1 of the MECP2E1 gene. Accordingly, the present invention provides a method of detecting a neuropsychiatric disorder or developmental disorder comprising detecting a mutation or deletion in exon 1 of the MECP2E1 sequence (SEQ ID No. 3). A mutation can be detected by sequencing PCR products from genomic DNA using primers X1F/X1R: mutation screening primers (FIG. 1). Detection of insertion or deletion mutations may require the cloning of the PCR product into a suitable plasmid vector, followed by transfection into *E. Coli*, and sequencing of clones from isolated colonies. Alternatively, a mutation can be detected by multiple ligation-dependent probe amplification (MLPA) using 20 probe pairs that target the four MECP2 exons, six X-linked control regions and ten autosomal control regions. A mutation or deletion can also be detected by assaying for the protein product encoded by MECP2E1.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will now be described in relation to the drawings in which.

DETAILED DESCRIPTION OF THE INVENTION

Figures 1A, 1B, 1C, 1D, 1E, 1F:
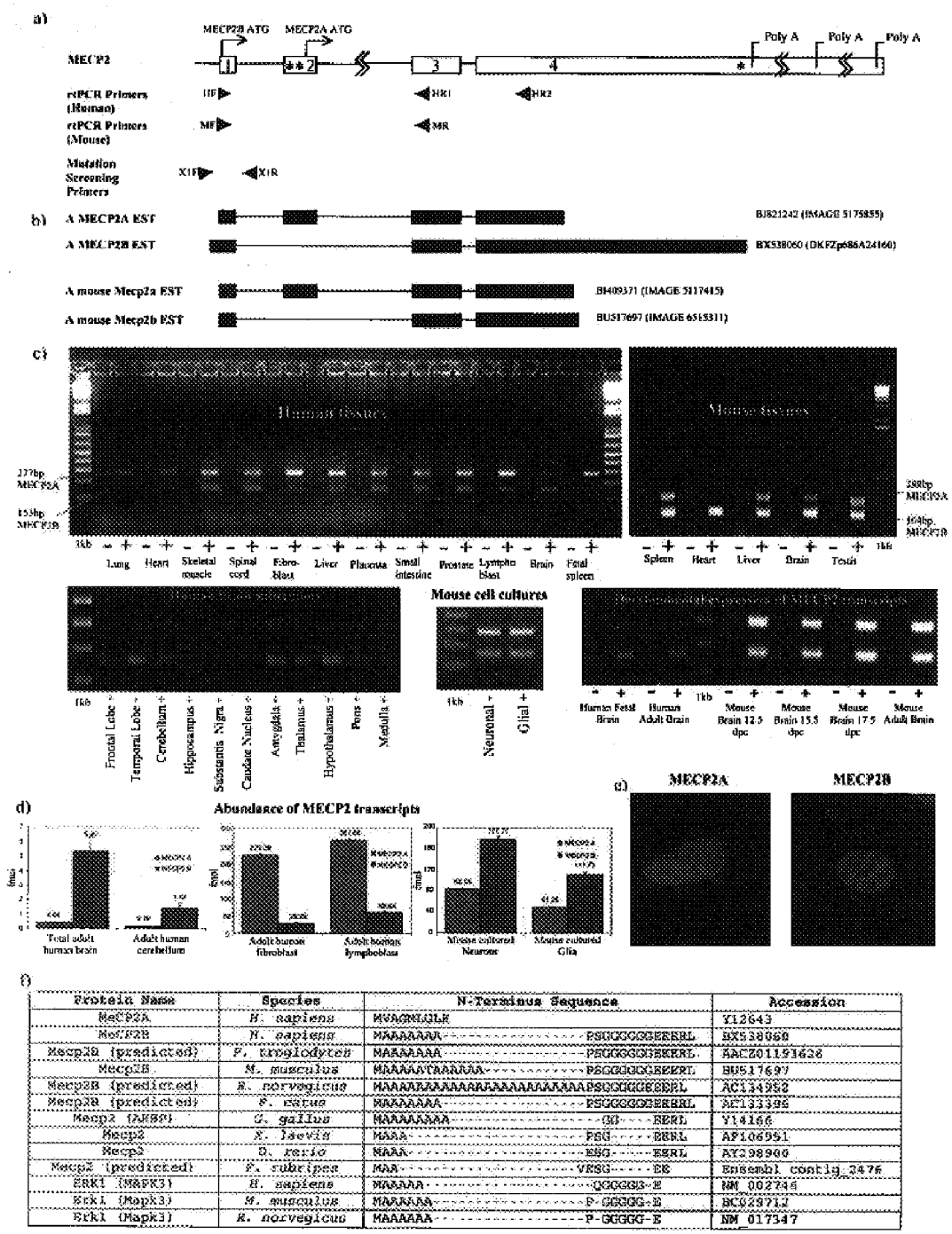
FIG. 1 shows MECP2 5' splice variants. a) Structure of the MECP2 gene. Numbered boxes indicate exons; asterisks indicate in-frame stop codons. In the traditional MECP2E2 splice variant, the start codon is in exon 2. In MECP2E1, exon 2 is not present and the start codon is in exon 1. HF/HR1 and MF/MR: human and mouse primer pairs used in the rtPCR experiments shown in panel c. HR2: a second human reverse primer, which confirms the results obtained with HR1 (data not shown). X1F/X1R: mutation screening primers (see FIG. 2). Primer sequences (5'-3'): HF-ctcggagagagggctgtg (SEQ ID No. 5), HR1-cttgaggggtttgtccttga (SEQ ID No. 6), HR2-cgtttgatcaccatgacctg (SEQ ID No. 7), MF-aggaggcgaggag-gagagac (SEQ ID No. 8), MR-ctggctctgcagaatggtg (SEQ ID No. 9), X1F-ccatcacagccaatgacg (SEQ ID No. 19), X1R-aggggagggtagagaggag (SEQ ID No. 20). b) Examples of MECP2 ESTs. c) PCR results using primers in (a) (HF/HR1 and MF/MR) on cDNA from indicated adult tissues (except where indicated otherwise) and cell cultures; d.p.c.: days postcoitum. d) Transcript-specific real-time quantitative PCR (SYBR Green detection method) on cDNA from indicated tissues or cell cultures. e) 3'myc-tagged MeCP2E1 (and MeCP2E2) localize principally in the nucleus, and in indeterminate puncti in the cytoplasm. f) N-termini of indicated proteins; dashes represent no amino acids.

The present inventors have identified a MECP2 splice variant that contributes to new coding sequence that may contain mutations in patients with neuropsychiatric disorders such as Rett's syndrome and mental retardation.

I. Nucleic Acid Molecules of the Invention

As hereinbefore mentioned, the present invention relates to isolated MECP2E1 nucleic acid molecules. The term "isolated" refers to a nucleic acid substantially free of cellular material or culture medium when produced by recombinant DNA techniques, or chemical precursors, or other chemicals when chemically synthesized.

The term "nucleic acid" is intended to include DNA and RNA and can be either double stranded or single stranded. The term is also intended to include a strand that is a mixture of nucleic acid molecules and nucleic acid analogs and/or nucleotide analogs, or that is made entirely of nucleic acid analogs and/or nucleotide analogs.

Broadly stated, the present invention provides an isolated nucleic acid molecule containing a sequence encoding the MECP2E1 transcript of the MECP2 gene. Accordingly, the present invention provides an isolated nucleic acid molecule containing a sequence encoding MECP2E1 shown in SEQ ID No: 4 or a fragment, variant, or analog thereof.

In one embodiment, the purified and isolated nucleic acid molecule comprises (a) a nucleic acid sequence encoding a MECP2E1 protein as shown in (SEQ ID No. 4);

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, the isolated nucleic acid molecule has a sequence as shown in SEQ ID No. 3 or a fragment or variant thereof.

The term "MECP2E1" means an isoform of the MECP2 gene that contains exons 1, 3 and 4 but lacks exon 2. This gene was previously referred to as MECP2B but is now called MECP2E1 indicating the translation start site in exon one. The term "MECP2E1" includes the nucleic acid sequence as shown in SEQ ID No. 3 as well as mutations, variants and fragments thereof that are associated with neuropsychiatric disorders and developmental disorders.

It will be appreciated that the invention includes nucleic acid molecules encoding truncations of the MeCP2E1 proteins of the invention, and analogs and homologs of the MeCP2E1 proteins of the invention and truncations thereof, as described below.

Further, it will be appreciated that the invention includes nucleic acid molecules comprising nucleic acid sequences having substantial sequence homology with the nucleic acid sequences of the invention and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80-90% identity with the nucleic acid sequences of the invention.

Sequence identity is most preferably assessed by the algorithm of the BLAST version 2.1 program advanced search (BLAST is a series of programs that are available online at www.ncbi.nlm.nih.gov/BLAST. The advanced blast search (www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default).). For example, if a nucleotide sequence (called "Sequence A") has 90% identity to a portion of the nucleotide sequence in SEQ ID No: 3, then Sequence A will be identical to the referenced portion of the nucleotide sequence in SEQ ID No: 3, except that Sequence A may include up to 10 point mutations, such as substitutions with other nucleotides, per each 100 nucleotides of the referenced portion of the nucleotide sequence in SEQ ID No: 3. Nucleotide sequences functionally equivalent to the MECP2E1 transcript can occur in a variety of forms as described below.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in SEQ ID No: 3, with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID No: 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Another aspect of the invention provides a nucleic acid molecule, and fragments thereof having at least 15 bases, which hybridizes to the nucleic acid molecules of the invention under hybridization conditions. Such nucleic acid molecules preferably hybridize to all or a portion of MECP2E1 or its complement under stringent conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a MeCP2E1 polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 50° C. High stringency conditions are: 0.1×SSC, 0.1% SDS at 65° C. Moderate stringency is about 1×SSC 0.1% SDS at 60 degrees Celsius. The parameters of salt concentration and temperature can be varied to achieve the optimal level of identity between the probe and the target nucleic acid.

Figure 6:
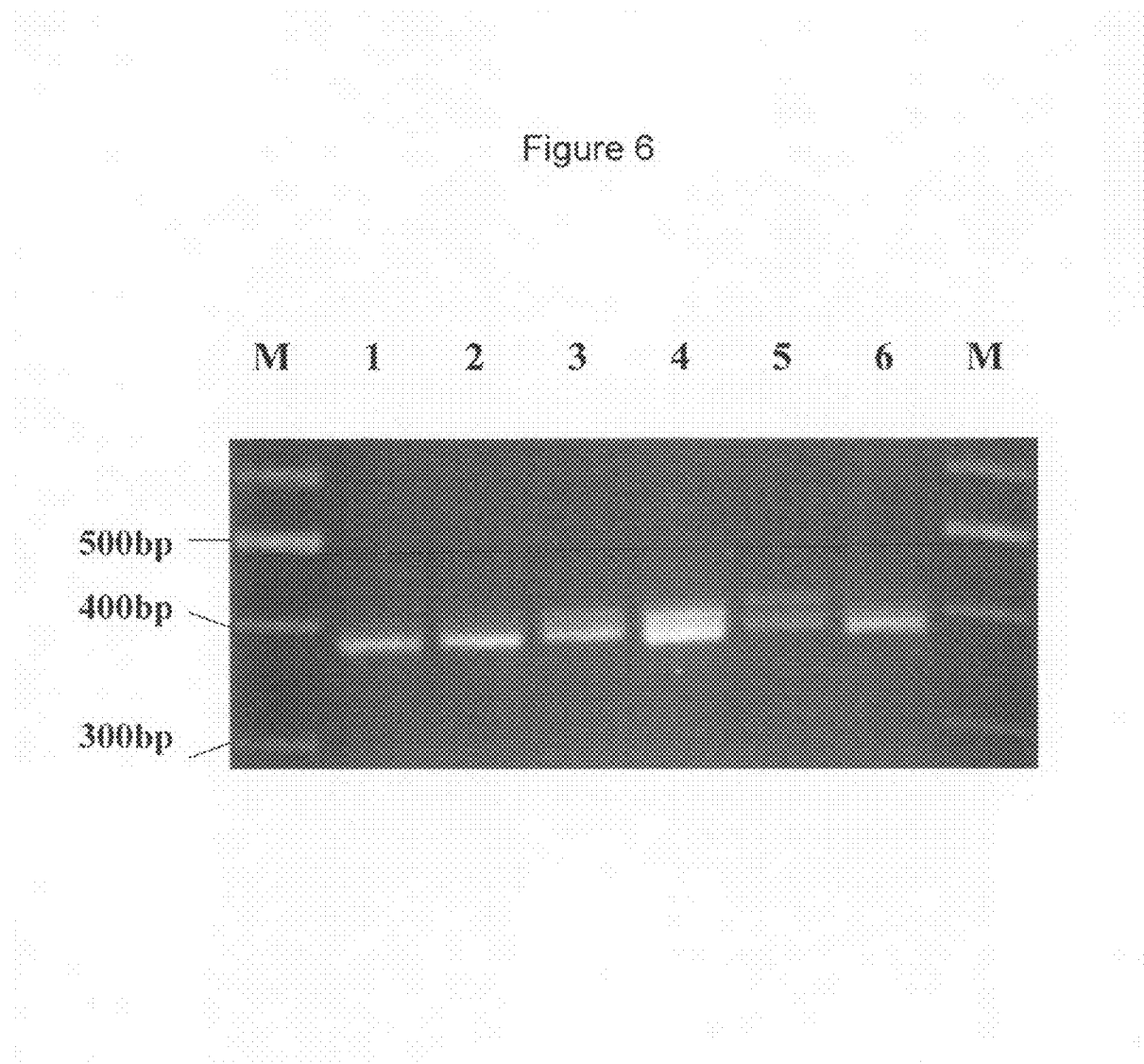
FIG. 6 shows a high resolution agarose gel (2.2%) of PCR product for MECP exon 1 for negative controls (Lanes 1 and 2), 3 bp insertion (Lanes 3 and 4), 9 bp insertion (Lane 5) and 2 bp deletion (Lane 6). Size ladder (M) 100 bp ladder (MBI Fermentas), flanks the PCR lanes.

Isolated and purified nucleic acid molecules having sequences which differ from the nucleic acid sequence shown in SEQ ID No: 3 due to degeneracy in the genetic code are also within the scope of the invention. The genetic code is degenerate so other nucleic acid molecules, which encode a polypeptide identical to the MeCP2E1 amino acid sequence (FIG. 6(b)) may also be used.

The present invention also includes mutated forms of MEC2P2E1 associated with a neuropsychiatric disorder or developmental disorder including the specific mutations listed in Table 1. Specifically, the following mutations are associated with Rett's syndrome: (1) an 11 bp deletion in nucleotides 38 to 54 shown in SEQ ID No. 1; (2) a deletion of exon 1 containing nucleotides 1-69 shown in SEQ ID No. 1; (3) a adenosine to threonine change at nucleotide position 8 shown in SEQ ID No. 1; and (4) a deletion in the sequence TG at nucleotide positions 70-71 in SEQ ID No. 1.

The following mutations are associated with developmental delay: (1) an insertion of one or more copies of the trinucleotide sequence GCC between nucleotides 11 and 29 shown in SEQ ID No. 1; (2) a deletion of one or more copies of the trinucleotide sequence GCC between nucleotides 11 and 29 shown in SEQ ID No. 1; (3) an insertion of the nucleotide sequence GGA between nucleotides 38 and 54 shown in SEQ ID No. 1; (4) a deletion of the nucleotide sequence GC at nucleotides −38 and −39 upstream of nucleotide 1 shown in SEQ ID No. 1 and (5) a deletion of the nucleotide sequence AG at nucleotides −19 and −20 upstream of nucleotide 1 shown in SEQ ID No. 1.

With respect to mutations (4) and (5) in the developmental delay group, these are upstream of nucleotide 1 shown in SEQ ID No. 1 GenBank Accession number BX538060 has the upstream sequences. Therefore, for greater clarity mutation (4), that consists of a deletion of the nucleotide sequence GC at nucleotides −38 and −39, corresponds to nucleotides 11-12 of sequence BX538060; and mutation (5), that consists of a deletion of the nucleotide sequence AG at nucleotides −19 and −20, corresponds to nucleotides 30-31 of BX538060.

Nucleic acid molecules from MECP2E1 can be isolated by preparing a labeled nucleic acid probe based on all or part of the nucleic acid sequences as shown in SEQ ID No: 3, and using this labelled nucleic acid probe to screen an appropriate DNA library (e.g. a cDNA or genomic DNA library). Nucleic acids isolated by screening of a cDNA or genomic DNA library can be sequenced by standard techniques. Another method involves comparing the MECP2E1 sequence to other sequences, for example using bioinformatics techniques such as database searches or alignment strategies, and detecting the presence of a MECP2E1 nucleic acid sequence.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in SEQ ID No: 3 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the MeCP2E1 protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in SEQ ID No: 3 may be inverted relative to its normal presentation The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated MeCP2E1 protein encoded by the nucleic acid molecules of the invention. Within the context of the present invention, a protein of the invention may include various structural forms of the primary protein which retain biological activity.

Broadly stated, the present invention provides an isolated protein encoded by exon 1, 3 and 4 of the MECP2 gene.

In a preferred embodiment of the invention, the MeCP2E1 protein has the amino acid sequence as shown in SEQ ID No. 4 or a fragment or variant thereof.

The invention also includes mutated forms of the MeCP2E1 protein that are associated with a neuropsychiatric disorder or developmental disorder. Specifically, the invention includes the mutations in MECP2E1 described in Table 1.

In addition to full length amino acid sequences, the proteins of the present invention also include truncations of the protein, and analogs, and homologs of the protein and truncations thereof as described herein. Truncated proteins may comprise peptides of at least fifteen amino acid residues.

Analogs or variants of the protein having the amino acid sequence shown in SEQ ID No. 4 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequence shown in SEQ ID No. 4. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ ID No. 4. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence having the exon 1 region shown in SEQ ID No. 4 and/or truncations thereof as described herein.

A homologous protein includes a protein with an amino acid sequence having at least 70%, preferably 80-90% identity with the amino acid sequence as shown in SEQ ID No. 4 and includes the exon 1 region characteristic of the MeCP2E1 protein. As with the nucleic acid molecules of the invention, identity is calculated according to methods known in the art. Sequence identity is most preferably assessed by the algorithm of BLAST version 2.1 advanced search. BLAST is a series of programs that are available online at www.ncbi.nlm.nih.gov/BLAST. The advanced blast search (.ncbi.nlm.nih.gov/blast/blast.cgi?Jform=1) is set to default parameters (i.e. Matrix BLOSUM62, Gap existence cost 11; Per residue gap cost 1; Lambda ration 0.85 default).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown SEQ ID No: 3. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Applications

A. Diagnostic Applications

As previously mentioned, the present inventors have isolated a novel splice variant of the MECP2 gene, MECP2E1, and have shown that exon 1 is deleted or mutated in people with neuropsychiatric disorders or developmental disorders such as Rett's syndrome or mental retardation. As a result, the present invention also includes a method of detecting a neuropsychiatric or developmental disorder by detecting a mutation or deletion in the MECP2E1 nucleic acid or MeCP2E1 protein.

The term "neuropsychiatric disorder" as used herein includes, but is not limited to, autism/autism spectrum disorder, epilepsy, Angelman syndrome, Prader-Willi syndrome, encephalopathy, schizophrenia, bipolar affective disorder, depression, obsessive compulsive disorder, panic disorder, attention deficit hyperactivity disorder, and ataxia.

The term "developmental disorder" includes but is not limited to, mental retardation.

i) Detecting Mutations in the Nucleic Acid Sequence

In one embodiment, the present invention provides a method for detecting a neuropsychiatric or developmental disorder comprising detecting a deletion or mutation in exon 1 of the MECP2 gene in a sample obtained from an animal, preferably a mammal, more preferably a human.

The Examples and Table 1 summarize some of the mutations found in MECP2E1 in patient's with Rett's syndrome or developmental delay. (They are also described in Section I). Screening assays can be developed for each of the mutations. Examples of methods that can be used to detect mutations include sequencing, polymerase chain reaction, reverse transcription-polymerase chain reaction, denaturing HPLC, electrophoretic mobility, nucleic acid hybridization, fluorescent in situ hybridization and multiplex ligation-dependent probe amplification. Details of screening assays that may be employed are provided in Examples 3, 4 or 5.

Rett's syndrome has been shown to be caused by deletions in exon 1 of MECP2. Patients homozygous for these deletions can be detected by PCR-amplifying and sequencing exon 1 and flanking sequences using X1F/X1R primers. Consequently, the present invention includes a method for determining a deletion in exon 1 of the MECP2 gene by a method comprising:

(a) amplifying the nucleic acid sequences in the sample with primers X1F (5'-CCATCACAGCCAATGACG-3') (SEQ ID No. 19) and X1R (5'-AGGGGGAGGGTAGAGAG-GAG-3') (SEQ ID No. 20) in a polymerase chain reaction;

(b) amplifying the nucleic acid sequences from a control with same primers;

(c) sequencing the amplified sequences; and (d) comparing the sample sequences to the control sequences wherein deletion of nucleotides in the sample sequence compared to the control sequence indicates that the sample is from an animal with Rett's syndrome.

Additional exon 1 mutations not detectable by the PCR reaction, can be identified using multiplex ligation-dependent probe amplification (MLPA) in all four exons. MLPA analysis is described in reference 5 and in Schouten, U.S. application Ser. No. 10/218,567, (publication No. 2003/0108913) which are incorporated herein in by reference. Accordingly, the present invention includes a method for determining a deletion in exon 1 of the MECP2 gene by performing MLPA analysis with 20 probe pairs that target the four MECP2 exons, six X-linked control regions and ten autosomal control regions.

One skilled in the art will appreciate that other methods, in addition to the ones discussed above and in the examples, can be used to detect mutations in exon 1 of the MECP2 gene. For example, in order to isolate nucleic acids from a sample, one can prepare nucleotide probes from the nucleic acid sequences of the invention. In addition, the nucleic acid probes described herein (for example, see FIG. 1) can also be used. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Accordingly, the present invention also relates to a method of detecting the presence of a nucleic acid molecule containing exon 1 of the MECP2 gene in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

Hybridization conditions which may be used in the methods of the invention are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

Prior to hybridizing a sample with DNA probes, the sample can be treated with primers that flank the MECP2 gene in order to amplify the nucleic acid sequences in the sample. The primers used may be the ones described in the present application. For example, primers specific for human MECP2 include HF(ctcggagagagggctgtg) (SEQ ID No. 5), HR1 (ctgaggggtttgtccttga) (SEQ ID No. 6), HR2(cgtttgatcaccatgac-ctg) (SEQ ID No. 7). Primers for mouse MECP2 include MF(aggaggcgaggaggagagac) (SEQ ID NO. 8) and MR (ctg-gctctgcagaatggtg) (SEQ ID No. 9). In addition, the sequence of the MECP2 gene provided herein also permits the identification and isolation, or synthesis of new nucleotide sequences which may be used as primers to amplify a nucleic acid molecule of the invention. The primers may be used to amplify the genomic DNA of other species. The PCR amplified sequences can be examined to determine the relationship between the genes of various species.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorescein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis et al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp 3-12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UV) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp 3-12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", Aug. 1991, Vol. 1(1), page 5, and European Published Application No. 0320308, published Jun. 14, 1989, and U.S. Pat. No. 5,130,238 to Malek).

(ii) Detecting the MeCP2E1 Protein

In another embodiment, the present invention provides a method for detecting a neuropsychiatric or developmental disorder comprising detecting a deletion or mutation in the MeCP2E1 protein in a sample from an animal.

The MeCP2E1 protein of the present invention may be detected in a biological sample using antibodies that are specific for MeCP2E1 using various immunoassays that are discussed below.

Conventional methods can be used to prepare the antibodies. For example, by using a peptide from the MeCP2E1 protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CipA protein (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immunoprecipitation, latex agglutination, hemagglutination, and histochemical tests. Thus, the antibodies may be used to identify or quantify the amount of a protein of the invention in a sample in order to diagnose the presence of Rett's syndrome.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of MeCP2E1 can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of MeCP2E1 can be determined by measuring the amount of antibody bound to the protein using substances that interact specifically with the antibody to cause agglutination or precipitation. In particular, labelled antibody against an antibody specific for a protein of the invention, can be added to the reaction mixture. The presence of a protein of the invention can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention the kit includes antibodies of the invention and reagents required for binding of the antibody to a protein of the invention in a sample.

The kits may include nucleic acid molecules, proteins or antibodies of the invention (described above) to detect or treat neuropsychiatric disorders and developmental disorders together with instructions for the use thereof.

The methods and kits of the present invention may be used to detect neuropsychiatric and developmental disorders such as Rett's syndrome and mental retardation. Samples which may be tested include bodily materials such as blood, urine, serum, tears, saliva, feces, tissues, organs, cells and the like. In addition to human samples, samples may be taken from mammals such as non-human primates, etc.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. Therapeutic Applications

As mentioned previously, the nucleic acid molecules of the present invention are deleted or mutated in people with neuropsychiatric disorders and developmental disorders. Accordingly, the present invention provides a method of treating or preventing neuropsychiatric disorders and developmental disorders by administering a nucleic acid sequence containing a sufficient portion of the MECP2E1 splice variant to treat or prevent neuropsychiatric disorders and developmental disorders. The present invention includes a use of a nucleic acid molecule or protein of the invention to treat or detect neuropsychiatric disorders and developmental disorders.

Recombinant molecules comprising a nucleic acid sequence or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

The nucleic acid sequences may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

C. Experimental Models

The present invention also includes methods and experimental models for studying the function of the MECP2 gene and MeCP2E1 protein. Cells, tissues and non-human animals that lack the MECP2E1 splice variant or partially lack in MeCP2E1 expression may be developed using recombinant expression vectors having a specific deletion or mutation in the MECP2E1 gene. A recombinant expression vector may be used to inactivate or alter the MECP2 gene by homologous recombination and thereby create a MECP2E1 deficient cell, tissue or animal. In particular, a targeted mutation could be designed to result in deficient MECP2E1 while MECP2E2 remains unaltered. This can be accomplished by targeting exon 1 of the MECP2 gene.

Null alleles may be generated in cells, such as embryonic stem cells by deletion mutation. A recombinant MECP2 gene may also be engineered to contain an insertion mutation which inactivates MECP2E1. Such a construct may then be introduced into a cell, such as an embryonic stem cell, by a technique such as transfection, electroporation, injection etc. Cells lacking an intact MECP2 gene may then be identified, for example by Southern blotting, Northern Blotting or by assaying for MECP2E1 using the methods described herein. Such cells may then be fused to embryonic stem cells to generate transgenic non-human animals deficient in MECP2E1. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on MECP2E1 expression. The present invention also includes the preparation of tissue specific knock-outs of the MECP2E1 variant.

The following non-limiting examples are illustrative of the present invention:

EXAMPLES

Example 1

Identification of MEC2E1 Splice Variant

Inspection of the 5'UTR revealed that, whereas exon 2 has a number of in-frame stops upstream of the ATG, exon 1 contains an open reading frame across its entire length including an ATG. Submitting a theoretical construct composed of exons 1, 3 and 4 to the ATGpr program (www.hri.co.jp/atgpr/), which predicts the likelihood of an ATG to be an initiation codon based on significance of its surrounding Kozak nucleotide context, returned a reliability score of 97% compared to 64% for MECP2E2. A search in EST databases identified eight examples of our theorized transcript (named MECP2E1) (FIG. 1b) (vs. 14 examples of MECP2E2). MECP2E1 would be predicted to encode a new variant, MeCP2E1, with an alternative longer N-terminus determined by exon 1.

Example 2

Expression of MECP2E1

To confirm that MECP2E1 is in fact expressed and not an artifact of cDNA library preparations, cDNA from a variety of tissues was PCR-amplified using a 5'-primer in exon 1 and a 3'-primer in exon 3 (FIG. 1a). Two PCR products corresponding to MECP2E2 and MECP2E1 by size and sequence were obtained in all tissues, including fetal and adult brain, and in brain subregions (FIG. 1c). Results in mouse were similar (FIG. 1c). The expression levels of the two transcripts in adult human brain were quantified. MECP2E1 expression is 10 times higher than MECP2E2 (FIG. 1d). The subcellular localization of MeCP2E1 following transfection of 3' myc-tagged MECP2E1 into COS-7 cells was found to be principally in the nucleus (FIG. 1e).

MECP2E1 was not detected in previous expression studies. Northern analyses reveal three transcripts, 1.9, 5 and 10.1 kb, with the differences in size due to alternative polyadenylation signal usage (4,6,8) (FIG. 1a). MECP2E1 differs from MECP2E2 in lacking the 124-nucleotide exon 2. At the 5 and 10.1 kb positions on the gel, the two transcripts would not be separable. In the 1.9 kb range, published northern blots do show a thick or double band likely corresponding to the two transcripts. Likewise, conventional western blot analysis would not allow resolution of the two MeCP2 isoforms (molecular weight difference<0.9 kD; FIG. 1f).

Example 3

Mutations in MECP2E1 in Rett's Syndrome

Figure 2:
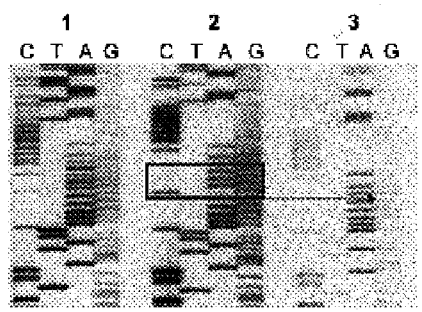
FIG. 2 shows a deletion mutation in patient V1. a1) Sequence of PCR product from genomic DNA using primers X1F/X1R (FIG. 1a). Note mixed sequence. a2) and a3) Sequences of clones of the patient's wild-type and mutant alleles respectively; red box indicating the 11 nucleotides deleted in the mutated allele. b) Electropherograms of the same cloned wild-type and deleted alleles. c) PCR on indicated cDNAs using primers HF/HR1 (FIGS. 1a,c). Lanes 1 and 2 (on 2.5% high resolution agarose) are from control and patient whole blood respectively. Lanes 3 to 8 (on 6% denaturing polyacrylamide) are from control blood (3), patient blood (4), control fetal brain (5), control adult brain (6), control testis (7) and control genomic DNA (8). Note that expression of the patient's MECP2E2 transcript with the 11 bp exon 1 deletion (band at 266 bp) is not diminished compared to the non-deleted allele (277 bp). The 141 and 152 bp bands are the deleted and non-deleted MECP2E1 transcripts respectively.
Figure 2:
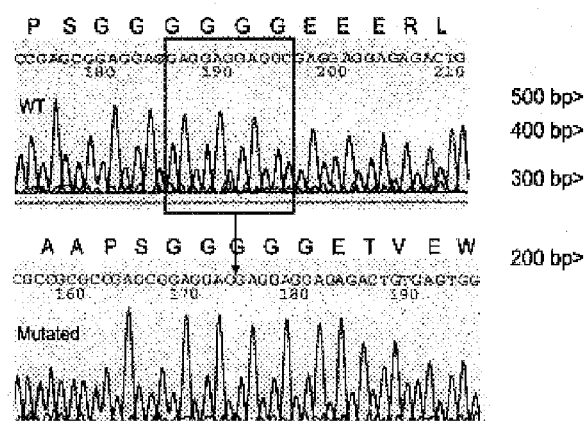
Figure 2:
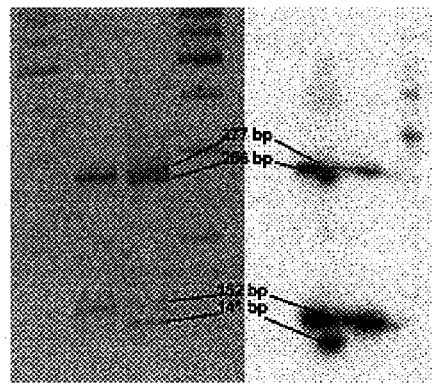

To determine whether the new coding region is mutated in Rett's syndrome, Exon 1 and flanking sequences were PCR-amplified and sequenced in 19 girls with typical RTT in whom no mutations had been found in the other exons. One patient (V1) was found to carry an 11 bp deletion mutation in exon 1 (FIG. 2). The deletion occurs within the predicted exon 1 open reading frame of MECP2E1 and leads to a frame shift that results in a missense amino acid sequence followed by a premature stop codon after amino acid 36. It does not affect the coding sequence of MECP2E2. This sequence change was not found in 200 control individuals including the patient's parents and brother.

Figure 3:
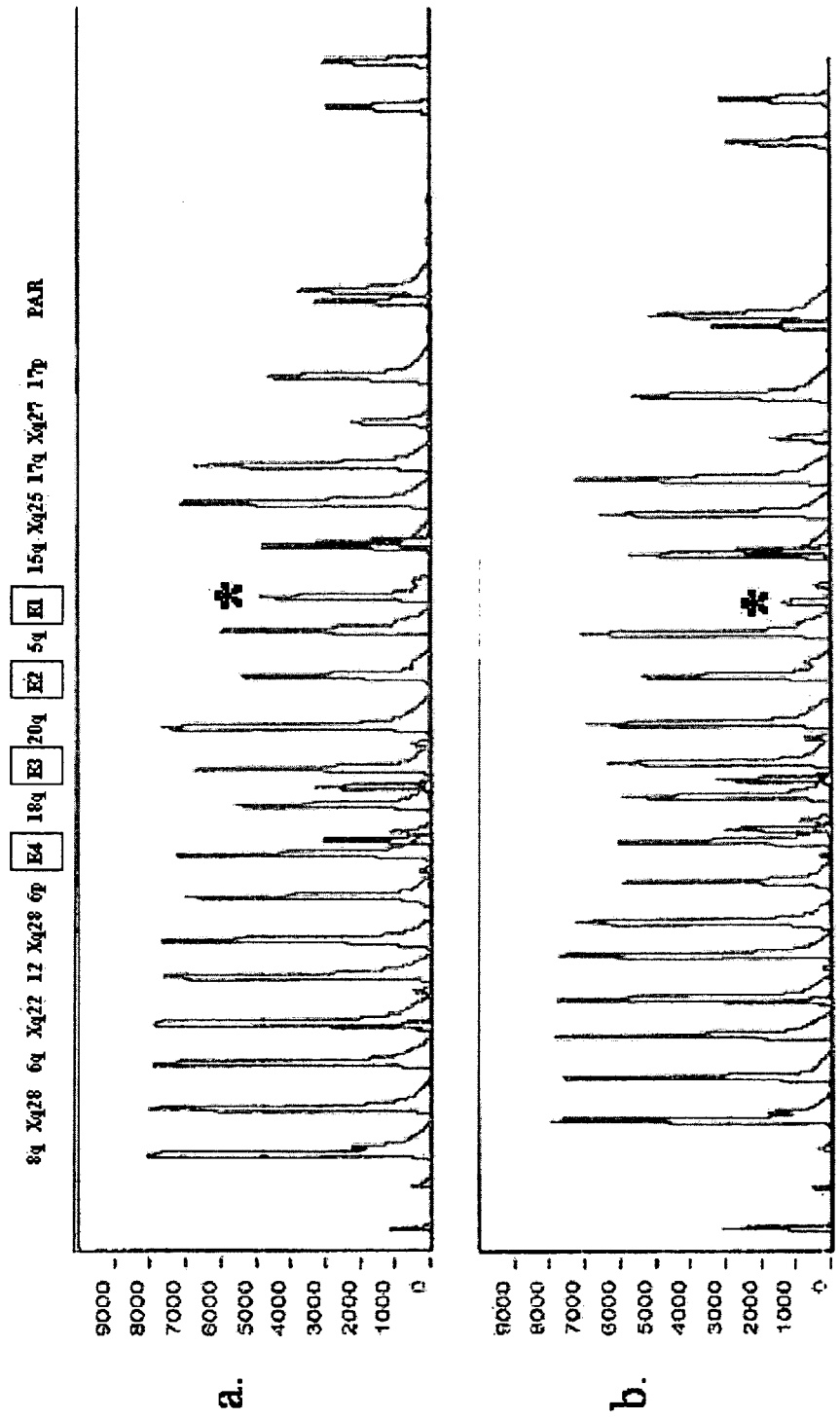
FIG. 3 shows a deletion mutation in patient V2. MECP2 Multiplex ligation-dependent probe amplification (MLPA) peak profiles are shown. Control loci are listed along the top. Boxed regions (E1-E4) indicate MECP2 exons 1-4. a) MLPA profile of normal control. b) MLPA profile of patient V2 shows a hemizygous exon 1 deletion (asterisk). The result was consistently reproducible and sequencing ruled out the possibility of a SNP interfering with the ligation efficiency of the MLPA reaction.

To search, in the remaining patients, for additional exon 1 deletions not detectable by our PCR reaction, multiplex ligation-dependent probe amplification (MLPA) (5) was performed in all four exons and detected a hemizygous deletion of exon 1 in one patient (Patient V2; FIG. 3). Finally, an additional patient with an MLPA-detected deletion restricted to exon 1 was recently documented in abstract form, though the effect on MECP2E1 was not realized (S. Boulanger et al. Am J Hum Genet 73, 572 (2003)).

In contrast, no mutation specific to the MeCP2E2-defining exon 2 has been found to date despite several hundred patients analyzed for mutations in this exon (31 publications; most reviewed in ref. 3). These studies did not include exon 1 as it was considered non-coding.

Exon 1 deletions result in absent or truncated MeCP2E1 proteins. However, they also result in shortening of MECP2E2's 5'UTR and may possibly affect its expression. This possibility was tested in patient V1 by RT-PCR on whole blood. No diminution of MECP2E2 expression was present (FIG. 2c). In conclusion, mutation data indicate that inactivation of MeCP2E1 is sufficient in RTT, but the same cannot be said, to date, of MeCP2E2.

Materials and Methods

PCR, manual sequencing, cloning, rtPCR, gel blotting. PCR amplification was performed using [NH$_4$]$_2$SO$_4$-containing PCR buffer (MBI Fermentas) with 1M betaine, 200 µM dNTPs including 50% deaza dGTP, with a 95° C. denaturing step for 3 minutes, followed by cycling at 95° C. for 30 secs, 55° C. for 30 secs, 72° C. for 45 secs for 30 cycles, followed by a 7 minute soak step at 72° C. Manual sequencing was performed, following extraction from a 1% agarose gel, using the Thermosequenase™ kit (USB/Amersham) and run on a 6% denaturing polyacrylamide gel for 3 hours. PCR products were cloned using the pDRIVE vector (Qiagen PCR cloning kit). Whole blood RNA was extracted using the PAXgene Blood RNA Kit (Qiagen). Reverse transcription was performed with random hexamers and a standard Superscript III protocol (Invitrogen). Human brain subregion cDNA was obtained from OriGene. The polyacrylamide gel in (FIG. 2c) was blotted onto Hybond N+ (Amersham) and hybridized with primer HF labeled at the 3' end with [α$^{32}$P]-dCTP using deoxynucleotidyl transferase (MBI Fermentas).

Figure 4:
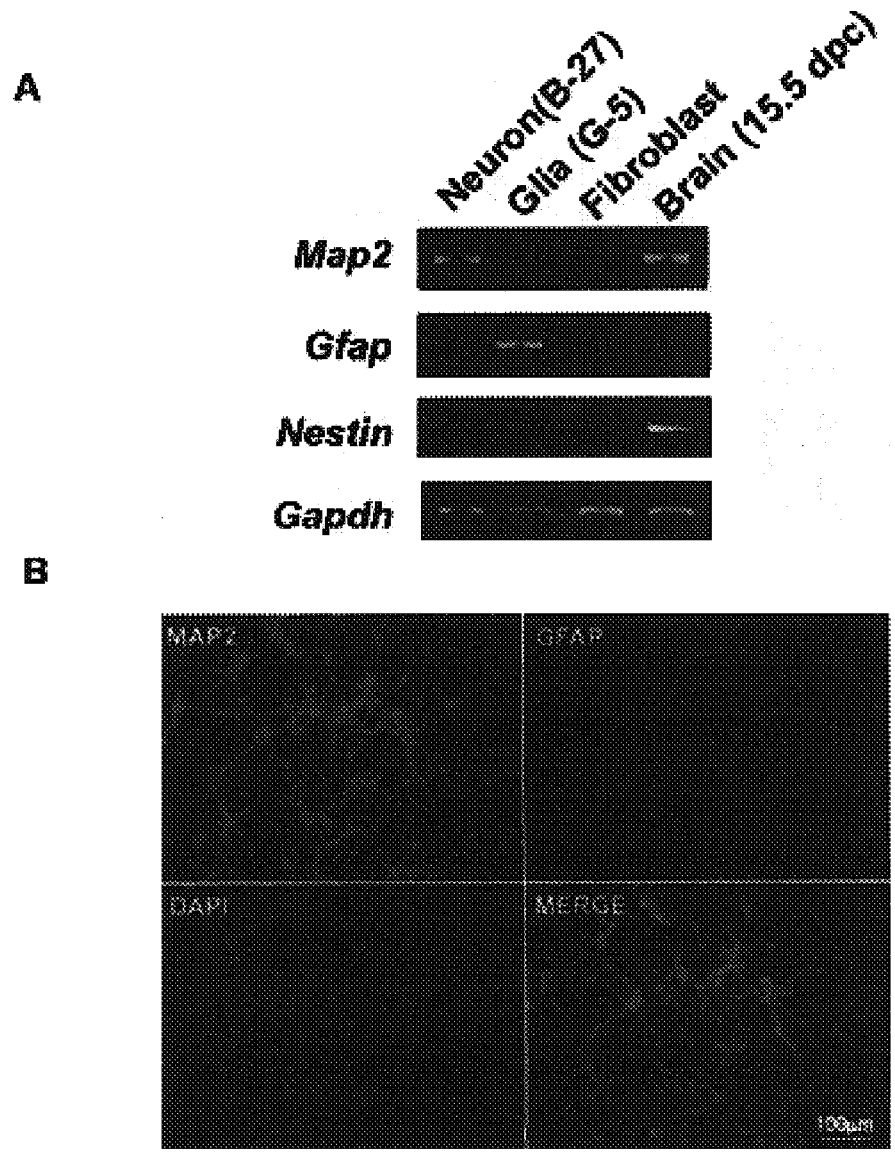
FIG. 4 shows the characterization of the primary brain cell cultures by rtPCRR (A) and IF (B). (A) Map2, Gfap and Nestin expressions indicate that the cultures in B-27 medium were composed primarily of neurons and those in G-5 medium were glial cells. Fibroblasts from the same embryos were also cultured and used as negative controls. Whole brain tissue (15.5 dpc) was used as a positive control for Map2 and Nestin. (B) Double staining for neurons was performed with mouse anti-MAP2 and rabbit anti-GFAP antibodies. They were also counterstained with DAPI (blue). Most of the cells are neurons, which stained positively for MAP2 (green), and an insignificant percentage of contamination with glial cells stained positively for GFAP (red) was detected.
Figure 5:
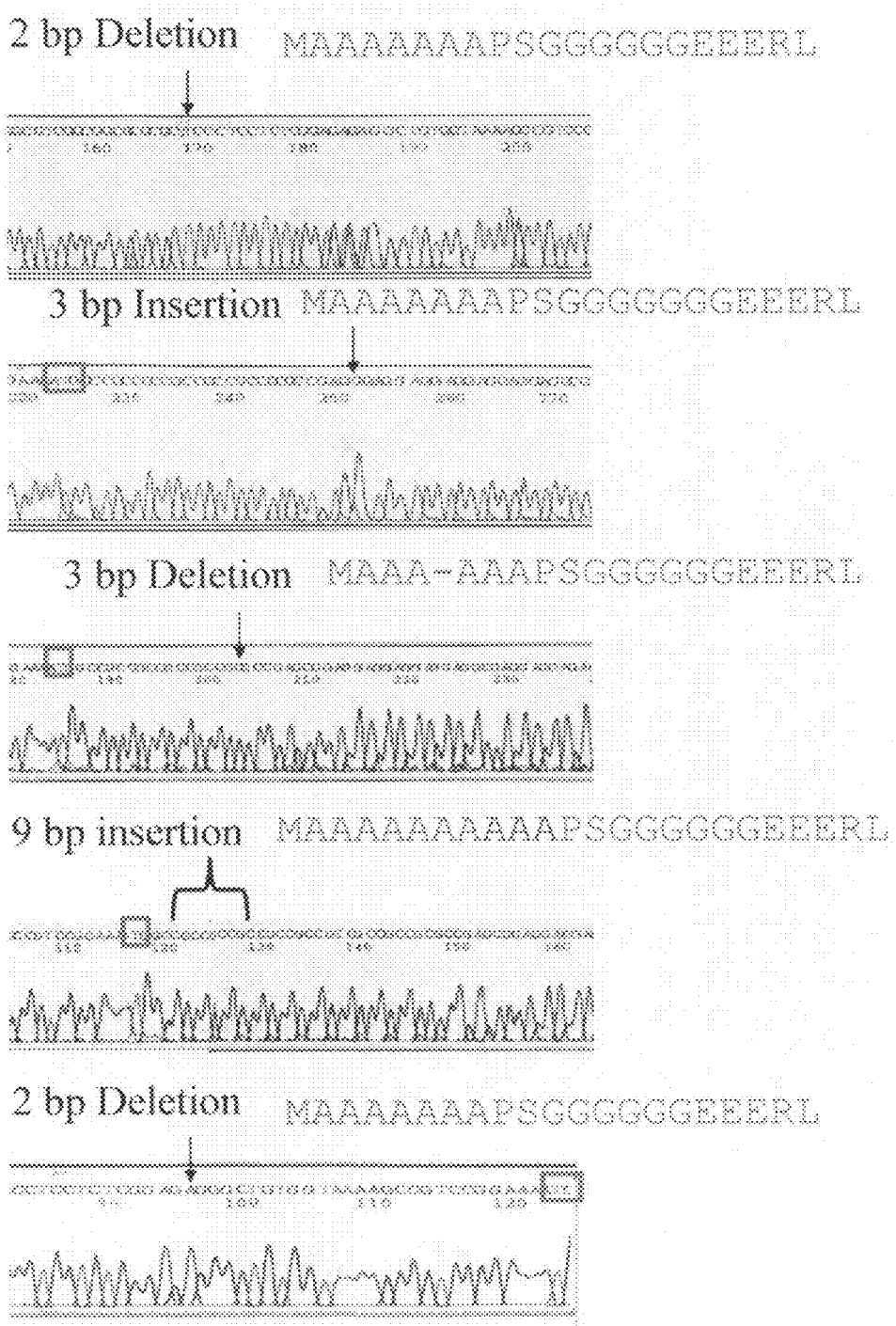
FIG. 5 shows the nucleotide sequence of the five MECP2 exon 1 variants identified in female MR patients. All sequences were obtained from single colonies, after cloning the heterozygious PCR product into the pDRIVE vector (Qiagen). The ATG start codon is indicated by a red box, where possible. The resulting amino acid sequence is also indicated, with wild type sequence shown in red, and changes indicated in green type.

Preparation of neuronal and glial cultures. Cerebral cortices were prepared from 15.5 days postcoitum (15.5 dpc) embryos of CD-1 mice. The procedure of Yamasaki et al. (Yamasaki et al. Hum Mol Genet 12: 837-847, 2003) was used. Briefly, fetal cerebral cortices without meninges were dissociated by mechanical trituration and digested with 0.25% trypsin with EDTA. After adding fetal bovine serum (FBS; GIBCO BRL), filtered cells were collected by centrifugation. The cell pellet was resuspended in Neurobasal (GIBCO BRL) medium supplemented with B-27 (GIBCO BRL) for growth of neurons or with G-5 (GIBCO BRL) for growth of glial cells. Cells were plated on polyethyleneimine-coated plastic dishes at a density of 2×10$^6$ cells/ml. Cultures of neurons and glial cells were maintained in 5% CO$_2$ at 37° C. for 6 days and 12 days, respectively. Isolated brain cells were characterized by RT-PCR and immunofluorescence (IF) using the markers MAP2 (microtubule-associated protein 2) for neurons, GFAP (glial fibrillary acidic protein) for glial cells and NESTIN for progenitor cells. For IF, the following specific antibodies were used: mouse monoclonal anti-MAP2 (CHEMICON), and rabbit polyclonal anti-GFAP (DAKO). The primers used for rtPCR were same as Yamasaki et al. To obtain a semi-quantitative PCR, optimal cDNA concentration and number of cycles were determined according to Gapdh amplification as an internal control. FIG. 4 shows the characterization of the primary brain cell cultures by rtPCR (A) and IF (B).

Quantitative rtPCR. To determine the quantity of the MECP2 transcripts in different tissues, we developed transcript-specific real-time quantitative PCR assays using SYBR Green detection method (PE Applied Biosystems, ABI PRISM 7900 Sequence Detection System). The following MECP2E2-specific forward primer (25 nM) (in exon 2) was designed: 5'-ctcaccagttcctgctttgatgt-3' (SEQ ID No. 12). The MECP2E1-specific primer (25 nM) was placed at the junction of exons 1 and 3: 5'-aggagagactggaagaaaagtc-3' (SEQ ID No. 10). Both assays used the same reverse primer (25 nM) in exon 3: 5'-cttgaggggtttgtccttga-3' (SEQ ID No. 11), producing fragments of 161-(MECP2E2) and 65-bp (MECP2E1). The corresponding transcript-specific primers (25 nM) for the mouse mecp2 transcripts (mecp2e2 167 bp and mecp2e1 71 bp) were 5'-ctcaccagttcctgctttgatgt-3' (SEQ ID No. 12) (MECP2E2); 5'-aggagagactggaggaaaagtc-3' (SEQ ID No. 13) (MECP2E1) and the common reverse primer 5'-cttaaact-tcagtggcttgtctctg-3' (SEQ ID No. 14). PCR conditions were: 2 min 50C, 10 min 95C and 40 cycles of 15 sec 95C, 85 s 60C. The PCR reactions were performed in separate tubes; and absolute quantitation of the MECP2E2 and E1 transcripts was performed from cDNA from human adult brain, cerebellum, fibroblast and lymphoblast (Clontech, Palo Alto, USA), as well as from murine neuronal and glial cell cultures (see above). Results were analyzed using the standard curve method according to the manufacturer's instructions (PE Applied Biosystems, ABI PRISM 7900 Sequence Detection System). The standard curve was developed using dilutions of the transcript-specific purified PCR products.

Immunofluorescence light microscopy. 3'-myc-tagged MECP2E2 and MECP2E1 constructs (pcDNA3.1A-MECP2E2-myc and pcDNA3.1A-MECP2E1-myc) were generated by PCR amplification of full-length cDNA of each transcript with BamHI (5') and XbaI (3') restriction sites attached and subsequent cloning in-frame with myc into pcDNA3.1 version A (Invitrogen). The forward primer for MECP2E2 contained the start codon in exon 2 (5'-tatggatc-cATGgtagctgggat-3') (SEQ ID No. 15), while the forward primer for MECP2E1 included the start codon in exon1 (5'-tatggatccggaaaATGgccg-3') (SEQ ID No. 16) (BamHI restriction site underlined, start codon uppercase). The reverse primer was the same for both amplifications (5'-gcgtctagagctaactctct-3') (SEQ ID No. 17) (XbaI restriction site underlined). The template used for PCR was small intestine cDNA for MECP2E2 and skeletal muscle cDNA for MECP2E1. pcDNA3.1A-MECP2E2-myc and pcDNA3.1A-MECP2E1-myc (2 ug) were transfected into COS-7 cells using lipofectamine (Invitrogen) and the lipid-DNA complex was exposed in DMEM (GIBCO) for 5 hours. Forty-eight hours post-transfection the cultures were rinsed in PBS and fixed for 15 min at −20° C. in an acetone:methanol (1:1) mix, blocked for 1 hour (10% BSA in PBS) and incubated with anti-myc (Santa Cruz Biotechnology, 1:50 in blocking buffer) for 45 min at room temperature. After washing with PBS, slides were incubated with secondary antibody (FITC-labeled goat anti-mouse (Jackson Immunoresearch labs), 1:400, detectable through the green filter) in blocking solution, mounted with Dako Anti-Fade and analyzed by immunofluorescence light microscopy.

MLPA analysis. MLPA was performed as described by Schouten et al., supra and as described by Schouten, supra. MECP2 test kits from MRC-Holland, Amsterdam, Netherlands (www.mrc-holland.com) were utilized and consisted of 20 probe pairs that target the four MECP2 exons, six X-linked control regions and ten autosomal control regions. Briefly, 100-200 ng of genomic DNA was denatured and hybridized with the probe mix overnight at 60° C. The following morning the paired probes were ligated using heat stable Ligase-65 at 54° C. for 15 minutes. The ligation was followed with PCR with a common primer pair that hybridizes to the terminal end of each ligation product. One PCR primer was FAM-labeled and conditions for the PCR were as follows: 95° C. 30s, 60° C. 30s and 72° 1 min. The resulting amplicons were analyzed on an ABI 3100 capillary electrophoresis instrument and ABI Genescan software. All data management and comparisons to normal controls were done with Excel software.

Discussion

Recently, studies in frog (*Xenopus laevis*) afforded important insight into the role of MeCP2 in neurodevelopmental transcription regulation. MeCP2 was shown to be a component of the SMRT complex involved in the regulation of genes involved in neuronal differentiation following developmental stage-specific mediation by Notch-Delta[9]. The frog Mecp2 transcript targeted for silencing in these experiments is an orthologue of MECP2E1 (FIG. 1f). In fact, MeCP2E1 appears to be the only form of MeCP2 in non-mammalian vertebrates (FIG. 1f).

The new MeCP2 N-terminus is a distinctive 21 amino acid peptide including polyalanine and polyglycine tracts (MAAAAAAAPSGGGGGGEEERL) (SEQ ID No. 18) (FIG. 1f). A similar N-terminus occurs in the ERK1 (MAPK3) extracellular signal-regulated kinase (FIG. 1f), a key common component of multiple signal transduction pathways. Intriguingly, in neurons, both ERK1[10] and MeCP2[11] have been shown to be present in the post-synaptic compartment, in addition to the nucleus, and the former shown to translocate between the two compartments to link synaptic activity to transcriptional regulation[10]. It is possible that MeCP2E1 similarly links synaptic function, in this case neurodevelopmental synaptic contact guidance, with transcriptional regulation. The only other proteins in which consecutive polyalanine and polyglycine tracts are found are in some members[12] of the homeobox (HOX) family. These, like MeCP2, are developmental transcription regulators.

Finally, non-inactivating MECP2 mutations have been associated with phenotypes that overlap RTT such as mental retardation and autism[13]. The MeCP2 variant discovered in this study is a candidate for involvement in these disorders.

Example 4

Mutations in MECP2E1 in Mental Retardation

The inventors screened the MECP2E1 gene in N=401 autism probands, and in N=493 patients with non-specific mental retardation. Autism probands recruited through the Hospital for Sick Children in Toronto (N=146; 114 male, 32 female) and from London, UK (N=13; 10 male, 3 female) were also screened, as well as probands from multiplex families from the Autism Genetic Resource Exchange (AGRE; N=242; 100 female, 142 male). Local institutional ethics board approval was obtained, and written consent given by participants. Anonymized DNA samples were also obtained for 293 female and 200 male patients with non-specific developmental delay/mental retardation who had been referred for fragile-X testing (but tested negative) to the Department of Pediatric Laboratory Medicine at the Hospital for Sick Children. Polymerase chain reaction followed by denaturing high performance liquid chromatography (DHPLC) was used for mutation detection, with PCR primers and conditions as described previously in Example 3. PCR product from female individuals suspected of carrying a sequence variant was cloned into the pDRIVE vector (Qiagen), and at least four clones sequenced using automated BIGDYE™ sequencing (ABI 3100) in forward and reverse directions. PCR products from males were excised from agarose gel, column purified, then sequenced, also using automated BIGDYE™ sequencing (ABI 3100) in both forward and reverse directions. No mutations were identified among the autism screening set, however sequence variants were identified among eight of the female MR cases (see FIG. 7), three of which result in insertion or deletion of amino acids within the polyalanine repeat stretch, and two of which result in insertion of a glycine residue within the polyglycine repeat at the N-terminal portion of MECP2E1. The first individual identified was heterozygous for a deletion of a GpC dinucleotide positioned 45-46 bp upstream of the putative MECP2E1 start codon. This deletion could disrupt a potential SP1 transcription factor binding site (as predicted using AliBaba2.1 at www.gene-regulation.com/pub/programs/alibaba2/index.html), and may also eliminate potentially methylatable cytosine residues. Another individual is heterozygous for an ApG dinucleotide deletion 26 bp upstream of the MECP2E1 start codon. Two individuals are heterozygous for a GGA trinucleotide insertion within a poly[GGA] stretch, which would result in an additional glycine residue within the predicted polyglycine stretch. A fifth individual is heterozygous for a GCC trinucleotide deletion within a triplet repeat stretch encoding polyalanine. Two individuals are heterozygous for a 9 bp insertion, also within the GCC trinucleotide repeat/polyalanine region, and would result in the polyalanine stretch being extended from seven to ten residues.

The amino acid sequence variation in ~2% of female non-specific MR cases in a new isoform of a protein that has previously been associated with a mental retardation syndrome, is extremely intriguing. Moreover, the fact that the variation occurs within a part of the protein that is conserved across many vertebrate species also adds to the interest (100% identity to chimpanzee, orang-utan, macaque, cat and dog MeCP2E1 amino acid sequence). It would be particularly useful to know whether there are any specific phenotypic features among the individuals with the variants, how severe the symptoms are an whether there are overlaps with or distinctions from the Rett syndrome phenotypes. However, since the DNAs were anonymized, it is not possible, in this instance, to correlate the mutations discovered with phenotypic features or severity. In an attempt to address this issue, a second sample set of MR cases (188 female and 96 male) from the Greenwood Genetic Center, South Carolina, were screened, followed by sequencing. No variants were found in the males, and two of the females carried the GGA insertion encoding an extra glycine residue.

In the present study, three female MR patients were identified with a 3 bp insertion leading to an extra glycine residue within the polyglycine stretch at the N-terminal end of MeCP2E1. No disease association has previously been reported with expansion within a glycine repeat. The function of polyglycine stretches, either within the context of the MeCP2E1 protein or more generally, is not known, although a study of the Toc75 protein in plants suggests that a polyglycine stretch in the protein is essential for correct targeting of the protein to the chloroplast outer envelope. A similar function of protein trafficking may also be the case for mammalian proteins with polyglycine stretches, and for MeCP2E1.

The variants within the polyalanine tracts are of particular interest, as they are rarely polymorphic, and because a number of small expansions (or duplications) within such tracts have been reported to cause diseases, ranging from cleidocranial dysplasia (RUNX2), oculopharyngeal muscular dystrophy (PABPN1) and mental retardation (ARX; this gene is also X-chromosomal and has a very broad array of phenotypes—see above). The majority of polyalanine disease genes encode transcription factors, although PABPN1 gene encodes a polyadenylate binding protein. On the one hand, amongst these diseases, the smallest pathogenic repeats within the transcription factor genes are generally greater than 20 alanines in length, thus it could be considered improbable that a stretch of alanines as short as that encoded by MECP2E1 could be pathogenic, and a change of 1 or 3 alanine residues could be considered likely to be rare polymorphisms. There is currently some uncertainty as to whether small expansion of 1 or 3 alanine residues within the ARX gene may be pathogenic or innocent variants. On the other hand, oculopharyngeal muscular dystrophy is caused by mutations within a GCG tract in the PABPN1 gene, that expand a polyalanine tract from just 10 alanine residues to between 12 and 17 alanine residues. Moreover, as with the polyalanine tract in MeCP2E1, the polyalanine tract in PABPN1 is right at the N-terminal end of the gene, and thus it is possible that smaller mutations within repeat stretches within the N-terminal portion of a protein may be more detrimental than larger mutations located in the central portions of proteins.

A recently published study screened for mutations in MECP2 exon 1 among 97 Rett patients with no mutation in exons 2, 3 or 4, and among 146 controls (18). One of the Rett patients was found to have a 6 bp insertion within the polyalanine-encoding [GCC] stretch, but no such variations were observed among the controls. The variant was inherited from an unaffected mother, and it was concluded that the variant is thus unlikely to be etiologically relevant (18). However, it has also been demonstrated recently that even subtle changes in expression of MECP2 in mice can have profound neurological and behavioural consequences (19). It is apparent that patients with the same MECP2 mutation may have very different phenotypic features and severity, and it is likely that variation in X-inactivation pattern plays a role in this discordancy. Thus it is quite feasible that variation in exon 1, either within the repeat stretches resulting in change in length of polyalanine or polyglycine stretch, or in the region just upstream of the start codon, may affect function or expression levels resulting in a neuropathological phenotype.

Example 5

Additional Mutations in MECP2E1 in Rett's Syndrome

The entire coding regions of exons 1,2,3 and 4 and their intronic flanking sequences were analyzed. Exons 2 to 4 were amplified by PCR with primer pairs designed with the use of genomic sequence information from the Human Genome Project working draft site (UCSC, www.genome.ucsc.edu) and the Lasergene Primer select program. The PCR products were loaded on 2% agarose gel to confirm amplification before analysis for base changes by dHPLC (WAVE Nucleic Acid Fragment Analysis System from Transgenomic, San Jose, Calif.). Solvent A consisted of 0.1 mol/L triethylammonim acetate (TEAA) and 25% acetonitrile and solvent B contained 1M TEAA, 25% acenonitril. PCR products showing a chromatographic variation on dHPLC were sequenced directly on an automatic sequencer (Gene Reader 4200). The sequencing data was analyzed using DNA Star software Seq-Man (Lasergene). Exon 1 was PCR amplified and sequenced in all patients as recently described.

The first exon 1 mutation consists of two missing base pairs at the exon 1 intron 1 boundary. Because of the nature of the sequence in this region, we cannot resolve whether the missing two nucleotides are the first two base pairs of intron 1 (GT) or the last nucleotide of exon 1 (T) and the first nucleotide of intron 1 (G). In either case, the missing pair of nucleotides destroys the predicted consensus splice site and results in readthrough of intron 1 (data not shown). In the second patient with an exon 1 mutation a 1A→T substitution (ATG->TTG) changes the first Methionine codon into a Leucine. The prediction is that MECP2E1 translation would be greatly or totally hindered due to absence of a start codon. MECP2E2 would be normally made (and appears unable to rescue the disease phenotype).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

MECP2E1 mutations or variants identified to date. "del" indicates a deletion; "ins" indicates an insertion

| Nucleotide change | Position relative to NM_004992 (SEQ ID No. 1) | Amino acid change | Effect of change | Associated phenotype | Number of Patients with mutation |
|---|---|---|---|---|---|
| 11bp deletion | Between 38 to 54 | Frameshift leads to nonsense mutation, premature truncation of protein after amino acid 36 | MECP2E1 disrupted, MECP2E2 not disrupted | Rett | 1 |
| Exon 1 deletion | 1-69 | No MECP2E1 translation | MECP2E1 and MECP2E2 disrupted | Rett | 1 |
| 1A->T | 8 | 1Met->Leu | MECP2E1 disrupted, MECP2E2 possibly diminished | Rett | 1 |
| del[TG] | 69 to 70 | Destroys exon1/intron 1 splice site, resulting in read through and nonsense translation, with truncation after amino acid 97 | MECP2E1 disrupted, MECP2E2 probably not disrupted | Rett | 1 |
| ins[GCCGCCGCC] | Between nt 11 and 29 | ins[Ala]3 within N terminal polyalanine stretch of MECP2E1 | May affect function and or translation of MECP2E1, but not MECP2E2 | Developmental Delay | 2 |

TABLE 1-continued

MECP2E1 mutations or variants identified to date. "del" indicates a deletion; "ins" indicates an insertion

| Nucleotide change | Position relative to NM_004992 (SEQ ID No. 1) | Amino acid change | Effect of change | Associated phenotype | Number of Patients with mutation |
|---|---|---|---|---|---|
| del[GCC] | Between nt 11 and 29 | del Ala within N terminal polyalanine stretch of MECP2E1 | May affect function and or translation of MECP2E1, but not MECP2E2 | Developmental Delay | 1 |
| ins[GGA] | Between 38 to 54 | ins Gly | May affect function and or translation of MECP2E1, but not MECP2E2 | Developmental Delay | 5 |
| −45 del [GC] | −38 to −39 relative to BX538060 | In 5'UTR, 45 nt upstream of START codon-potential SP1 transcription factor binding site | May affect transcription or translation of MECP2E1 | Developmental Delay | 1 |
| −26 del [AG] | −19 to −20 relative to BX538060 | In 5'UTR, 26 nt upstream of START codon | May affect transcription or translation of MECP2E1 | Developmental Delay | 1 |

---

We claim:

1. A method of detecting Rett syndrome that is associated with a mutation or deletion in the human MECP2 gene comprising detecting the presence of a non-sense or frameshift mutation or a deletion within exon 1, or in the intron-exon boundary immediately adjacent to exon 1, of a nucleic acid sequence encoding the MeCP2E1 protein having the amino acid sequence of SEQ ID NO: 4 in a sample obtained from a human, wherein the sample nucleic acid sequence is compared to a control nucleic acid sequence and wherein the presence of a mutation or deletion in exon 1, or in the intron-exon boundary immediately adjacent to exon 1, of the sample nucleic acid sequence indicates that the human has Rett syndrome, wherein the mutation or deletion detected is selected from the group consisting of: (1) a deletion of 11 consecutive base pairs in nucleotides 38 to 54 of SEQ ID NO: 1, said deletion causing a truncation of the MeCP2E1 protein of SEQ ID NO: 4 after amino acid 36; (2) a deletion consisting of nucleotides 1-69 of exon 1 of SEQ ID NO: 1; (3) an adenine to thymine change at nucleotide position 8 of SEQ ID NO: 1; and (4) a deletion of a T, G or TG between nucleotide positions 69-71 of SEQ ID NO: 1.

2. The method according to claim 1 comprising:
   a) amplifying the nucleic acid sequence in the sample with primers X1F (5'-CCATCACAGCCAATGACG-3') (SEQ ID No. 19) and X1R (5'-AGGGGGAGGGTA-GAGAGGAG-3') (SEQ ID No. 20) in a polymerase chain reaction;
   b) amplifying the nucleic acid sequence from the control with the same primers;
   c) sequencing the amplified sequences; and
   d) comparing the sample sequence to the control sequence.

3. The method according to claim 1 wherein the MECP2 gene comprises the nucleic acid sequence SEQ ID NO: 1.

4. The method according to claim 3 wherein the presence of the mutation or deletion in the MECP2E1 transcript of the MECP2 gene comprising SEQ ID NO.: 1, wherein the MECP2E1 transcript comprises SEQ ID NO:3, is detected by performing multiplex ligation-dependent probe amplification in all four exons of the MECP2 gene sequence of SEQ ID NO.: 1.

5. A method of detecting the presence of a mutation or deletion in a nucleic acid molecule encoding the MeCP2E1 protein comprising:
   a) analyzing a test sample containing a nucleic acid sequence encoding the MeCP2E1 protein consisting of SEQ ID NO.: 4 for a mutation or deletion within exon 1, or in the intron-exon boundary immediately adjacent to exon 1, of said nucleic acid sequence; and
   b) comparing the results of the analysis of the test sample with the results of analysis of a control sample,
wherein the control sample comprises the nucleic acid encoding the MeCP2E1 protein consisting of SEQ ID NO.: 4 without a mutation or deletion within exon 1, or in the intron-exon boundary immediately adjacent to exon 1.

6. The method according to claim 5 wherein the nucleic acid molecule encoding the MeCP2E1 protein comprises SEQ ID NO: 3.

7. The method according to claim 5 wherein the mutation or deletion being detected in SEQ ID NO: 1 is selected from the group consisting of: (1) a deletion of 11 consecutive base pairs in nucleotides 38 to 54 of SEQ ID NO: 1, said deletion causing a truncation of the MeCP2E1 protein of SEQ ID NO: 4 after amino acid 36; (2) a deletion consisting of nucleotides 1-69 of exon 1 of SEQ ID NO: 1; (3) an adenine to thymine change at nucleotide position 8 of SEQ ID NO: 1; and (4) a deletion of a T, G or TG between nucleotide positions 69-71 of SEQ ID NO: 1.

8. A method of detecting Rett Syndrome that is associated with a mutation or deletion in the human MECP2E1 gene comprising: a) analyzing a nucleic acid sample obtained from a human for the presence or absence of a mutation or deletion in exon 1 or in the intron-exon boundary immediately adjacent to exon 1 of the MECP2E1 transcript of the MECP2 gene comprising SEQ ID NO: 1; and b) comparing the results of step a) with results of analysis of a control nucleic acid sample, wherein the detection of a mutation or deletion selected from the group consisting of: (1) a deletion of 11 consecutive base pairs in nucleotides 38 to 54 of SEQ ID NO: 1, said deletion causing a truncation of the MeCP2E1 protein of SEQ ID NO.: 4 after amino acid 36; (2) a deletion consisting of nucleotides 1-69 of exon 1 of SEQ ID NO: 1; (3) an adenine to thymine change at nucleotide position 8 of SEQ ID NO: 1; and (4) a deletion of a T, or TG between nucleotide positions 69-71 of SEQ ID NO: 1 indicates that the human has Rett syndrome.

9. The method of claim 1 wherein the nucleic acids are extracted from a cell sample prior to analysis.

10. The method of claim 1 wherein the nucleic acids in the samples are amplified prior to analysis.

11. The method of claim 8 wherein the nucleic acids are extracted from a cell sample prior to analysis.

12. The method of claim 8 wherein the nucleic acids in the samples are amplified prior to analysis.

* * * * *

SEQUENCE LISTING

```
<160> NUMBER OF SEQ ID NOS: 29

<210> SEQ ID NO 1
<211> LENGTH: 10182
<212> TYPE: DNA
<213> ORGANISM: Homo sapiens

<400> SEQUENCE: 1
ccggaaaatg gccgccgccg ccgccgccgc gccgagcgga ggaggaggag gaggcgagga      60
ggagagactg ctccataaaa atacagactc accagttcct gctttgatgt gacatgtgac     120
tccccagaat acaccttgct tctgtagacc agctccaaca ggattccatg gtagctggga     180
tgttagggct cagggaagaa aagtcagaag accaggacct ccaggcctc aaggacaaac      240 ccctcaagtt taaaaaggtg aagaaagata agaaagaaga gaaagagggc aagcatgagc     300
ccgtgcagcc atcagcccac cactctgctg agcccgcaga ggcaggcaaa gcagagacat     360
cagaagggtc aggctccgcc ccggctgtgc cggaagcttc tgcctccccc aaacagcggc     420
gctccatcat ccgtgaccgg ggacccatgt atgatgaccc caccctgcct gaaggctgga     480
cacggaagct taagcaaagg aaatctggcc gctctgctgg aagtatgat gtgtatttga      540 tcaatcccca gggaaaagcc tttcgctcta aagtggagtt gattgcgtac ttcgaaaagg     600
taggcgacac atccctggac cctaatgatt ttgacttcac ggtaactggg agagggagcc     660
cctcccggcg agagcagaaa ccacctaaga agcccaaatc tcccaaagct ccaggaactg     720
gcagaggccg gggacgcccc aaagggagcg gcaccacgag acccaaggcg ccacgtcag      780 agggtgtgca ggtgaaaagg gtcctggaga aaagtcctgg gaagctcctt gtcaagatgc     840
cttttcaaac ttcgccaggg ggcaaggctg agggggtgg ggccaccaca tccacccagg      900
tcatggtgat caaacgcccc ggcaggaagc gaaagctga ggccgaccct caggccattc      960
ccaagaaacg gggccgaaag ccgggggagtg tggtggcagc cgctgccgcc gaggccaaaa    1020
```

```
agaaagccgt gaaggagtct tctatccgat ctgtgcagga gaccgtactc cccatcaaga    1080
agcgcaagac ccgggagacg gtcagcatcg aggtcaagga agtggtgaag cccctgctgg    1140
tgtccaccct cggtgagaag agcgggaaag gactgaagac ctgtaagagc cctgggcgga    1200
aaagcaagga gagcagcccc aagggcgca gcagcagcgc ctcctcaccc cccaagaagg     1260
agcaccacca ccatcaccac cactcagagt ccccaaaggc ccccgtgcca ctgctcccac    1320
ccctgccccc acctccacct gagcccgaga gctccgagga ccccaccagc ccccctgagc    1380
cccaggactt gagcagcagc gtctgcaaag aggagaagat gcccagagga ggctcactgg    1440
agagcgacgg ctgccccaag gagccagcta agactcagcc cgcggttgcc accgccgcca    1500
cggccgcaga aaagtacaaa caccgagggg agggagagcg caaagacatt gtttcatcct    1560
ccatgccaag gccaaacaga gaggagcctg tggacagccg gacgcccgtg accgagagag    1620
ttagctgact ttacacggag cggattgcaa agcaaaccaa caagaataaa ggcagctgtt    1680
gtctcttctc cttatgggta gggctctgac aaagcttccc gattaactga aataaaaaat    1740
attttttttt ctttcagtaa acttagagtt tcgtggcttc agggtgggag tagttggagc    1800
attggggatg ttttcttac cgacaagcac agtcaggttg aagacctaac cagggccaga    1860
agtagctttg cactttccta aactaggctc cttcaacaag gcttgctgca gatactactg    1920
accagacaag ctgttgacca ggcacctccc ctcccgccca aacctttccc ccatgtggtc    1980
gttagagaca gagcgacaga gcagttgaga ggacactccc gttttcggtg ccatcagtgc    2040
cccgtctaca gctcccccag ctcccccac ctccccact cccaaccacg ttgggacagg      2100
gaggtgtgag gcaggagaga cagttggatt ctttagagaa gatggatatg accagtggct    2160
atggcctgtg cgatcccacc cgtggtggct caagtctggc cccacaccag ccccaatcca    2220
aaactggcaa ggacgcttca caggacagga aagtggcacc tgtctgctcc agctctggca    2280
tggctaggag gggggagtcc cttgaactac tgggtgtaga ctggcctgaa ccacaggaga    2340
ggatggccca gggtgaggtg gcatggtcca ttctcaaggg acgtcctcca acgggtggcg    2400
ctagaggcca tggaggcagt aggacaaggt gcaggcaggc tggcctgggg tcaggccggg    2460
cagagcacag cggggtgaga gggattccta atcactcaga gcagtctgtg acttagtgga    2520
caggggaggg ggcaaagggg gaggagaaga aaatgttctt ccagttactt tccaattctc    2580
ctttagggac agcttagaat tatttgcact attgagtctt catgttccca cttcaaaaca    2640
aacagatgct ctgagagcaa actggcttga attggtgaca tttagtccct caagccacca    2700
gatgtgacag tgttgagaac tacctggatt tgtatatata cctgcgcttg ttttaaagtg    2760
ggctcagcac atagggttcc cacgaagctc cgaaactcta agtgtttgct gcaatttat     2820
aaggacttcc tgattggttt ctcttctccc cttccatttc tgccttttgt tcatttcatc    2880
ctttcacttc tttcccttcc tccgtcctcc tccttcctag ttcatccctt ctcttccagg    2940
cagccgcggt gcccaaccac acttgtcggc tccagtcccc agaactctgc ctgccctttg    3000
tcctcctgct gccagtacca gccccaccct gttttgagcc ctgaggaggc cttgggctct    3060
gctgagtccg acctggcctg tctgtgaaga gcaagagagc agcaaggtct tgctctccta    3120
ggtagccccc tcttccctgg taagaaaaag caaaaggcat ttcccaccct gaacaacgag    3180
ccttttcacc cttctactct agagaagtgg actggaggag ctgggcccga tttggtagtt    3240
gaggaaagca cagaggcctc ctgtggcctg ccagtcatcg agtggcccaa caggggctcc    3300
atgccagccg accttgacct cactcagaag tccagagtct agcgtagtgc agcagggcag    3360
tagcggtacc aatgcagaac tcccaagacc cgagctggga ccagtacctg ggtccccagc    3420
```

-continued

```
ccttcctctg ctcccccttt tccctcggag ttcttcttga atggcaatgt tttgcttttg    3480
ctcgatgcag acaggggggcc agaacaccac acatttcact gtctgtctgg tccatagctg    3540
tggtgtaggg gcttagaggc atgggcttgc tgtgggtttt taattgatca gttttcatgt    3600
gggatcccat ctttttaacc tctgttcagg aagtccttat ctagctgcat atcttcatca    3660
tattggtata tccttttctg tgtttacaga gatgtctctt atatctaaat ctgtccaact    3720
gagaagtacc ttatcaaagt agcaaatgag acagcagtct tatgcttcca gaaacaccca    3780
caggcatgtc ccatgtgagc tgctgccatg aactgtcaag tgtgtgttgt cttgtgtatt    3840
tcagttattg tccctggctt ccttactatg gtgtaatcat gaaggagtga aacatcatag    3900
aaactgtcta gcacttcctt gccagtcttt agtgatcagg aaccatagtt gacagttcca    3960
atcagtagct taagaaaaaa ccgtgtttgt ctcttctgga atggttagaa gtgagggagt    4020
ttgccccgtt ctgtttgtag agtctcatag ttggactttc tagcatatat gtgtccattt    4080
ccttatgctg taaaagcaag tcctgcaacc aaactcccat cagcccaatc cctgatccct    4140
gatcccttcc acctgctctg ctgatgaccc cccagcttc acttctgact cttccccagg     4200
aagggaaggg gggtcagaag agagggtgag tcctccagaa ctcttcctcc aaggacagaa    4260
ggctcctgcc cccatagtgg cctcgaactc ctggcactac caaaggacac ttatccacga    4320
gagcgcagca tccgaccagg ttgtcactga aaagatgttt attttggtca gttgggtttt    4380
tatgtattat acttagtcaa atgtaatgtg gcttctggaa tcattgtcca gagctgcttc    4440
cccgtcacct gggcgtcatc tggtcctggt aagaggagtg cgtggcccac caggcccccc    4500
tgtcacccat gacagttcat tcagggccga tggggcagtc gtggttggga acacagcatt    4560
tcaagcgtca ctttatttca ttcgggcccc acctgcagct ccctcaaaga ggcagttgcc    4620
cagcctcttt cccttccagt ttattccaga gctgccagtg gggcctgagg ctccttaggg    4680
ttttctctct atttcccccct ttcttcctca ttccctcgtc tttcccaaag gcatcacgag    4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta    4860
agctgcagga ttctcaccag ctgtgtccgg cccagttttg gggtgtgacc tcaatttcaa    4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt    5100
cgtcgagctc ccccaggtc tacccctccc ggccctgcct gctggtgggc ttgtcatagc      5160
cagtgggatt gccggtcttg acagctcagt gagctggaga tacttggtca cagccaggcg    5220
ctagcacagc tcccttctgt tgatgctgta ttcccatatc aaaagacaca ggggacaccc    5280
agaaacgcca catcccccaa tccatcagtg ccaaactagc caacgccccc agcttctcag    5340
ctcgctggat ggcggaagct gctactcgtg agcgccagtg cgggtgcaga caatcttctg    5400
ttgggtggca tcattccagg cccgaagcat gaacagtgca cctgggacag ggagcagccc    5460
caaattgtca cctgcttctc tgcccagctt ttcattgctg tgacagtgat ggcgaaagag    5520
ggtaataacc agacacaaac tgccaagttg ggtggagaaa ggagtttctt tagctgacag    5580
aatctctgaa ttttaaatca cttagtaagc ggctcaagcc caggagggag cagagggata    5640
cgagcggagt cccctgcgcg ggaccatctg gaattggttt agcccaagtg gagcctgaca    5700
gccagaactc tgtgtccccc gtctaaccac agctcctttt ccagagcatt ccagtcaggc    5760
```

```
tctctgggct gactgggcca ggggaggtta caggtaccag ttctttaaga agatctttgg   5820
gcatatacat ttttagcctg tgtcattgcc ccaaatggat tcctgtttca agttcacacc   5880
tgcagattct aggacctgtg tcctagactt cagggagtca gctgtttcta gagttcctac   5940
catggagtgg gtctggagga cctgcccggt ggggggggcag agccctgctc cctccgggtc   6000
ttcctactct tctctctgct ctgacgggat tgttgattc tctccatttt ggtgtctttc    6060
tcttttagat attgtatcaa tctttagaaa aggcatagtc tacttgttat aaatcgttag   6120
gatactgcct cccccagggt ctaaaattac atattagagg ggaaaagctg aacactgaag   6180
tcagttctca acaatttaga aggaaaacct agaaaacatt tggcagaaaa ttacatttcg   6240
atgttttga atgaatacga gcaagctttt acaacagtgc tgatctaaaa atacttagca    6300
cttggcctga gatgcctggt gagcattaca ggcaagggga atctggaggt agccgacctg   6360
aggacatggc ttctgaacct gtcttttggg agtggtatgg aaggtggagc gttcaccagt   6420
gacctggaag gcccagcacc accctccttc ccactcttct catcttgaca gagcctgccc   6480
cagcgctgac gtgtcaggaa acacccagg gaactaggaa ggcacttctg cctgaggggc    6540
agcctgcctt gcccactcct gctctgctcg cctcggatca gctgagcctt ctgagctggc   6600
ctctcactgc ctccccaagg ccccctgcct gccctgtcag gaggcagaag gaagcaggtg   6660
tgagggcagt gcaaggaggg agcacaaccc ccagctcccg ctccgggctc cgacttgtgc   6720
acaggcagag cccagaccct ggaggaaatc ctacctttga attcaagaac atttggggaa   6780
tttgaaaatc tctttgcccc caaacccca ttctgtccta cctttaatca ggtcctgctc     6840
agcagtgaga gcagatgagg tgaaaaggcc aagaggtttg gctcctgccc actgatagcc   6900
cctctccccg cagtgtttgt gtgtcaagtg gcaaagctgt tcttcctggt gaccctgatt   6960
atatccagta acacatagac tgtgcgcata ggcctgcttt gtctcctcta tcctgggctt   7020
ttgttttgct ttttagtttt gcttttagtt tttctgtccc ttttatttaa cgcaccgact   7080
agacacacaa agcagttgaa ttttatata tatatctgta tattgcacaa ttataaactc    7140
attttgcttg tggctccaca cacacaaaaa aagacctgtt aaaattatac ctgttgctta   7200
attacaatat ttctgataac catagcatag acaagggaa aataaaaaa gaaaaaaaag     7260
aaaaaaaaac gacaaatctg tctgctggtc acttcttctg tccaagcaga ttcgtggtct   7320
tttcctcgct tctttcaagg gctttcctgt gccaggtgaa ggaggctcca ggcagcaccc   7380
aggttttgca ctcttgtttc tcccgtgctt gtgaaagagg tcccaaggtt ctgggtgcag   7440
gagcgctccc ttgacctgct gaagtccgga acgtagtcgg cacagcctgg tcgccttcca   7500
cctctgggag ctggagtcca ctggggtggc ctgactcccc cagtcccctt cccgtgacct   7560
ggtcagggtg agcccatgtg gagtcagcct cgcaggcctc cctgccagta gggtccgagt   7620
gtgtttcatc cttcccactc tgtcgagcct ggggctgga gcggagacgg gaggcctggc    7680
ctgtctcgga acctgtgagc tgcaccaggt agaacgccag ggaccccaga atcatgtgcg   7740
tcagtccaag gggtcccctc caggagtagt gaagactcca gaaatgtccc tttcttctcc   7800
cccatcctac gagtaattgc atttgctttt gtaattctta atgagcaata tctgctagag   7860
agtttagctg taacagttct ttttgatcat cttttttaa taattagaaa caccaaaaaa    7920
atccagaaac ttgttcttcc aaagcagaga gcattataat caccagggcc aaaagcttcc   7980
ctccctgctg tcattgcttc ttctgaggcc tgaatccaaa agaaaaacag ccataggccc   8040
tttcagtggc cgggctaccc gtgagccctt cggaggacca gggctgggc agcctctggg     8100
cccacatccg gggccagctc cggcgtgtgt tcagtgttag cagtgggtca tgatgctctt   8160
```

```
tcccacccag cctgggatag ggcagagga ggcgaggagg ccgttgccgc tgatgtttgg      8220
ccgtgaacag gtgggtgtct gcgtgcgtcc acgtgcgtgt tttctgactg acatgaaatc      8280
gacgcccgag ttagcctcac ccggtgacct ctagccctgc ccggatggag cggggcccac      8340
ccggttcagt gtttctgggg agctggacag tggagtgcaa aaggcttgca gaacttgaag      8400
cctgctcctt cccttgctac cacggcctcc tttccgtttg atttgtcact gcttcaatca      8460
ataacagccg ctccagagtc agtagtcaat gaatatatga ccaaatatca ccaggactgt      8520
tactcaatgt gtgccgagcc cttgcccatg ctgggctccc gtgtatctgg acactgtaac      8580
gtgtgctgtg tttgctcccc ttccccttcc ttctttgccc tttacttgtc tttctggggt      8640
ttttctgttt gggtttggtt tggttttttat ttctccttttt gtgttccaaa catgaggttc      8700
tctctactgg tcctcttaac tgtggtgttg aggcttatat ttgtgtaatt tttggtgggt      8760
gaaaggaatt ttgctaagta aatctcttct gtgtttgaac tgaagtctgt attgtaacta      8820
tgtttaaagt aattgttcca gagacaaata tttctagaca cttttctttt acaaacaaaa      8880
gcattcggag ggaggggat ggtgactgag atgagagggg agagctgaac agatgacccc      8940
tgcccagatc agccagaagc cacccaaagc agtggagccc aggagtccca ctccaagcca      9000
gcaagccgaa tagctgatgt gttgccactt tccaagtcac tgcaaaacca ggttttgttc      9060
cgcccagtgg attcttgttt tgcttcccct cccccgaga ttattaccac catcccgtgc      9120
ttttaaggaa aggcaagatt gatgtttcct tgaggggagc caggagggga tgtgtgtgtg      9180
cagagctgaa gagctgggga gaatgggggct gggcccaccc aagcaggagg ctgggacgct      9240
ctgctgtggg cacaggtcag gctaatgttg gcagatgcag ctcttcctgg acaggccagg      9300
tggtgggcat tctctctcca aggtgtgccc cgtgggcatt actgtttaag acacttccgt      9360
cacatcccac cccatcctcc agggctcaac actgtgacat ctctattccc caccctcccc      9420
ttcccagggc aataaaatga ccatggaggg ggcttgcact ctcttggctg tcacccgatc      9480
gccagcaaaa cttagatgtg agaaaacccc ttcccattcc atggcgaaaa catctcctta      9540
gaaaagccat taccctcatt aggcatggtt ttgggctccc aaaacacctg acagcccctc      9600
cctcctctga gaggcggaga gtgctgactg tagtgaccat tgcatgccgg gtgcagcatc      9660
tggaagagct aggcagggtg tctgcccccct cctgagttga agtcatgctc ccctgtgcca      9720
gcccagaggc cgagagctat ggacagcatt gccagtaaca caggccaccc tgtgcagaag      9780
ggagctggct ccagcctgga aacctgtctg aggttgggag aggtgcactt ggggcacagg      9840
gagaggccgg gacacactta gctggagatg tctctaaaag ccctgtatcg tattcacctt      9900 cagttttttgt gttttgggac aattacttta gaaataagt aggtcgtttt aaaaacaaaa      9960
attattgatt gcttttttgt agtgttcaga aaaaggttc tttgtgtata gccaaatgac     10020
tgaaagcact gatatattta aaaacaaaag gcaatttatt aaggaaattt gtaccatttc     10080
agtaaacctg tctgaatgta cctgtatacg tttcaaaaac ccccccccc cactgaatcc     10140 ctgtaaccta tttattatat aaagagtttg ccttataaat tt                        10182
```

<210> SEQ ID NO 2
<211> LENGTH: 486
<212> TYPE: PRT
<213> ORGANISM: Homo sapiens

<400> SEQUENCE: 2

```
Met Val Ala Gly Met Leu Gly Leu Arg Glu Glu Lys Ser Glu Asp Gln
  1               5                  10                  15
```

-continued

```
Asp Leu Gln Gly Leu Lys Asp Lys Pro Leu Lys Phe Lys Lys Val Lys
             20                  25                  30
Lys Asp Lys Lys Glu Glu Lys Glu Gly Lys His Glu Pro Val Gln Pro
         35                  40                  45
Ser Ala His His Ser Ala Glu Pro Ala Glu Ala Gly Lys Ala Glu Thr
 50                  55                  60
Ser Glu Gly Ser Gly Ser Ala Pro Ala Val Pro Glu Ala Ser Ala Ser
 65                  70                  75                  80
Pro Lys Gln Arg Arg Ser Ile Ile Arg Asp Arg Gly Pro Met Tyr Asp
             85                  90                  95
Asp Pro Thr Leu Pro Glu Gly Trp Thr Arg Lys Leu Lys Gln Arg Lys
            100                 105                 110
Ser Gly Arg Ser Ala Gly Lys Tyr Asp Val Tyr Leu Ile Asn Pro Gln
        115                 120                 125
Gly Lys Ala Phe Arg Ser Lys Val Glu Leu Ile Ala Tyr Phe Glu Lys
    130                 135                 140
Val Gly Asp Thr Ser Leu Asp Pro Asn Asp Phe Asp Phe Thr Val Thr
145                 150                 155                 160
Gly Arg Gly Ser Pro Ser Arg Arg Glu Gln Lys Pro Pro Lys Lys Pro
                165                 170                 175
Lys Ser Pro Lys Ala Pro Gly Thr Gly Arg Gly Arg Gly Arg Pro Lys
            180                 185                 190
Gly Ser Gly Thr Thr Arg Pro Lys Ala Ala Thr Ser Glu Gly Val Gln
        195                 200                 205
Val Lys Arg Val Leu Glu Lys Ser Pro Gly Lys Leu Leu Val Lys Met
    210                 215                 220
Pro Phe Gln Thr Ser Pro Gly Gly Lys Ala Glu Gly Gly Gly Ala Thr
225                 230                 235                 240
Thr Ser Thr Gln Val Met Val Ile Lys Arg Pro Gly Arg Lys Arg Lys
                245                 250                 255
Ala Glu Ala Asp Pro Gln Ala Ile Pro Lys Lys Arg Gly Arg Lys Pro
            260                 265                 270
Gly Ser Val Val Ala Ala Ala Ala Glu Ala Lys Lys Lys Ala Val
        275                 280                 285
Lys Glu Ser Ser Ile Arg Ser Val Gln Glu Thr Val Leu Pro Ile Lys
    290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ala Ser Ser Pro Pro Lys Lys Glu His His His
        355                 360                 365
His His His His Ser Glu Ser Pro Lys Ala Pro Val Pro Leu Leu Pro
    370                 375                 380
Pro Leu Pro Pro Pro Pro Glu Pro Glu Ser Ser Glu Asp Pro Thr
385                 390                 395                 400
Ser Pro Pro Glu Pro Gln Asp Leu Ser Ser Val Cys Lys Glu Glu
                405                 410                 415
Lys Met Pro Arg Gly Gly Ser Leu Glu Ser Asp Gly Cys Pro Lys Glu
            420                 425                 430
```

| Pro | Ala | Lys | Thr | Gln | Pro | Ala | Val | Ala | Thr | Ala | Ala | Thr | Ala | Ala | Glu |
|---|---|---|---|---|---|---|---|---|---|---|---|---|---|---|---|
|  | 435 |  |  |  | 440 |  |  |  |  | 445 |  |  |  |  |  |

| Lys | Tyr | Lys | His | Arg | Gly | Glu | Gly | Glu | Arg | Lys | Asp | Ile | Val | Ser | Ser |
|---|---|---|---|---|---|---|---|---|---|---|---|---|---|---|---|
| 450 |  |  |  |  | 455 |  |  |  |  | 460 |  |  |  |  |  |

| Ser | Met | Pro | Arg | Pro | Asn | Arg | Glu | Glu | Pro | Val | Asp | Ser | Arg | Thr | Pro |
|---|---|---|---|---|---|---|---|---|---|---|---|---|---|---|---|
| 465 |  |  |  | 470 |  |  |  |  | 475 |  |  |  |  | 480 |  |

| Val | Thr | Glu | Arg | Val | Ser |
|---|---|---|---|---|---|
|  |  |  |  | 485 |  |

<210> SEQ ID NO 3
<211> LENGTH: 1504
<212> TYPE: DNA
<213> ORGANISM: Homo sapiens

<400> SEQUENCE: 3

```
ccggaaaatg gccgccgccg ccgccgccgc gccgagcgga ggaggaggag gaggcgagga      60
ggagagactg gaagaaaagt cagaagacca ggacctccag ggcctcaagg acaaacccct     120
caagtttaaa aaggtgaaga agataagaa agaagagaaa gagggcaagc atgagcccgt     180
gcagccatca gccccaccact ctgctgagcc gcagaggga ggcaaagcag agacatcaga     240
agggtcaggc tccgccccgg ctgtgccgga agcttctgcc tcccccaaac agcggcgctc     300
catcatccgt gaccggggac ccatgtatga tgacccacc ctgcctgaag ctggacacg      360
gaagcttaag caaaggaaat ctggccgctc tgctgggaag tatgatgtgt atttgatcaa     420
tccccaggga aaagcctttc gctctaaagt ggagttgatt gcgtacttcg aaaaggtagg     480
cgacacatcc ctggacccta atgattttga cttcacggta actgggagag ggagcccctc     540
ccggcgagag cagaaaccac ctaagaagcc caaatctccc aaagctccag gaactggcag     600
aggccgggga cgccccaaag ggagcggcac cacgagaccc aaggcggcca cgtcagaggg     660
tgtgcaggtg aaaagggtcc tggagaaaag tcctgggaag ctccttgtca agatgccttt     720
tcaaacttcg ccaggggggca aggctgaggg gggtggggcc accacatcca cccaggtcat     780
ggtgatcaaa cgccccggca ggaagcgaaa agctgaggcc gaccctcagg ccattcccaa     840
gaaacgggc cgaaagccgg ggagtgtggt ggcagccgct gccgccgagg ccaaaaagaa     900
agccgtgaag gagtcttcta tccgatctgt gcaggagacc gtactcccca tcaagaagcg     960
caagacccgg gagacggtca gcatcgaggt caaggaagtg gtgaagcccc tgctggtgtc    1020
caccctcggt gagaagagcg ggaaaggact gaagacctgt aagagccctg ggcggaaaag    1080
caaggagagc agccccaagg ggcgcagcag cagcgcctcc tcaccccca agaaggagca    1140
ccaccaccat caccaccact cagagtcccc aaaggccccc gtgccactgc tcccaccccct    1200
gccccaccct ccacctgagc ccgagagctc cgaggacccc accagccccc ctgagcccca    1260
ggacttgagc agcagcgtct gcaaagagga agatgccc agaggaggct cactggagag    1320
cgacggctgc cccaaggagc cagctaagac tcagcccgcg gttgccaccg ccgccacggc    1380
cgcagaaaag tacaaacacc gaggggaggg agagcgcaaa gacattgttt catcctccat    1440
gccaaggcca aacagagagg agcctgtgga cagccggacg cccgtgaccg agagagttag    1500
ctga                                                                 1504
```

<210> SEQ ID NO 4
<211> LENGTH: 498
<212> TYPE: PRT
<213> ORGANISM: Homo sapiens

<400> SEQUENCE: 4

```
Met Ala Ala Ala Ala Ala Ala Pro Ser Gly Gly Gly Gly Gly
  1               5                  10                  15

Glu Glu Glu Arg Leu Glu Glu Lys Ser Glu Asp Gln Asp Leu Gln Gly
             20                  25                  30

Leu Lys Asp Lys Pro Leu Lys Phe Lys Lys Val Lys Lys Asp Lys Lys
         35                  40                  45

Glu Glu Lys Glu Gly Lys His Glu Pro Val Gln Pro Ser Ala His His
 50                  55                  60

Ser Ala Glu Pro Ala Glu Ala Gly Lys Ala Glu Thr Ser Glu Gly Ser
 65                  70                  75                  80

Gly Ser Ala Pro Ala Val Pro Glu Ala Ser Ala Ser Pro Lys Gln Arg
                 85                  90                  95

Arg Ser Ile Ile Arg Asp Arg Gly Pro Met Tyr Asp Asp Pro Thr Leu
             100                 105                 110

Pro Glu Gly Trp Thr Arg Lys Leu Lys Gln Arg Lys Ser Gly Arg Ser
         115                 120                 125

Ala Gly Lys Tyr Asp Val Tyr Leu Ile Asn Pro Gln Gly Lys Ala Phe
 130                 135                 140

Arg Ser Lys Val Glu Leu Ile Ala Tyr Phe Glu Lys Val Gly Asp Thr
145                 150                 155                 160

Ser Leu Asp Pro Asn Asp Phe Asp Phe Thr Val Thr Gly Arg Gly Ser
                 165                 170                 175

Pro Ser Arg Arg Glu Gln Lys Pro Pro Lys Lys Pro Lys Ser Pro Lys
         180                 185                 190

Ala Pro Gly Thr Gly Arg Gly Arg Gly Arg Pro Lys Gly Ser Gly Thr
             195                 200                 205

Thr Arg Pro Lys Ala Ala Thr Ser Glu Gly Val Gln Val Lys Arg Val
         210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Gly Ala Thr Thr Ser Thr Gln
                 245                 250                 255

Val Met Val Ile Lys Arg Pro Gly Arg Lys Arg Lys Ala Glu Ala Asp
             260                 265                 270

Pro Gln Ala Ile Pro Lys Lys Arg Gly Arg Lys Pro Gly Ser Val Val
         275                 280                 285

Ala Ala Ala Ala Ala Glu Ala Lys Lys Lys Ala Val Lys Glu Ser Ser
 290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                 325                 330                 335

Val Ser Thr Leu Gly Glu Lys Ser Gly Lys Gly Leu Lys Thr Cys Lys
             340                 345                 350

Ser Pro Gly Arg Lys Ser Lys Glu Ser Ser Pro Lys Gly Arg Ser Ser
         355                 360                 365

Ser Ala Ser Ser Pro Pro Lys Lys Glu His His His His His His
 370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                 405                 410                 415
```

```
Pro Gln Asp Leu Ser Ser Val Cys Lys Glu Glu Lys Met Pro Arg
        420             425             430

Gly Gly Ser Leu Glu Ser Asp Gly Cys Pro Lys Glu Pro Ala Lys Thr
            435             440             445

Gln Pro Ala Val Ala Thr Ala Thr Ala Ala Glu Lys Tyr Lys His
    450             455             460

Arg Gly Glu Gly Glu Arg Lys Asp Ile Val Ser Ser Met Pro Arg
465             470             475             480

Pro Asn Arg Glu Glu Pro Val Asp Ser Arg Thr Pro Val Thr Glu Arg
            485             490             495

Val Ser
```

<210> SEQ ID NO 5
<211> LENGTH: 18
<212> TYPE: DNA
<213> ORGANISM: Artificial Sequence
<220> FEATURE:
<223> OTHER INFORMATION: HF primer

<400> SEQUENCE: 5
ctcggagaga gggctgtg                                                    18

<210> SEQ ID NO 6
<211> LENGTH: 20
<212> TYPE: DNA
<213> ORGANISM: Artificial Sequence
<220> FEATURE:
<223> OTHER INFORMATION: HR1 primer

<400> SEQUENCE: 6
cttgaggggt ttgtccttga                                                  20

<210> SEQ ID NO 7
<211> LENGTH: 20
<212> TYPE: DNA
<213> ORGANISM: Artificial Sequence
<220> FEATURE:
<223> OTHER INFORMATION: HR2 primer

<400> SEQUENCE: 7
cgtttgatca ccatgacctg                                                  20

<210> SEQ ID NO 8
<211> LENGTH: 20
<212> TYPE: DNA
<213> ORGANISM: Artificial Sequence
<220> FEATURE:
<223> OTHER INFORMATION: MF primer

<400> SEQUENCE: 8
aggaggcgag gaggagagac                                                  20

<210> SEQ ID NO 9
<211> LENGTH: 19
<212> TYPE: DNA
<213> ORGANISM: Artificial Sequence
<220> FEATURE:
<223> OTHER INFORMATION: MR primer

<400> SEQUENCE: 9
ctggctctgc agaatggtg                                                   19

<210> SEQ ID NO 10

```
<211> LENGTH: 22
<212> TYPE: DNA
<213> ORGANISM: Artificial Sequence
<220> FEATURE:
<223> OTHER INFORMATION: MECP2B-specific primer

<400> SEQUENCE: 10
aggagagact ggaagaaaag tc                                              22

<210> SEQ ID NO 11
<211> LENGTH: 20
<212> TYPE: DNA
<213> ORGANISM: Artificial Sequence
<220> FEATURE:
<223> OTHER INFORMATION: reverse primer

<400> SEQUENCE: 11
cttgaggggt ttgtccttga                                                 20

<210> SEQ ID NO 12
<211> LENGTH: 23
<212> TYPE: DNA
<213> ORGANISM: Artificial Sequence
<220> FEATURE:
<223> OTHER INFORMATION: MECP2A transcript-specific primer

<400> SEQUENCE: 12
ctcaccagtt cctgctttga tgt                                             23

<210> SEQ ID NO 13
<211> LENGTH: 22
<212> TYPE: DNA
<213> ORGANISM: Artificial Sequence
<220> FEATURE:
<223> OTHER INFORMATION: MECP2B transcript-specific primer

<400> SEQUENCE: 13
aggagagact ggaggaaaag tc                                              22

<210> SEQ ID NO 14
<211> LENGTH: 25
<212> TYPE: DNA
<213> ORGANISM: Artificial Sequence
<220> FEATURE:
<223> OTHER INFORMATION: reverse primer

<400> SEQUENCE: 14
cttaaacttc agtggcttgt ctctg                                           25

<210> SEQ ID NO 15
<211> LENGTH: 23
<212> TYPE: DNA
<213> ORGANISM: Artificial Sequence
<220> FEATURE:
<223> OTHER INFORMATION: MECP2A forward primer

<400> SEQUENCE: 15
tatggatcca tggtagctgg gat                                             23

<210> SEQ ID NO 16
<211> LENGTH: 21
<212> TYPE: DNA
<213> ORGANISM: Artificial Sequence
<220> FEATURE:
<223> OTHER INFORMATION: MECP2B forward primer

<400> SEQUENCE: 16
```

```
tatggatccg gaaaatggcc g                                              21

<210> SEQ ID NO 17
<211> LENGTH: 20
<212> TYPE: DNA
<213> ORGANISM: Artificial Sequence
<220> FEATURE:
<223> OTHER INFORMATION: reverse primer

<400> SEQUENCE: 17
gcgtctagag ctaactctct                                                20

<210> SEQ ID NO 18
<211> LENGTH: 21
<212> TYPE: PRT
<213> ORGANISM: Artificial Sequence
<220> FEATURE:
<223> OTHER INFORMATION: MeCP2 N-terminus

<400> SEQUENCE: 18

Met Ala Ala Ala Ala Ala Ala Pro Ser Gly Gly Gly Gly Gly Gly
 1               5                  10                  15

Glu Glu Glu Arg Leu
            20

<210> SEQ ID NO 19
<211> LENGTH: 18
<212> TYPE: DNA
<213> ORGANISM: Artificial Sequence
<220> FEATURE:
<223> OTHER INFORMATION: X1F primer

<400> SEQUENCE: 19
ccatcacagc caatgacg                                                  18

<210> SEQ ID NO 20
<211> LENGTH: 20
<212> TYPE: DNA
<213> ORGANISM: Artificial Sequence
<220> FEATURE:
<223> OTHER INFORMATION: X1R primer

<400> SEQUENCE: 20
agggggaggg tagagaggag                                                20

<210> SEQ ID NO 21
<211> LENGTH: 10171
<212> TYPE: DNA
<213> ORGANISM: Homo sapiens

<400> SEQUENCE: 21
ccggaaaatg gccgccgccg ccgccgccgc gccgagcagg aggcgaggag gagagactgc    60
tccataaaaa tacagactca ccagttcctg ctttgatgtg acatgtgact ccccagaata   120
caccttgctt ctgtagacca gctccaacag gattccatgg tagctgggat gttagggctc   180
agggaagaaa agtcagaaga ccaggacctc cagggcctca aggacaaacc cctcaagttt   240
aaaaaggtga agaaagataa gaagaagag aaagagggca agcatgagcc cgtgcagcca   300
tcagcccacc actctgctga gcccgcagag gcaggcaaag cagagacatc agaagggtca   360
ggctccgccc cggctgtgcc ggaagcttct gcctccccca acagcggcg ctccatcatc   420 cgtgaccggg gacccatgta tgatgacccc accctgcctg aaggctggac acggaagctt   480
```

```
aagcaaagga aatctggccg ctctgctggg aagtatgatg tgtatttgat caatccccag    540
ggaaaagcct ttcgctctaa agtggagttg attgcgtact tcgaaaaggt aggcgacaca    600
tccctggacc ctaatgattt tgacttcacg gtaactggga gagggagccc ctcccggcga    660
gagcagaaac cacctaagaa gcccaaatct cccaaagctc caggaactgg cagaggccgg    720
ggacgcccca agggagcgg caccacgaga cccaaggcgg ccacgtcaga gggtgtgcag    780
gtgaaaaggg tcctggagaa aagtcctggg aagctccttg tcaagatgcc ttttcaaact    840
tcgccagggg gcaaggctga ggggggtggg gccaccacat ccacccaggt catggtgatc    900
aaacgccccg gcaggaagcg aaaagctgag gccgaccctc aggccattcc caagaaacgg    960
ggccgaaagc cggggagtgt ggtggcagcc gctgccgccg aggccaaaaa gaaagccgtg   1020
aaggagtctt ctatccgatc tgtgcaggag accgtactcc ccatcaagaa gcgcaagacc   1080
cgggagacgg tcagcatcga ggtcaaggaa gtggtgaagc ccctgctggt gtccaccctc   1140
ggtgagaaga gcgggaaagg actgaagacc tgtaagagcc tgggcggaa aagcaaggag    1200 agcagcccca aggggcgcag cagcagcgcc tcctcacccc caagaagga gcaccaccac    1260 catcaccacc actcagagtc cccaaaggcc ccgtgccac tgctcccacc cctgccccca    1320
cctccacctg agcccgagag ctccgaggac cccaccagcc ccctgagcc caggacttg     1380 agcagcagcg tctgcaaaga ggagaagatg cccagaggag gctcactgga gagcgacggc   1440
tgccccaagg agccagctaa gactcagccc gcggttgcca ccgccgccac ggccgcagaa   1500
aagtacaaac accgagggga gggagagcgc aaagacattg tttcatcctc catgccaagg   1560
ccaaacagag aggagcctgt ggacagccgg acgcccgtga ccgagagagt tagctgactt   1620
tacacggagc ggattgcaaa gcaaaccaac aagaataaag gcagctgttg tctcttctcc   1680
ttatgggtag ggctctgaca aagcttcccg attaactgaa ataaaaaata ttttttttc    1740 tttcagtaaa cttagagttt cgtggcttca gggtgggagt agttggagca ttggggatgt   1800
ttttcttacc gacaagcaca gtcaggttga agacctaacc agggccagaa gtagctttgc   1860
acttttctaa actaggctcc ttcaacaagg cttgctgcag atactactga ccagacaagc   1920
tgttgaccag gcacctcccc tcccgcccaa acctttcccc catgtggtcg ttagagacag   1980
agcgacagag cagttgagag gacactcccg ttttcggtgc catcagtgcc ccgtctacag   2040
ctcccccagc tcccccacc tcccccactc ccaaccacgt tgggacaggg aggtgtgagg    2100
caggagagac agttggattc tttagagaag atggatatga ccagtggcta tggcctgtgc   2160
gatcccaccc gtggtggctc aagtctggcc ccacaccagc cccaatccaa aactggcaag   2220
gacgcttcac aggacaggaa agtggcacct gtctgctcca gctctggcat ggctaggagg   2280
ggggagtccc ttgaactact gggtgtagac tggcctgaac cacaggagag gatggcccag   2340
ggtgaggtgg catggtccat tctcaaggga cgtcctccaa cgggtggcgc tagaggccat   2400
ggaggcagta ggacaaggtg caggcaggct ggcctgggg caggccgggc agagcacagc    2460
ggggtgagag ggattcctaa tcactcagag cagtctgtga cttagtggac aggggagggg   2520
gcaaaggggg aggagaagaa aatgttcttc cagttacttt ccaattctcc tttagggaca   2580
gcttagaatt atttgcacta ttgagtcttc atgttcccac ttcaaaacaa acagatgctc   2640
tgagagcaaa ctggcttgaa ttggtgacat ttagtccctc aagccaccag atgtgacagt   2700
gttgagaact acctggattt gtatatatac ctgcgcttgt tttaaagtgg gctcagcaca   2760
tagggttccc acgaagctcc gaaactctaa gtgtttgctg caattttata aggacttcct   2820 gatttggtttc tcttctcccc ttccatttct gccttttgtt catttcatcc tttcacttct   2880
```

-continued

```
ttcccttcct ccgtcctcct ccttcctagt tcatcccttc tcttccaggc agccgcggtg    2940
cccaaccaca cttgtcggct ccagtcccca gaactctgcc tgccctttgt cctcctgctg    3000
ccagtaccag ccccaccctg ttttgagccc tgaggaggcc ttgggctctg ctgagtccga    3060
cctggcctgt ctgtgaagag caagagagca gcaaggtctt gctctcctag gtagccccct    3120
cttccctggt aagaaaaagc aaaaggcatt tcccaccctg aacaacgagc cttttcaccc    3180
ttctactcta gagaagtgga ctggaggagc tgggcccgat ttggtagttg aggaaagcac    3240
agaggcctcc tgtggcctgc cagtcatcga gtggcccaac aggggctcca tgccagccga    3300
ccttgacctc actcagaagt ccagagtcta gcgtagtgca gcagggcagt agcggtacca    3360
atgcagaact cccaagaccc gagctgggac cagtacctgg gtccccagcc cttcctctgc    3420 tcccccttt ccctcggagt tcttcttgaa tggcaatgtt ttgcttttgc tcgatgcaga    3480 caggggcca gaacaccaca catttcactg tctgtctggt ccatagctgt ggtgtagggg    3540
cttagaggca tgggcttgct gtgggttttt aattgatcag ttttcatgtg ggatcccatc    3600 ttttaacct ctgttcagga agtccttatc tagctgcata tcttcatcat attggtatat    3660 cctttctgt gtttacagag atgtctctta tatctaaatc tgtccaactg agaagtacct    3720
tatcaaagta gcaaatgaga cagcagtctt atgcttccag aaacacccac aggcatgtcc    3780
catgtgagct gctgccatga actgtcaagt gtgtgttgtc ttgtgtattt cagttattgt    3840
ccctggcttc cttactatgg tgtaatcatg aaggagtgaa acatcataga aactgtctag    3900
cacttccttg ccagtcttta gtgatcagga accatagttg acagttccaa tcagtagctt    3960
aagaaaaaac cgtgtttgtc tcttctggaa tggttagaag tgagggagtt tgccccgttc    4020
tgtttgtaga gtctccatagt tggactttct agcatatatg tgtccatttc cttatgctgt    4080
aaaagcaagt cctgcaacca aactcccatc agcccaatcc ctgatccctg atcccttcca    4140
cctgctctgc tgatgacccc cccagcttca cttctgactc ttccccagga agggaagggg    4200
ggtcagaaga gagggtgagt cctccagaac tcttcctcca aggacagaag gctcctgccc    4260
ccatagtggc ctcgaactcc tggcactacc aaaggacact tatccacgag agcgcagcat    4320
ccgaccaggt tgtcactgag aagatgttta ttttggtcag ttgggttttt atgtattata    4380
cttagtcaaa tgtaatgtgg cttctggaat cattgtccag agctgcttcc ccgtcacctg    4440
ggcgtcatct ggtcctggta agaggagtgc gtggcccacc aggccccct gtcacccatg    4500 acagttcatt cagggccgat ggggcagtcg tggttgggaa cacagcattt caagcgtcac    4560
tttatttcat tcgggcccca cctgcagctc cctcaaagag gcagttgccc agcctctttc    4620
ccttccagtt tattccagag ctgccagtgg ggcctgaggc tccttagggt tttctctcta    4680 tttcccctt tcttcctcat tccctcgtct ttcccaaagg catcacgagt cagtcgcctt    4740
tcagcaggca gccttggcgg tttatcgccc tggcaggcag gggccctgca gctctcatgc    4800
tgcccctgcc ttggggtcag gttgacagga ggttggaggg aaagccttaa gctgcaggat    4860
tctcaccagc tgtgtccggc ccagttttgg ggtgtgacct caatttcaat tttgtctgta    4920
cttgaacatt atgaagatgg gggcctcttt cagtgaattt gtgaacagca gaattgaccg    4980
acagctttcc agtacccatg gggctaggtc attaaggcca catccacagt ctcccccacc    5040
cttgttccag ttgttagtta ctacctcctc tcctgacaat actgtatgtc gtcgagctcc    5100
ccccaggtct acccctcccg gccctgcctg ctggtgggct tgtcatagcc agtgggattg    5160
ccggtcttga cagctcagtg agctggagat acttggtcac agccaggcgc tagcacagct    5220
```

```
cccttctgtt gatgctgtat tcccatatca aaagacacag gggacaccca gaaacgccac    5280
atcccccaat ccatcagtgc caaactagcc aacggcccca gcttctcagc tcgctggatg    5340
gcggaagctg ctactcgtga gcgccagtgc gggtgcagac aatcttctgt tgggtggcat    5400
cattccaggc ccgaagcatg aacagtgcac ctgggacagg gagcagcccc aaattgtcac    5460
ctgcttctct gcccagcttt tcattgctgt gacagtgatg gcgaaagagg gtaataacca    5520
gacacaaact gccaagttgg gtggagaaag gagtttcttt agctgacaga atctctgaat    5580
tttaaatcac ttagtaagcg gctcaagccc aggagggagc agagggatac gagcggagtc    5640
ccctgcgcgg gaccatctgg aattggttta gcccaagtgg agcctgacag ccagaactct    5700
gtgtcccccg tctaaccaca gctccttttc cagagcattc cagtcaggct ctctgggctg    5760
actgggccag gggaggttac aggtaccagt tctttaagaa gatctttggg catatacatt    5820
tttagcctgt gtcattgccc caaatggatt cctgtttcaa gttcacacct gcagattcta    5880
ggacctgtgt cctagacttc agggagtcag ctgtttctag agttcctacc atggagtggg    5940
tctggaggac ctgcccggtg gggggcaga gccctgctcc ctccgggtct tcctactctt    6000
ctctctgctc tgacgggatt tgttgattct ctccattttg gtgtctttct cttttagata    6060
ttgtatcaat cttagaaaa ggcatagtct acttgttata aatcgttagg atactgcctc    6120
ccccagggtc taaaattaca tattagaggg gaaaagctga acactgaagt cagttctcaa    6180
caatttagaa ggaaaaccta gaaaacattt ggcagaaaat tacatttcga tgttttttgaa    6240
tgaatacgag caagctttta caacagtgct gatctaaaaa tacttagcac ttggcctgag    6300
atgcctggtg agcattacag gcaaggggaa tctggaggta gccgacctga ggacatggct    6360
tctgaacctg tcttttggga gtggtatgga aggtggagcg ttcaccagtg acctggaagg    6420
cccagcacca ccctccttcc cactcttctc atcttgacag agcctgcccc agcgctgacg    6480
tgtcaggaaa acacccaggg aactaggaag gcacttctgc ctgagggggca gcctgccttg    6540
cccactcctg ctctgctcgc ctcggatcag ctgagccttc tgagctggcc tctcactgcc    6600
tccccaaggc cccctgcctg ccctgtcagg aggcagaagg aagcaggtgt gagggcagtg    6660
caaggaggga gcacaacccc cagctcccgc tccgggctcc gacttgtgca caggcagagc    6720
ccagaccctg gaggaaatcc tacctttgaa ttcaagaaca tttggggaat ttggaaatct    6780
cttttgcccc aaacccccat tctgtcctac ctttaatcag gtcctgctca gcagtgagag    6840
cagatgaggt gaaaaggcca agaggttttgg ctcctgccca ctgatagccc ctctccccgc    6900
agtgtttgtg tgtcaagtgg caaagctgtt cttcctggtg accctgatta tatccagtaa    6960
cacatagact gtgcgcatag gcctgcttg tctcctctat cctgggcttt tgttttgctt    7020
tttagttttg cttttagttt ttctgtccct tttatttaac gcaccgacta gacacacaaa    7080
gcagttgaat ttttatatat atatctgtat attgcacaat tataaactca ttttgcttgt    7140
ggctccacac acacaaaaaa agacctgtta aaattatacc tgttgcttaa ttacaatatt    7200
tctgataacc atagcatagg acaagggaaa ataaaaaaag aaaaaaaaga aaaaaaacg    7260
acaaatctgt ctgctggtca cttcttctgt ccaagcagat tcgtggtctt ttcctcgctt    7320
ctttcaaggg ctttcctgtg ccaggtgaag gaggctccag gcagcaccca ggttttgcac    7380
tcttgttttct cccgtgcttg tgaaagaggt cccaaggttc tgggtgcagg agcgctccct    7440
tgacctgctg aagtccggaa cgtagtcggc acagcctggt cgccttccac ctctgggagc    7500
tggagtccac tggggtggcc tgactccccc agtccccttc ccgtgacctg gtcagggtga    7560
gcccatgtgg agtcagcctc gcaggcctcc ctgccagtag ggtccgagtg tgtttcatcc    7620
```

```
ttcccactct gtcgagcctg ggggctggag cggagacggg aggcctggcc tgtctcggaa    7680
cctgtgagct gcaccaggta gaacgccagg gaccccagaa tcatgtgcgt cagtccaagg    7740
ggtcccctcc aggagtagtg aagactccag aaatgtccct tcttctcccc ccatcctacg    7800
agtaattgca tttgcttttg taattcttaa tgagcaatat ctgctagaga gtttagctgt    7860
aacagttctt tttgatcatc ttttttttaat aattagaaac accaaaaaaa tccagaaact    7920
tgttcttcca aagcagagag cattataatc accagggcca aaagcttccc tccctgctgt    7980
cattgcttct tctgaggcct gaatccaaaa gaaaaacagc cataggccct ttcagtggcc    8040
gggctacccg tgagcccttc ggaggaccag ggctgggca gcctctgggc ccacatccgg     8100
ggccagctcc ggcgtgtgtt cagtgttagc agtgggtcat gatgctcttt cccacccagc    8160
ctgggatagg ggcagaggag gcgaggaggc cgttgccgct gatgtttggc cgtgaacagg    8220
tgggtgtctg cgtgcgtcca cgtgcgtgtt tctgactga catgaaatcg acgcccgagt     8280
tagcctcacc cggtgacctc tagccctgcc cggatggagc ggggcccacc cggttcagtg    8340
tttctgggga gctggacagt ggagtgcaaa aggcttgcag aacttgaagc ctgctccttc    8400
ccttgctacc acggcctcct ttccgtttga tttgtcactg cttcaatcaa taacagccgc    8460
tccagagtca gtagtcaatg aatatatgac caaatatcac caggactgtt actcaatgtg    8520
tgccgagccc ttgcccatgc tgggctcccg tgtatctgga cactgtaacg tgtgctgtgt    8580
ttgctcccct tcccttcct tctttgcct ttacttgtct ttctggggtt tttctgtttg      8640
ggtttggttt ggttttt att tctccttttg tgttccaaac atgaggttct ctctactggt   8700
cctcttaact gtggtgttga ggcttatatt tgtgtaattt ttggtgggtg aaaggaattt    8760
tgctaagtaa atctcttctg tgtttgaact gaagtctgta ttgtaactat gtttaaagta    8820
attgttccag agacaaatat ttctagacac tttttcttta caaacaaaag cattcggagg    8880
gagggggatg gtgactgaga tgagaggggga gagctgaaca gatgacccct gcccagatca   8940
gccagaagcc acccaaagca gtggagccca ggagtccac tccaagccag caagccgaat     9000
agctgatgtg ttgccacttt ccaagtcact gcaaaaccag gttttgttcc gcccagtgga    9060
ttcttgtttt gcttcccctc ccccgagat tattaccacc atcccgtgct tttaaggaaa     9120
ggcaagattg atgtttcctt gaggggagcc aggaggggat gtgtgtgtgc agagctgaag    9180
agctggggag aatggggctg gcccacccca agcaggaggc tgggacgctc tgctgtgggc    9240
acaggtcagg ctaatgttgg cagatgcagc tcttcctgga caggccaggt ggtgggcatt    9300
ctctctccaa ggtgtgcccc gtgggcatta ctgtttaaga cacttccgtc acatcccacc    9360
ccatcctcca gggctcaaca ctgtgacatc tctattcccc accctcccct tcccagggca    9420
ataaaatgac catggagggg gcttgcactc tcttggctgt cacccgatcg ccagcaaaac    9480
ttagatgtga gaaacccct tcccattcca tggcgaaaac atctccttag aaaagccatt     9540
accctcatta ggcatggttt tgggctccca aaacacctga cagcccctcc ctcctctgag    9600
aggcggagag tgctgactgt agtgaccatt gcatgccggg tgcagcatct ggaagagcta    9660
ggcagggtgt ctgccccctc ctgagttgaa gtcatgctcc cctgtgccag cccagaggcc    9720
gagagctatg gacagcattg ccagtaacac aggccaccct gtgcagaagg gagctggctc    9780
cagcctggaa acctgtctga ggttgggaga ggtgcacttg gggcacaggg agaggccggg    9840
acacacttag ctggagatgt ctctaaaagc cctgtatcgt attcaccttc agttttgtg     9900 ttttgggaca attacttag aaaataagta ggtcgtttta aaacaaaaa ttattgattg      9960
```

-continued

| | | |
|---|---|---|
| cttttttgta gtgttcagaa aaaaggttct ttgtgtatag ccaaatgact gaaagcactg | 10020 |
| atatatttaa aaacaaaagg caatttatta aggaaatttg taccatttca gtaaacctgt | 10080 |
| ctgaatgtac ctgtatacgt ttcaaaaaca ccccccccc actgaatccc tgtaacctat | 10140 |
| ttattatata aagagtttgc cttataaatt t | 10171 |

<210> SEQ ID NO 22
<211> LENGTH: 10113
<212> TYPE: DNA
<213> ORGANISM: Homo sapiens

<400> SEQUENCE: 22

| | |
|---|---|
| gctccataaa aatacagact caccagttcc tgctttgatg tgacatgtga ctccccagaa | 60 |
| tacaccttgc ttctgtagac cagctccaac aggattccat ggtagctggg atgttagggc | 120 |
| tcagggaaga aaagtcagaa gaccaggacc tccagggcct caaggacaaa cccctcaagt | 180 |
| ttaaaaggt gaagaaagat aagaagaag agaaagaggg caagcatgag cccgtgcagc | 240 |
| catcagccca ccactctgct gagcccgcag aggcaggcaa agcagagaca tcagaagggt | 300 |
| caggctccgc cccggctgtg ccggaagctt ctgcctcccc caaacagcgg cgctccatca | 360 |
| tccgtgaccg gggacccatg tatgatgacc ccaccctgcc tgaaggctgg acacggaagc | 420 |
| ttaagcaaag gaaatctggc cgctctgctg ggaagtatga tgtgtatttg atcaatcccc | 480 |
| agggaaaagc ctttcgctct aaagtggagt tgattgcgta cttcgaaaag gtaggcgaca | 540 |
| catccctgga ccctaatgat tttgacttca cggtaactgg gagagggagc ccctcccggc | 600 |
| gagagcagaa accacctaag aagcccaaat ctcccaaagc tccaggaact ggcagaggcc | 660 |
| ggggacgccc caagggagc ggcaccacga gacccaaggc ggccacgtca gagggtgtgc | 720 |
| aggtgaaaag ggtcctggag aaaagtcctg ggaagctcct tgtcaagatg ccttttcaaa | 780 |
| cttcgccagg gggcaaggct gagggggtg gggccaccac atccacccag gtcatggtga | 840 |
| tcaaacgccc cggcaggaag cgaaaagctg aggccgaccc tcaggccatt cccaagaaac | 900 |
| ggggccgaaa gccggggagt gtggtggcag ccgctgccgc cgaggccaaa agaaagccg | 960 |
| tgaaggagtc ttctatccga tctgtgcagg agaccgtact cccatcaag aagcgcaaga | 1020 |
| cccgggagac ggtcagcatc gaggtcaagg aagtggtgaa gccctgctg gtgtccaccc | 1080 |
| tcggtgagaa gagcgggaaa ggactgaaga cctgtaagag ccctgggcgg aaaagcaagg | 1140 |
| agagcagccc caaggggcgc agcagcagcg cctcctcacc ccccaagaag gagcaccacc | 1200 |
| accatcacca ccactcagag tccccaaagg ccccgtgcc actgctccca cccctgcccc | 1260 |
| cacctccacc tgagcccgag agctccgagg accccaccag cccccctgag cccaggact | 1320 |
| tgagcagcag cgtctgcaaa gaggagaaga tgcccagagg aggctcactg gagagcgacg | 1380 |
| gctgccccaa ggagccagct aagactcagc ccgcggttgc caccgccgcc acggccgcag | 1440 |
| aaaagtacaa acaccgaggg gagggagagc gcaaagacat tgtttcatcc tccatgccaa | 1500 |
| ggccaaacag agaggagcct gtggacagcc ggacgcccgt gaccgagaga gttagctgac | 1560 |
| tttacacgga gcggattgca aagcaaacca acaagaataa aggcagctgt tgtctcttct | 1620 |
| ccttatgggt agggctctga caaagcttcc cgattaactg aaataaaaaa tattttttt | 1680 |
| tctttcagta aacttagagt ttcgtggctt cagggtggga gtagtggag cattgggat | 1740 |
| gtttttctta ccgacaagca cagtcaggtt gaagacctaa ccagggccag aagtagcttt | 1800 |
| gcacttttct aaactaggct ccttcaacaa ggcttgctgc agatactact gaccagacaa | 1860 |
| gctgttgacc aggcacctcc cctcccgccc aaaccttcc cccatgtggt cgttagagac | 1920 |

```
agagcgacag agcagttgag aggacactcc cgttttcggt gccatcagtg ccccgtctac   1980
agctccccca gctccccca cctccccac tcccaaccac gttgggacag ggaggtgtga    2040
ggcaggagag acagttggat tctttagaga agatggatat gaccagtggc tatggcctgt   2100
gcgatcccac ccgtggtggc tcaagtctgg ccccacacca gccccaatcc aaaactggca   2160
aggacgcttc acaggacagg aaagtggcac ctgtctgctc cagctctggc atggctagga   2220
gggggggagtc ccttgaacta ctgggtgtag actggcctga accacaggag aggatggccc   2280
agggtgaggt ggcatggtcc attctcaagg gacgtcctcc aacgggtggc gctagaggcc   2340
atggaggcag taggacaagg tgcaggcagg ctggcctggg gtcaggccgg gcagagcaca   2400
gcggggtgag agggattcct aatcactcag agcagtctgt gacttagtgg acaggggagg   2460
ggcaaaggg ggaggagaag aaaatgttct tccagttact ttccaattct cctttaggga   2520
cagcttagaa ttatttgcac tattgagtct tcatgttccc acttcaaaac aaacagatgc   2580
tctgagagca aactggcttg aattggtgac atttagtccc tcaagccacc agatgtgaca   2640
gtgttgagaa ctacctggat ttgtatatat acctgcgctt gttttaaagt gggctcagca   2700
catagggttc ccacgaagct ccgaaactct aagtgtttgc tgcaattttta taaggacttc   2760
ctgattggtt tctcttctcc ccttccattt ctgcctttg ttcatttcat cctttcactt   2820
ctttcccttc ctccgtcctc ctccttccta gttcatccct tctcttccag gcagccgcgg   2880
tgcccaacca cacttgtcgg ctccagtccc cagaactctg cctgcccttt gtcctcctgc   2940
tgccagtacc agccccaccc tgttttgagc cctgaggagg ccttgggctc tgctgagtcc   3000
gacctggcct gtctgtgaag agcaagagag cagcaaggtc ttgctctcct aggtagcccc   3060
ctcttccctg gtaagaaaaa gcaaaaggca tttcccaccc tgaacaacga gccttttcac   3120
ccttctactc tagagaagtg gactggagga gctgggcccg atttggtagt tgaggaaagc   3180
acagaggcct cctgtggcct gccagtcatc gagtggccca acaggggctc catgccagcc   3240
gaccttgacc tcactcagaa gtccagagtc tagcgtagtg cagcagggca gtagcggtac   3300
caatgcagaa ctcccaagac ccgagctggg accagtacct gggtccccag cccttcctct   3360
gctccccctt ttccctcgga gttcttcttg aatggcaatg ttttgctttt gctcgatgca   3420
gacaggggc cagaacacca cacatttcac tgtctgtctg gtccatagct gtggtgtagg   3480
ggcttagagg catgggcttg ctgtgggttt taattgatc agttttcatg tgggatccca   3540
tcttttttaac ctctgttcag gaagtcctta tctagctgca tatcttcatc atattggtat   3600
atccttttct gtgtttacag agatgtctct tatatctaaa tctgtccaac tgagaagtac   3660
cttatcaaag tagcaaatga gacagcagtc ttatgcttcc agaaacaccc acaggcatgt   3720
cccatgtgag ctgctgccat gaactgtcaa gtgtgtgttg tcttgtgtat ttcagttatt   3780
gtccctggct tccttactat ggtgtaatca tgaaggagtg aaacatcata gaaactgtct   3840
agcacttcct tgccagtctt tagtgatcag gaaccatagt tgacagttcc aatcagtagc   3900
ttaagaaaaa accgtgtttg tctcttctgg aatggttaga agtgagggag tttgccccgt   3960
tctgtttgta gagtctcata gttggacttt ctagcatata tgtgtccatt tccttatgct   4020
gtaaaagcaa gtcctgcaac caaactccca tcagcccaat ccctgatccc tgatcccttc   4080
cacctgctct gctgatgacc ccccagcttc acttctgac tcttcccag gaagggaagg   4140
ggggtcagaa gagagggtga gtcctccaga actcttcctc caaggacaga aggctcctgc   4200
ccccatagtg gcctcgaact cctggcacta ccaaaggaca cttatccacg agagcgcagc   4260
```

```
atccgaccag gttgtcactg agaagatgtt tattttggtc agttgggttt ttatgtatta    4320
tacttagtca aatgtaatgt ggcttctgga atcattgtcc agagctgctt ccccgtcacc    4380
tgggcgtcat ctggtcctgg taagaggagt gcgtggccca ccaggccccc ctgtcaccca    4440
tgacagttca ttcagggccg atgggcagt cgtggttggg aacacagcat ttcaagcgtc     4500
actttatttc attcgggccc cacctgcagc tccctcaaag aggcagttgc ccagcctctt    4560
tcccttccag tttattccag agctgccagt ggggcctgag gctccttagg gttttctctc    4620
tatttccccc tttcttcctc attccctcgt ctttcccaaa ggcatcacga gtcagtcgcc    4680
tttcagcagg cagccttggc ggtttatcgc cctggcaggc aggggccctg cagctctcat    4740
gctgcccctg ccttggggtc aggttgacag gaggttggag ggaaagccctt aagctgcagg   4800 attctcacca gctgtgtccg gcccagtttt ggggtgtgac ctcaatttca attttgtctg    4860
tacttgaaca ttatgaagat gggggcctct ttcagtgaat tgtgaacag cagaattgac     4920 cgacagcttt ccagtaccca tggggctagg tcattaaggc cacatccaca gtctccccca    4980
cccttgttcc agttgttagt tactacctcc tctcctgaca atactgtatg tcgtcgagct    5040 cccccccaggt ctaccctcc cggccctgcc tgctggtggg cttgtcatag ccagtgggat    5100
tgccggtctt gacagctcag tgagctggag atacttggtc acagccaggc gctagcacag    5160
ctcccttctg ttgatgctgt attcccatat caaaagacac aggggacacc cagaaacgcc    5220
acatccccca atccatcagt gccaaactag ccaacggccc cagcttctca gctcgctgga    5280
tggcggaagc tgctactcgt gagcgccagt gcgggtgcag acaatcttct gttgggtggc    5340
atcattccag gcccgaagca tgaacagtgc acctgggaca gggagcagcc ccaaattgtc    5400
acctgcttct ctgcccagct tttcattgct gtgacagtga tggcgaaaga gggtaataac    5460
cagacacaaa ctgccaagtt gggtggagaa aggagtttct ttagctgaca gaatctctga    5520
attttaaatc acttagtaag cggctcaagc ccaggaggga gcagagggat acgagcggag    5580
tcccctgcgc gggaccatct ggaattggtt tagcccaagt ggagcctgac agccagaact    5640
ctgtgtcccc cgtctaacca cagctccttt tccagagcat tccagtcagg ctctctgggc    5700
tgactgggcc aggggaggtt acaggtacca gttctttaag aagatctttg ggcatataca    5760
tttttagcct gtgtcattgc cccaaatgga ttcctgtttc aagttcacac ctgcagattc    5820
taggacctgt gtcctagact tcaggagtc agctgttcct agagttccta ccatggagtg     5880
ggtctggagg acctgcccgg tgggggggca gagccctgct ccctccgggt cttcctactc    5940
ttctctctgc tctgacggga tttgttgatt ctctccattt tggtgtcttt ctcttttaga    6000
tattgtatca atctttagaa aaggcatagt ctacttgtta taaatcgtta ggatactgcc    6060
tcccccaggg tctaaaatta catattagag gggaaaagct gaacactgaa gtcagttctc    6120
aacaatttag aaggaaaacc tagaaaacat ttggcagaaa attacatttc gatgtttttg    6180
aatgaatacg agcaagcttt tacaacagtg ctgatctaaa aatacttagc acttggcctg    6240
agatgcctgg tgagcattac aggcaagggg aatctggagg tagccgacct gaggacatgg    6300
cttctgaacc tgtctttggg gagtggtatg gaaggtggag cgttcaccag tgacctggaa    6360
ggcccagcac caccctcctt cccactcttc tcatcttgac agagcctgcc ccagcgctga    6420
cgtgtcagga aaacacccag ggaactagga aggcacttct gcctgagggg cagcctgcct    6480 tgccactcc tgctctgctc gcctcggatc agctgagcct tctgagctgg cctctcactg     6540
cctccccaag gcccctgcc tgccctgtca ggaggcagaa ggaagcaggt gtgagggcag     6600
tgcaaggagg gagcacaacc cccagctccc gctccgggct ccgacttgtg cacaggcaga    6660
```

```
gcccagaccc tggaggaaat cctacctttg aattcaagaa catttgggga atttggaaat    6720
ctctttgccc ccaaaccccc attctgtcct acctttaatc aggtcctgct cagcagtgag    6780
agcagatgag gtgaaaaggc caagaggttt ggctcctgcc cactgatagc ccctctcccc    6840
gcagtgtttg tgtgtcaagt ggcaaagctg ttcttcctgg tgaccctgat tatatccagt    6900
aacacataga ctgtgcgcat aggcctgctt tgtctcctct atcctgggct tttgttttgc    6960
ttttagtttt tgcttttagt ttttctgtcc cttttattta acgcaccgac tagacacaca    7020
aagcagttga atttttatat atatatctgt atattgcaca attataaact cattttgctt    7080
gtggctccac acacacaaaa aaagacctgt taaaattata cctgttgctt aattacaata    7140
tttctgataa ccatagcata ggacaaggga aaataaaaaa agaaaaaaaa gaaaaaaaa     7200
cgacaaatct gtctgctggt cacttcttct gtccaagcag attcgtggtc ttttcctcgc    7260
ttctttcaag ggcttttcctg tgccaggtga aggaggctcc aggcagcacc caggttttgc   7320
actcttgttt ctcccgtgct tgtgaaagag gtcccaaggt tctgggtgca ggagcgctcc    7380
cttgacctgc tgaagtccgg aacgtagtcg gcacagcctg gtcgccttcc acctctggga    7440
gctggagtcc actggggtgg cctgactccc ccagtcccct tcccgtgacc tggtcagggt    7500
gagcccatgt ggagtcagcc tcgcaggcct ccctgccagt agggtccgag tgtgtttcat    7560
ccttcccact ctgtcgagcc tggggggctgg agcggagacg ggaggcctgg cctgtctcgg   7620
aacctgtgag ctgcaccagg tagaacgcca gggaccccag aatcatgtgc gtcagtccaa    7680
ggggtcccct ccaggagtag tgaagactcc agaaatgtcc ctttcttctc ccccatccta    7740
cgagtaattg catttgcttt tgtaattctt aatgagcaat atctgctaga gagtttagct    7800
gtaacagttc ttttttgatca tcttttttta ataattagaa acaccaaaaa aatccagaaa    7860
cttgttcttc caaagcagag agcattataa tcaccagggc caaaagcttc cctccctgct    7920
gtcattgctt cttctgaggc ctgaatccaa aagaaaaaca gccataggcc ctttcagtgg    7980
ccgggctacc cgtgagccct tcggaggacc agggctgggg cagcctctgg gcccacatcc    8040
ggggccagct ccggcgtgtg ttcagtgtta gcagtgggtc atgatgctct tcccaccca     8100
gcctgggata ggggcagagg aggcgaggag gccgttgccg ctgatgtttg gccgtgaaca    8160
ggtgggtgtc tgcgtgcgtc cacgtgcgtg ttttctgact gacatgaaat cgacgcccga    8220
gttagcctca cccggtgacc tctagccctg cccggatgga gcggggccca cccggttcag    8280
tgtttctggg gagctggaca gtggagtgca aaaggcttgc agaacttgaa gcctgctcct    8340
tcccttgcta ccacggcctc ctttccgttt gatttgtcac tgcttcaatc aataacagcc    8400
gctccagagt cagtagtcaa tgaatatatg accaaatatc accaggactg ttactcaatg    8460
tgtgccgagc ccttgcccat gctgggctcc cgtgtatctg gacactgtaa cgtgtgctgt    8520
gtttgctccc cttcccttc cttctttgcc ctttacttgt cttttctgggg ttttttctgtt   8580
tgggtttggt ttggtttta tttctccttt tgtgttccaa acatgaggtt ctctctactg    8640
gtcctcttaa ctgtggtgtt gaggcttata tttgtgtaat ttttggtggg tgaaaggaat    8700
tttgctaagt aaatctcttc tgtgtttgaa ctgaagtctg tattgtaact atgtttaaag    8760
taattgttcc agagacaaat atttctagac acttttttctt tacaaacaaa agcattcgga   8820
gggaggggga tggtgactga gatgagaggg gagagctgaa cagatgaccc ctgcccagat    8880
cagccagaag ccacccaaag cagtggagcc caggagtccc actccaagcc agcaagccga    8940
atagctgatg tgttgccact ttccaagtca ctgcaaaacc aggttttgtt ccgcccagtg    9000
```

| | |
|---|---|
| gattcttgtt ttgcttcccc tcccccgag attattacca ccatcccgtg cttttaagga | 9060 |
| aaggcaagat tgatgtttcc ttgagggag ccaggagggg atgtgtgtgt gcagagctga | 9120 |
| agagctgggg agaatgggc tgggcccacc caagcaggag gctggacgc tctgctgtgg | 9180 |
| gcacaggtca ggctaatgtt ggcagatgca gctcttcctg acaggccag gtggtgggca | 9240 |
| ttctctctcc aaggtgtgcc ccgtgggcat tactgtttaa gacacttccg tcacatccca | 9300 |
| ccccatcctc cagggctcaa cactgtgaca tctctattcc ccaccctccc cttcccaggg | 9360 |
| caataaaatg accatggagg gggcttgcac tctcttggct gtcacccgat cgccagcaaa | 9420 |
| acttagatgt gagaaaaccc cttcccattc catggcgaaa acatctcctt agaaaagcca | 9480 |
| ttaccctcat taggcatggt tttgggctcc caaaacacct gacagcccct ccctcctctg | 9540 |
| agaggcggag agtgctgact gtagtgacca ttgcatgccg ggtgcagcat ctggaagagc | 9600 |
| taggcagggt gtctgcccc tcctgagttg aagtcatgct cccctgtgcc agcccagagg | 9660 |
| ccgagagcta tggacagcat tgccagtaac acaggccacc ctgtgcagaa gggagctggc | 9720 |
| tccagcctgg aaacctgtct gaggttggga gaggtgcact tggggcacag ggagaggccg | 9780 |
| ggacacactt agctggagat gtctctaaaa gccctgtatc gtattcacct tcagtttttg | 9840 |
| tgttttggga caattacttt agaaaataag taggtcgttt taaaaacaaa aattattgat | 9900 |
| tgcttttttg tagtgttcag aaaaaaggtt ctttgtgtat agccaaatga ctgaaagcac | 9960 |
| tgatatattt aaaaacaaaa ggcaatttat taaggaaatt tgtaccattt cagtaaacct | 10020 |
| gtctgaatgt acctgtatac gtttcaaaaa cacccccccc ccactgaatc cctgtaacct | 10080 |
| atttattata taaagagttt gccttataaa ttt | 10113 |

<210> SEQ ID NO 23
<211> LENGTH: 10182
<212> TYPE: DNA
<213> ORGANISM: Homo sapiens

<400> SEQUENCE: 23

| | |
|---|---|
| ccggaaattg gccgccgccg ccgccgccgc gccgagcgga ggaggaggag gaggcgagga | 60 |
| ggagagactg ctccataaaa atacagactc accagttcct gctttgatgt gacatgtgac | 120 |
| tccccagaat acaccttgct tctgtagacc agctccaaca ggattccatg gtagctggga | 180 |
| tgttagggct cagggaagaa aagtcagaag accaggacct ccagggcctc aaggacaaac | 240 |
| ccctcaagtt taaaaaggtg aagaaagata agaaagaaga gaaagagggc aagcatgagc | 300 |
| ccgtgcagcc atcagcccac cactctgctg agcccgcaga ggcaggcaaa gcagagacat | 360 |
| cagaagggtc aggctccgcc ccggctgtgc cggaagcttc tgcctccccc aaacagcggc | 420 |
| gctccatcat ccgtgaccgg ggacccatgt atgatgaccc caccctgcct gaaggctgga | 480 |
| cacggaagct taagcaaagg aaatctggcc gctctgctgg gaagtatgat gtgtatttga | 540 |
| tcaatcccca gggaaaagcc tttcgctcta agtggagtt gattgcgtac ttcgaaaagg | 600 |
| taggcgacac atccctggac cctaatgatt ttgacttcac ggtaactggg agggagcc | 660 |
| cctcccggcg agagcagaaa ccacctaaga agcccaaatc tcccaaagct ccaggaactg | 720 |
| gcagaggccg ggacgcccc aagggagcg gcaccacgag acccaaggcg gccacgtcag | 780 |
| agggtgtgca ggtgaaaagg gtcctggaga aaagtcctgg gaagtccctt gtcaagatgc | 840 |
| cttttcaaac ttcgccaggg gcaaggctg aggggggtgg ggccaccaca tccacccagg | 900 |
| tcatggtgat caaacgcccc ggcaggaagc gaaaagctga ggccgaccct caggccattc | 960 |
| ccaagaaacg gggccgaaag ccggggagtg tggtggcagc cgctgccgcc gaggccaaaa | 1020 |

-continued

```
agaaagccgt gaaggagtct tctatccgat ctgtgcagga gaccgtactc cccatcaaga    1080
agcgcaagac ccgggagacg gtcagcatcg aggtcaagga agtggtgaag cccctgctgg    1140
tgtccaccct cggtgagaag agcgggaaag gactgaagac ctgtaagagc cctgggcgga    1200
aaagcaagga gagcagcccc aaggggcgca gcagcagcgc ctcctcaccc cccaagaagg    1260
agcaccacca ccatcaccac cactcagagt ccccaaaggc cccgtgcca ctgctcccac     1320 ccctgccccc acctccacct gagcccgaga gctccgagga ccccaccagc cccctgagc    1380 cccaggactt gagcagcagc gtctgcaaag aggagaagat gccagagga ggctcactgg     1440 agagcgacgg ctgccccaag gagccagcta agactcagcc cgcggttgcc accgccgcca    1500
cggccgcaga aaagtacaaa caccgagggg agggagagcg caaagacatt gtttcatcct    1560
ccatgccaag gccaaacaga gaggagcctg tggacagccg gacgcccgtg accgagagag    1620
ttagctgact ttacacggag cggattgcaa agcaaaccaa caagaataaa ggcagctgtt    1680
gtctcttctc cttatgggta gggctctgac aaagcttccc gattaactga aataaaaaat    1740
attttttttt ctttcagtaa acttagagtt tcgtggcttc agggtgggag tagttggagc    1800
attggggatg ttttcttac cgacaagcac agtcaggttg aagacctaac cagggccaga    1860
agtagctttg cacttttcta aactaggctc cttcaacaag gcttgctgca gatactactg    1920
accagacaag ctgttgacca ggcacctccc ctcccgccca aaccttccc ccatgtggtc     1980 gttagagaca gagcgacaga gcagttgaga ggacactccc gttttcggtg ccatcagtgc    2040
cccgtctaca gctcccccag ctcccccac ctcccccact cccaaccacg ttgggacagg     2100
gaggtgtgag gcaggagaga cagttggatt ctttagagaa gatggatatg accagtggct    2160
atggcctgtg cgatcccacc cgtggtggct caagtctggc cccacaccag ccccaatcca    2220
aaactggcaa ggacgcttca caggacagga aagtggcacc tgtctgctcc agctctggca    2280
tggctaggag gggggagtcc cttgaactac tgggtgtaga ctggcctgaa ccacaggaga    2340
ggatggccca gggtgaggtg gcatggtcca ttctcaaggg acgtcctcca acgggtggcg    2400
ctagaggcca tggaggcagt aggacaaggt gcaggcaggc tggcctgggg tcaggccggg    2460
cagagcacag cggggtgaga gggattccta atcactcaga gcagtctgtg acttagtgga    2520
caggggaggg ggcaaagggg gaggagaaga aaatgttctt ccagttactt tccaattctc    2580
ctttagggac agcttagaat tatttgcact attgagtctt catgttccca cttcaaaaca    2640
aacagatgct ctgagagcaa actggcttga attggtgaca tttagtccct caagccacca    2700
gatgtgacag tgttgagaac tacctggatt tgtatatata cctgcgcttg ttttaaagtg    2760
ggctcagcac atagggttcc cacgaagctc cgaaactcta agtgtttgct gcaattttat    2820
aaggacttcc tgattggttt ctcttctccc cttccatttc tgccttttgt tcatttcatc    2880
ctttcacttc tttcccttcc tccgtcctcc tccttcctag ttcatccctt ctcttccagg    2940
cagccgcggt gcccaaccac acttgtcggc tccagtcccc agaactctgc ctgccctttg    3000
tcctcctgct gccagtacca gccccaccct gttttgagcc ctgaggaggc cttgggctct    3060
gctgagtccg acctggcctg tctgtgaaga gcaagagagc agcaaggtct tgctctccta    3120
ggtagccccc tcttccctgg taagaaaaag caaaaggcat ttcccaccct gaacaacgag    3180
ccttttcacc cttctactct agagaagtgg actggaggag ctgggcccga tttggtagtt    3240
gaggaaagca cagaggcctc ctgtggcctg ccagtcatcg agtggcccaa caggggctcc    3300
atgccagccg accttgacct cactcagaag tccagagtct agcgtagtgc agcagggcag    3360
```

```
tagcggtacc aatgcagaac tcccaagacc cgagctggga ccagtacctg ggtccccagc  3420
ccttcctctg ctcccccttt tccctcggag ttcttcttga atggcaatgt tttgcttttg  3480
ctcgatgcag acaggggcc agaacaccac acatttcact gtctgtctgg tccatagctg  3540
tggtgtaggg gctagaggc atgggcttgc tgtgggtttt taattgatca gttttcatgt  3600
gggatcccat cttttaacc tctgttcagg aagtccttat ctagctgcat atcttcatca  3660
tattggtata tccttttctg tgtttacaga gatgtctctt atatctaaat ctgtccaact  3720
gagaagtacc ttatcaaagt agcaaatgag acagcagtct tatgcttcca gaaacaccca  3780
caggcatgtc ccatgtgagc tgctgccatg aactgtcaag tgtgtgttgt cttgtgtatt  3840
tcagttattg tccctggctt ccttactatg gtgtaatcat gaaggagtga acatcatag  3900 aaactgtcta gcacttcctt gccagtcttt agtgatcagg aaccatagtt gacagttcca  3960
atcagtagct taagaaaaaa ccgtgtttgt ctcttctgga atggttagaa gtgagggagt  4020
ttgccccgtt ctgtttgtag agtctcatag ttggactttc tagcatatat gtgtccattt  4080
ccttatgctg taaaagcaag tcctgcaacc aaactcccat cagcccaatc cctgatccct  4140
gatcccttcc acctgctctg ctgatgaccc cccagcttc acttctgact cttccccagg  4200
aagggaaggg gggtcagaag agagggtgag tcctccagaa ctcttcctcc aaggacagaa  4260
ggctcctgcc cccatagtgg cctcgaactc ctggcactac caaaggacac ttatccacga  4320
gagcgcagca tccgaccagg ttgtcactga aagatgtttt attttggtca gttgggtttt  4380
tatgtattat acttagtcaa atgtaatgtg gcttctggaa tcattgtcca gagctgcttc  4440
cccgtcacct gggcgtcatc tggtcctggt aagaggagtg cgtggcccac caggccccc  4500 tgtcacccat gacagttcat tcagggccga tggggcagtc gtggttggga acacagcatt  4560
tcaagcgtca ctttatttca ttcgggcccc acctgcagct ccctcaaaga ggcagttgcc  4620
cagcctcttt cccttccagt ttattccaga gctgccagtg gggcctgagg ctccttaggg  4680
ttttctctct atttccccct ttcttcctca ttccctcgtc tttcccaaag gcatcacgag  4740
tcagtcgcct ttcagcaggc agccttggcg gtttatcgcc ctggcaggca ggggccctgc  4800
agctctcatg ctgcccctgc cttggggtca ggttgacagg aggttggagg gaaagcctta  4860
agctgcagga ttctcaccag ctgtgtccgg cccagttttg gggtgtgacc tcaatttcaa  4920
ttttgtctgt acttgaacat tatgaagatg ggggcctctt tcagtgaatt tgtgaacagc  4980
agaattgacc gacagctttc cagtacccat ggggctaggt cattaaggcc acatccacag  5040
tctcccccac ccttgttcca gttgttagtt actacctcct ctcctgacaa tactgtatgt  5100
cgtcgagctc ccccaggtc taccctccc ggccctgcct gctggtgggc ttgtcatagc  5160
cagtgggatt gccggtcttg acagctcagt gagctggaga tacttggtca cagccaggcg  5220
ctagcacagc tcccttctgt tgatgctgta ttcccatatc aaaagacaca ggggacaccc  5280
agaaacgcca catcccccaa tccatcagtg ccaaactagc caacgcccc agcttctcag  5340 ctcgctggat ggcggaagct gctactcgtg agcgccagtg cgggtgcaga caatcttctg  5400
ttgggtggca tcattccagg cccgaagcat gaacagtgca cctgggacag ggagcagccc  5460
caaattgtca cctgcttctc tgcccagctt ttcattgctg tgacagtgat ggcgaaagag  5520
ggtaataacc agacacaaac tgccaagttg ggtggagaaa ggagtttctt tagctgcacag  5580 aatctctgaa ttttaaatca cttagtaagc ggctcaagcc caggagggag cagagggata  5640
cgagcggagt cccctgcgcg ggaccatctg gaattggttt agcccaagtg gagcctgaca  5700
gccagaactc tgtgtccccc gtctaaccac agctccttt ccagagcatt ccagtcaggc  5760
```

```
tctctgggct gactgggcca ggggaggtta caggtaccag ttctttaaga agatctttgg    5820
gcatatacat ttttagcctg tgtcattgcc ccaaatggat tcctgtttca agttcacacc    5880
tgcagattct aggacctgtg tcctagactt caggagtca gctgtttcta gagttcctac     5940
catggagtgg gtctggagga cctgcccggt ggggggcag agccctgctc cctccgggtc     6000
ttcctactct tctctctgct ctgacgggat ttgttgattc tctccatttt ggtgtctttc    6060
tcttttagat attgtatcaa tctttagaaa aggcatagtc tacttgttat aaatcgttag    6120
gatactgcct cccccagggt ctaaaattac atattgagg ggaaaagctg aacactgaag     6180
tcagttctca acaatttaga aggaaaacct agaaaacatt tggcagaaaa ttacatttcg    6240 atgttttga tgaatacga gcaagctttt acaacagtgc tgatctaaaa atacttagca     6300
cttggcctga gatgcctggt gagcattaca ggcaagggga atctggaggt agccgacctg   6360
aggacatggc ttctgaacct gtcttttggg agtggtatgg aaggtggagc gttcaccagt   6420
gacctggaag gcccagcacc accctccttc ccactcttct catcttgaca gagcctgccc   6480
cagcgctgac gtgtcaggaa aacacccagg gaactaggaa ggcacttctg cctgaggggc   6540
agcctgcctt gcccactcct gctctgctcg cctcggatca gctgagcctt ctgagctggc   6600
ctctcactgc ctccccaagg ccccctgcct gccctgtcag gaggcagaag gaagcaggtg   6660
tgagggcagt gcaaggaggg agcacaaccc ccagctcccg ctccgggctc cgacttgtgc   6720
acaggcagag cccagaccct ggaggaaatc ctacctttga attcaagaac atttggggaa   6780 tttgaaatc tctttgcccc caaaccccca ttctgtccta cctttaatca ggtcctgctc    6840
agcagtgaga gcagatgagg tgaaaaggcc aagaggtttg gctcctgccc actgatagcc   6900
cctctccccg cagtgtttgt gtgtcaagtg gcaaagctgt tcttcctggt gaccctgatt   6960
atatccagta acacatagac tgtgcgcata ggcctgcttt gtctcctcta tcctgggctt   7020
ttgttttgct ttttagtttt gcttttagtt tttctgtccc ttttatttaa cgcaccgact   7080
agacacacaa agcagttgaa ttttatata tatatctgta tattgcacaa ttataaactc    7140
attttgcttg tggctccaca cacacaaaaa aagacctgtt aaaattatac ctgttgctta   7200
attacaatat ttctgataac catagcatag acaagggaa aataaaaaaa gaaaaaaaag    7260
aaaaaaaaac gacaaatctg tctgctggtc acttcttctg tccaagcaga ttcgtggtct   7320
tttcctcgct tctttcaagg gctttcctgt gccaggtgaa ggaggctcca ggcagcaccc   7380
aggttttgca ctcttgtttc tcccgtgctt gtgaaagagg tcccaaggtt ctgggtgcag   7440
gagcgctccc ttgacctgct gaagtccgga acgtagtcgg cacagcctgg tcgccttcca   7500
cctctgggag ctgagtcca ctggggtggc ctgactcccc cagtcccctt cccgtgacct    7560
ggtcagggtg agcccatgtg gagtcagcct cgcaggcctc cctgccagta gggtccgagt   7620
gtgtttcatc cttcccactc tgtcgagcct ggggctgga gcggagacgg gaggcctggc    7680
ctgtctcgga acctgtgagc tgcaccaggt agaacgccag ggaccccaga atcatgtgcg   7740
tcagtccaag gggtcccctc caggagtagt gaagactcca gaaatgtccc tttcttctcc   7800
cccatcctac gagtaattgc atttgctttt gtaattctta atgagcaata tctgctagag   7860
agtttagctg taacagttct ttttgatcat cttttttaa taattagaaa caccaaaaaa    7920
atccagaaac ttgttcttcc aaagcagaga gcattataat caccagggcc aaaagcttcc   7980
ctccctgctg tcattgcttc ttctgaggcc tgaatccaaa agaaaaacag ccataggccc   8040
tttcagtggc cgggctaccc gtgagccctt cggaggacca gggctgggc agcctctggg     8100
```

```
cccacatccg gggccagctc cggcgtgtgt tcagtgttag cagtgggtca tgatgctctt    8160
tcccacccag cctgggatag gggcagagga ggcgaggagg ccgttgccgc tgatgtttgg    8220
ccgtgaacag gtgggtgtct gcgtgcgtcc acgtgcgtgt tttctgactg acatgaaatc    8280
gacgcccgag ttagcctcac ccggtgacct ctagccctgc ccggatggag cggggcccac    8340
ccggttcagt gtttctgggg agctggacag tggagtgcaa aaggcttgca gaacttgaag    8400
cctgctcctt cccttgctac cacggcctcc tttccgtttg atttgtcact gcttcaatca    8460
ataacagccg ctccagagtc agtagtcaat gaatatatga ccaaatatca ccaggactgt    8520
tactcaatgt gtgccgagcc cttgcccatg ctgggctccc gtgtatctgg acactgtaac    8580
gtgtgctgtg tttgctcccc ttccccttcc ttctttgccc tttacttgtc tttctggggt    8640
ttttctgttt gggtttggtt tggttttat ttctcctttt gtgttccaaa catgaggttc    8700
tctctactgg tcctcttaac tgtggtgttg aggcttatat ttgtgtaatt tttggtgggt    8760
gaaaggaatt ttgctaagta aatctcttct gtgtttgaac tgaagtctgt attgtaacta    8820
tgtttaaagt aattgttcca gagacaaata tttctagaca cttttttcttt acaaacaaaa    8880
gcattcggag ggagggggat ggtgactgag atgagagggg agagctgaac agatgacccc    8940
tgcccagatc agccagaagc cacccaaagc agtggagccc aggagtccca ctccaagcca    9000
gcaagccgaa tagctgatgt gttgccactt tccaagtcac tgcaaaacca ggttttgttc    9060
cgcccagtgg attcttgttt tgcttcccct cccccgaga ttattaccac catcccgtgc    9120
ttttaaggaa aggcaagatt gatgtttcct tgagggagc caggagggga tgtgtgtgtg    9180
cagagctgaa gagctgggga gaatgggcct gggcccaccc aagcaggagg ctgggacgct    9240
ctgctgtggg cacaggtcag gctaatgttg gcagatgcag ctcttcctgg acaggccagg    9300
tggtgggcat tctctctcca aggtgtgccc cgtgggcatt actgtttaag cacttccgt    9360
cacatcccac cccatcctcc agggctcaac actgtgacat ctctattccc caccctcccc    9420
ttcccagggc aataaaatga ccatggaggg ggcttgcact ctcttggctg tcacccgatc    9480
gccagcaaaa cttagatgtg agaaaacccc ttcccattcc atggcgaaaa catctcctta    9540
gaaaagccat taccctcatt aggcatggtt ttgggctccc aaaacacctg acagcccctc    9600
cctcctctga gaggcggaga gtgctgactg tagtgaccat tgcatgccgg gtgcagcatc    9660
tggaagagct aggcagggtg tctgccccct cctgagttga agtcatgctc ccctgtgcca    9720
gcccagaggc cgagagctat ggacagcatt gccagtaaca caggccaccc tgtgcagaag    9780
ggagctggct ccagcctgga aacctgtctg aggttgggag aggtgcactt ggggcacagg    9840
gagaggccgg gacacactta gctggagatg tctctaaaag ccctgtatcg tattcacctt    9900
cagttttgt gttttgggac aattacttta gaaataagt aggtcgtttt aaaaacaaaa    9960
attattgatt gcttttttgt agtgttcaga aaaaggttc tttgtgtata gccaaatgac   10020
tgaaagcact gatatattta aaaacaaaag gcaatttatt aaggaaattt gtaccatttc   10080
agtaaacctg tctgaatgta cctgtatacg tttcaaaaac ccccccccc cactgaatcc   10140
ctgtaaccta tttattatat aaagagtttg ccttataaat tt                      10182
```

<210> SEQ ID NO 24
<211> LENGTH: 10180
<212> TYPE: DNA
<213> ORGANISM: Homo sapiens

<400> SEQUENCE: 24

```
ccggaaaatg gccgccgccg ccgccgccgc gccgagcgga ggaggaggag gaggcgagga      60
```

```
ggagagacct ccataaaaat acagactcac cagttcctgc tttgatgtga catgtgactc    120
cccagaatac accttgcttc tgtagaccag ctccaacagg attccatggt agctgggatg    180
ttagggctca gggaagaaaa gtcagaagac caggacctcc agggcctcaa ggacaaaccc    240
ctcaagttta aaaggtgaa gaaagataag aaagaagaga aagagggcaa gcatgagccc     300
gtgcagccat cagcccacca ctctgctgag cccgcagagg caggcaaagc agagacatca    360
gaagggtcag gctccgcccc ggctgtgccg gaagcttctg cctcccccaa acagcggcgc    420
tccatcatcc gtgaccgggg acccatgtat gatgacccca ccctgcctga aggctggaca    480
cggaagctta agcaaaggaa atctggccgc tctgctggga agtatgatgt gtatttgatc    540
aatccccagg gaaaagcctt tcgctctaaa gtggagttga ttgcgtactt cgaaaaggta    600
ggcgacacat ccctggaccc taatgatttt gacttcacgg taactgggag agggagcccc    660
tcccggcgag agcagaaacc acctaagaag cccaaatctc ccaaagctcc aggaactggc    720
agaggccggg gacgcccaa agggagcggc accacgagac caaggcggc cacgtcagag    780 ggtgtgcagg tgaaaagggt cctggagaaa agtcctggga agctccttgt caagatgcct    840
tttcaaactt cgccaggggg caaggctgag ggggtgggg ccaccacatc cacccaggtc     900
atggtgatca acgcccggg caggaagcga aaagctgagg ccgaccctca ggccattccc    960
aagaaacggg gccgaaagcc ggggagtgtg gtggcagccg ctgccgccga ggccaaaaag    1020
aaagccgtga aggagtcttc tatccgatct gtgcaggaga ccgtactccc catcaagaag    1080
cgcaagaccc gggagacggt cagcatcgag gtcaaggaag tggtgaagcc cctgctggtg    1140
tccacgctcg gtgagaagag cgggaaagga ctgaagacct gtaagagccc tgggcggaaa    1200
agcaaggaga gcagccccaa gggcgcagc agcagcgcct cctcacccc caagaaggag      1260 caccaccacc atcaccacca ctcagagtcc ccaaaggccc ccgtgccact gctcccaccc    1320
ctgcccccac ctccacctga gcccgagagc tccgaggacc ccaccagccc cctgagcccc    1380
caggacttga gcagcagcgt ctgcaaagag gagaagatgc ccagaggagg ctcactggag    1440
agcgacggct gccccaagga gccagctaag actcagcccg cggttgccac cgccgccacg    1500
gccgcagaaa agtacaaaca ccgagggag ggagagcgca agacattgt ttcatcctcc      1560 atgccaaggc caaacagaga ggagcctgtg acagccgga cgcccgtgac cgagagagtt     1620
agctgacttt acacggagcg gattgcaaag caaaccaaca agaataaagg cagctgttgt    1680
ctcttctcct tatgggtagg gctctgacaa agcttcccga ttaactgaaa taaaaaatat    1740
ttttttttct ttcagtaaac ttagagtttc gtggcttcag ggtgggagta gttggagcat    1800 tgggatgtt tttcttaccg acaagcacag tcaggttgaa gacctaacca gggccagaag     1860
tagctttgca cttttctaaa ctaggctcct tcaacaaggc ttgctgcaga tactactgac    1920
cagacaagct gttgaccagg cacctcccct cccgcccaaa cctttccccc atgtggtcgt    1980
tagagacaga gcgacagagc agttgagagg acactcccgt tttcggtgcc atcagtgccc    2040
cgtctacagc tccccagct cccccacct cccccactcc caaccacgtt gggacaggga      2100
ggtgtgaggc aggagagaca gttggattct ttagagaaga tggatatgac cagtggctat    2160
ggcctgtgcg atcccacccg tgtggctca agtctggccc cacaccagcc ccaatccaaa     2220 actgcaagg acgcttcaca ggacaggaaa gtggcacctg tctgctccag ctctggcatg     2280
gctaggaggg gggagtccct tgaactactg ggtgtagact ggcctgaacc acaggagagg    2340
atggcccagg gtgaggtggc atggtccatt ctcaagggac gtcctccaac gggtggcgct    2400
```

```
agaggccatg gaggcagtag gacaaggtgc aggcaggctg gcctggggtc aggccgggca   2460
gagcacagcg gggtgagagg gattcctaat cactcagagc agtctgtgac ttagtggaca   2520 ggggagggggg caaagggggga ggagaagaaa atgttcttcc agttactttc caattctcct   2580
ttagggacag cttagaatta tttgcactat tgagtcttca tgttcccact tcaaaacaaa   2640
cagatgctct gagagcaaac tggcttgaat tggtgacatt tagtccctca agccaccaga   2700
tgtgacagtg ttgagaacta cctggatttg tatatatacc tgcgcttgtt ttaaagtggg   2760
ctcagcacat agggttccca cgaagctccg aaactctaag tgtttgctgc aattttataa   2820
ggacttcctg attggtttct cttctcccct tccattctg ccttttgttc atttcatcct   2880
ttcacttctt tcccttcctc cgtcctcctc cttcctagtt catcccttct cttccaggca   2940
gccgcggtgc ccaaccacac ttgtcggctc cagtccccag aactctgcct gcccttttgtc   3000 ctcctgctgc cagtaccagc cccaccctgt tttgagccct gaggaggcct tgggctctgc   3060
tgagtccgac ctggcctgtc tgtgaagagc aagagagcca caaggtcttg ctctcctagg   3120
tagccccctc ttccctggta agaaaaagca aaaggcattt cccaccctga caacgagcc   3180 ttttcacccct tctactctag agaagtggac tggaggagct gggcccgatt tggtagttga   3240
ggaaagcaca gaggcctcct gtggcctgcc agtcatcgag tggcccaaca ggggctccat   3300
gccagccgac cttgacctca ctcagaagtc cagagtctag cgtagtgcag cagggcagta   3360
gcggtaccaa tgcagaactc ccaagacccg agctgggacc agtacctggg tccccagccc   3420
ttcctctgct cccccttttc cctcggagtt cttcttgaat ggcaatgttt tgcttttgct   3480
cgatgcagac agggggccag aacaccacac atttcactgt ctgtctggtc catagctgtg   3540
gtgtaggggc ttagaggcat gggcttgctg tgggttttta attgatcagt tttcatgtgg   3600
gatcccatct ttttaacctc tgttcaggaa gtccttatct agctgcatat cttcatcata   3660
ttggtatatc ctttctgtg tttacagaga tgtctcttat atctaaatct gtccaactga   3720
gaagtacctt atcaaagtag caaatgagac agcagtctta tgcttccaga aacacccaca   3780
ggcatgtccc atgtgagctg ctgccatgaa ctgtcaagtg tgtgttgtct tgtgtatttc   3840
agttattgtc cctggcttcc ttactatggt gtaatcatga aggagtgaaa catcatagaa   3900
actgtctagc acttccttgc cagtctttag tgatcaggaa ccatagttga cagttccaat   3960
cagtagctta agaaaaaacc gtgtttgtct cttctggaat ggttagaagt gagggagttt   4020
gccccgttct gtttgtagag tctcatagtt ggactttcta gcatatatgt gtccatttcc   4080
ttatgctgta aaagcaagtc ctgcaaccaa actcccatca gcccaatccc tgatccctga   4140
tcccttccac ctgctctgct gatgaccccc ccagcttcac ttctgactct tccccaggaa   4200
gggaaggggg gtcagaagag agggtgagtc ctccagaact cttcctccaa ggacagaagg   4260
ctcctgcccc catagtggcc tcgaactcct ggcactacca aaggacactt atccacgaga   4320
gcgcagcatc cgaccaggtt gtcactgaga agatgtttat tttggtcagt tgggtttta   4380 tgtattatac ttagtcaaat gtaatgtggc ttctggaatc attgtccaga gctgcttccc   4440
cgtcacctgg gcgtcatctg gtcctggtaa gaggagtgcg tggcccacca ggccccctg   4500 tcacccatga cagttcattc agggccgatg gggcagtcgt ggttgggaac acagcatttc   4560
aagcgtcact ttatttcatt cgggcccac ctgcagctcc ctcaaagagg cagttgccca   4620
gcctctttcc cttccagttt attccagagc tgccagtggg gcctgaggct ccttagggtt   4680
ttctctctat ttcccccttt cttcctcatt ccctcgtctt tcccaaaggc atcacgagtc   4740
agtcgccttt cagcaggcag ccttggcggt ttatcgccct ggcaggcagg ggccctgcag   4800
```

-continued

```
ctctcatgct gccccrgcct tggggtcagg ttgacaggag gttggaggga aagccttaag    4860
ctgcaggatt ctcaccagct gtgtccggcc cagttttggg gtgtgacctc aatttcaatt    4920
ttgtctgtac ttgaacatta tgaagatggg ggcctctttc agtgaatttg tgaacagcag    4980
aattgaccga cagcttttcca gtacccatgg ggctaggtca ttaaggccac atccacagtc   5040
tccccaccc ttgttccagt tgttagttac tacctcctct cctgacaata ctgtatgtcg     5100
tcgagctccc cccaggtcta cccctcccgg ccctgcctgc tggtgggctt gtcatagcca    5160
gtgggattgc cggtcttgac agctcagtga gctggagata cttggtcaca gccaggcgct    5220
agcacagctc ccttctgttg atgctgtatt cccatatcaa aagacacagg ggacacccag    5280
aaacgccaca tccccaatc catcagtgcc aaactagcca acggcccag cttctcagct      5340
cgctggatgg cggaagctgc tactcgtgag cgccagtgcg ggtgcagaca atcttctgtt    5400
gggtggcatc attccaggcc cgaagcatga acagtgcacc tgggacaggg agcagcccca    5460
aattgtcacc tgcttctctg cccagctttt cattgctgtg acagtgatgg cgaaagaggg    5520
taataaccag acacaaactg ccaagttggg tggagaaagg agtttcttta gctgacagaa    5580
tctctgaatt ttaaatcact tagtaagcgg ctcaagccca ggagggagca gagggatacg    5640
agcggagtcc cctgcgcggg accatctgga attggtttag cccaagtgga gcctgacagc    5700
cagaactctg tgtccccgt ctaaccacag ctccttttcc agagcattcc agtcaggctc     5760
tctgggctga ctgggccagg ggaggttaca ggtaccagtt ctttaagaag atctttgggc    5820
atatacattt ttagcctgtg tcattgcccc aaatggattc ctgtttcaag ttcacacctg    5880
cagattctag gacctgtgtc ctagacttca gggagtcagc tgtttctaga gttcctacca    5940
tggagtgggt ctgaggacc tgcccggtgg ggggcagag ccctgctccc tccgggtctt      6000
cctactcttc tctctgctct gacgggattt gttgattctc tccatttttgg tgtctttctc   6060
ttttagatat tgtatcaatc tttagaaaag gcatagtcta cttgttataa atcgttagga    6120
tactgcctcc cccagggtct aaaattacat attgaggggg aaaagctgaa cactgaagtc    6180
agttctcaac aatttagaag gaaaacctag aaaacattttg gcagaaaatt acatttcgat   6240
gtttttgaat gaatacgagc aagcttttac aacagtgctg atctaaaaat acttagcact    6300
tggcctgaga tgcctggtga gcattacagg caaggggaat ctggaggtag ccgacctgag    6360
gacatggctt ctgaacctgt cttttgggag tggtatggaa ggtggagcgt tcaccagtga    6420
cctggaaggc ccagcaccac cctccttccc actcttctca tcttgacaga gcctgcccca    6480
gcgctgacgt gtcaggaaaa cacccaggga actaggaagg cacttctgcc tgaggggcag    6540
cctgccttgc ccactcctgc tctgctcgcc tcggatcagc tgagccttct gagctggcct    6600
ctcactgcct ccccaaggcc cctgcctgc cctgtcagga ggcagaagga agcaggtgtg     6660
agggcagtgc aaggagggag cacaaccccc agctcccgct ccgggctccg acttgtgcac    6720
aggcagagcc cagaccctgg aggaaatcct acctttgaat tcaagaacat ttggggaatt    6780
tgaaatctc tttgcccca aacccccatt ctgtcctacc tttaatcagg tcctgctcag      6840
cagtgagagc agatgaggtg aaaaggccaa gaggtttggc tcctgcccac tgatagcccc    6900
tctccccgca gtgtttgtgt gtcaagtggc aaagctgttc ttcctggtga ccctgattat    6960
atccagtaac acatagactg tgcgcatagg cctgctttgt ctcctctatc ctgggctttt    7020
gttttgcttt ttagttttgc ttttagtttt tctgtccctt ttatttaacg caccgactag    7080
acacacaaag cagttgaatt tttatatata tatctgtata ttgcacaatt ataaactcat    7140
```

```
tttgcttgtg gctccacaca cacaaaaaaa gacctgttaa aattatacct gttgcttaat    7200
tacaatattt ctgataacca tagcatagga caagggaaaa taaaaaaaga aaaaaaagaa    7260
aaaaaaacga caaatctgtc tgctggtcac ttcttctgtc caagcagatt cgtggtcttt    7320
tcctcgcttc tttcaagggc tttcctgtgc caggtgaagg aggctccagg cagcacccag    7380
gttttgcact cttgtttctc ccgtgcttgt gaaagaggtc ccaaggttct gggtgcagga    7440
gcgctccctt gacctgctga agtccggaac gtagtcggca cagcctggtc gccttccacc    7500
tctgggagct ggagtccact ggggtggcct gactccccca gtccccttcc cgtgacctgg    7560
tcagggtgag cccatgtgga gtcagcctcg caggcctccc tgccagtagg gtccgagtgt    7620
gtttcatcct tcccactctg tcgagcctgg gggctggagc ggagacggga ggcctggcct    7680
gtctcggaac ctgtgagctg caccaggtag aacgccaggg accccagaat catgtgcgtc    7740
agtccaaggg gtcccctcca ggagtagtga agactccaga aatgtccctt tcttctcccc    7800
catcctacga gtaattgcat ttgcttttgt aattcttaat gagcaatatc tgctagagag    7860
tttagctgta acagttcttt ttgatcatct tttttaata attagaaaca ccaaaaaaat    7920
ccagaaactt gttcttccaa agcagagagc attataatca ccagggccaa aagcttccct    7980
ccctgctgtc attgcttctt ctgaggcctg aatccaaaag aaaaacagcc ataggccctt    8040
tcagtggccg ggctacccgt gagcccttcg gaggaccagg gctggggcag cctctgggcc    8100
cacatccggg gccagctccg gcgtgtgttc agtgttagca gtgggtcatg atgctctttc    8160
ccacccagcc tgggataggg gcagaggagg cgaggaggcc gttgccgctg atgtttggcc    8220
gtgaacaggt gggtgtctgc gtgcgtccac gtgcgtgttt tctgactgac atgaaatcga    8280
cgcccgagtt agcctcaccc ggtgacctct agccctgccc ggatggagcg gggcccaccc    8340
ggttcagtgt ttctggggag ctggacagtg gagtgcaaaa ggcttgcaga acttgaagcc    8400
tgctccttcc cttgctacca cggcctcctt tccgtttgat ttgtcactgc ttcaatcaat    8460
aacagccgct ccagagtcag tagtcaatga atatatgacc aaatatcacc aggactgtta    8520
ctcaatgtgt gccgagccct tgcccatgct gggctcccgt gtatctggac actgtaacgt    8580
gtgctgtgtt tgctccccctt cccttccctt tcttgcccct tacttgtctt tctggggttt    8640
ttctgtttgg gtttggtttg gtttttattt ctccttttgt gttccaaaca tgaggttctc    8700
tctactggtc ctcttaactg tggtgttgag gcttatattt gtgtaatttt tggtgggtga    8760
aaggaatttt gctaagtaaa tctcttctgt gtttgaactg aagtctgtat tgtaactatg    8820
tttaaagtaa ttgttccaga gacaaatatt tctagacact ttttctttac aaacaaaagc    8880
attcggaggg aggggatgg tgactgagat gagaggggag agctgaacag atgacccctg     8940
cccagatcag ccagaagcca cccaaagcag tggagcccag gagtcccact ccaagccagc    9000
aagccgaata gctgatgtgt tgccactttc caagtcactg caaaaccagg ttttgttccg    9060
cccagtggat tcttgttttg cttcccctcc ccccgagatt attaccacca tcccgtgctt    9120
ttaaggaaag gcaagattga tgtttccttg aggggagcca ggaggggatg tgtgtgtgca    9180
gagctgaaga gctggggaga atgggggctgg gcccacccaa gcaggaggct gggacgctct    9240
gctgtgggca caggtcaggc taatgttggc agatgcagct cttcctggac aggccaggtg    9300
gtgggcattc tctctccaag gtgtgccccg tgggcattac tgtttaagac acttccgtca    9360
catcccaccc catcctccag ggctcaacac tgtgacatct ctattcccca cctcccctt     9420
cccagggcaa taaaatgacc atggaggggg cttgcactct cttggctgtc acccgatcgc    9480
cagcaaaact tagatgtgag aaaaccccctt cccattccat ggcgaaaaca tctccttaga    9540
```

-continued

```
aaagccatta ccctcattag gcatggtttt gggctcccaa aacacctgac agccctccc      9600 tcctctgaga ggcggagagt gctgactgta gtgaccattg catgccgggt gcagcatctg      9660
gaagagctag gcagggtgtc tgcccctcc tgagttgaag tcatgctccc ctgtgccagc      9720
ccagaggccg agagctatgg acagcattgc cagtaacaca ggccaccctg tgcagaaggg      9780
agctggctcc agcctggaaa cctgtctgag gttgggagag gtgcacttgg ggcacaggga      9840
gaggccggga cacacttagc tggagatgtc tctaaaagcc ctgtatcgta ttcaccttca      9900 gttttgtgt tttgggacaa ttactttaga aataagtag gtcgttttaa aaacaaaaat      9960
tattgattgc ttttttgtag tgttcagaaa aaaggttctt tgtgtatagc caaatgactg     10020
aaagcactga tatatttaaa aacaaaaggc aatttattaa ggaaatttgt accatttcag     10080
taaacctgtc tgaatgtacc tgtatacgtt tcaaaaacac cccccccca ctgaatccct     10140 gtaacctatt tattatataa agagtttgcc ttataaattt                          10180
```

<210> SEQ ID NO 25
<211> LENGTH: 10191
<212> TYPE: DNA
<213> ORGANISM: Homo sapiens

<400> SEQUENCE: 25

```
ccggaaaatg gccgccgccg ccgccgccgc cgccgccgcg ccgagcggag gaggaggagg        60
aggcgaggag gagagactgc tccataaaaa tacagactca ccagttcctg ctttgatgtg      120
acatgtgact ccccagaata caccttgctt ctgtagacca gctccaacag gattccatgg      180
tagctgggat gttagggctc agggaagaaa agtcagaaga ccaggacctc cagggcctca      240
aggacaaacc cctcaagttt aaaaaggtga agaaagataa gaaagaagag aaagagggca      300
agcatgagcc cgtgcagcca tcagcccacc actctgctga gcccgcagag gcaggcaaag      360
cagagacatc agaagggtca ggctccgccc cggctgtgcc ggaagcttct gcctccccca      420
aacagcggcg ctccatcatc cgtgaccggg gacccatgta tgatgacccc accctgcctg      480
aaggctggac acgaagcttt aagcaaagga aatctggccg ctctgctggg aagtatgatg      540
tgtatttgat caatccccag ggaaaagcct ttcgctctaa agtggagttg attgcgtact      600
tcgaaaaggt aggcgacaca tccctggacc ctaatgattt tgacttcacg gtaactggga      660
gagggagccc ctcccggcga gagcagaaac cacctaagaa gcccaaatct cccaaagctc      720
caggaactgg cagaggccgg ggacgcccca agggagcgg caccacgaga cccaaggcgg      780
ccacgtcaga gggtgtgcag gtgaaaaggg tcctggagaa aagtcctggg aagctccttg      840
tcaagatgcc ttttcaaact tcgccagggg gcaaggctga gggggtggg gccaccacat      900 ccacccaggt catggtgatc aaacgccccg gcaggaagcg aaaagctgag gccgaccctc      960
aggccattcc caagaaacgg ggccgaaagc cgggagtgt ggtggcagcc gctgccgccg     1020
aggccaaaaa gaaagccgtg aaggagtctt ctatccgatc tgtgcaggag accgtactcc     1080
ccatcaagaa gcgcaagacc cgggagacgg tcagcatcga ggtcaaggaa gtggtgaagc     1140
ccctgctggt gtccaccctc ggtgagaaga gcgggaaagg actgaagacc tgtaagagcc     1200
ctgggcggaa aagcaaggag agcagcccca agggcgcag cagcagcgcc tcctcacccc     1260
ccaagaagga gcaccaccac catcaccacc actcagagtc cccaaaggcc cccgtgccac     1320
tgctcccacc cctgccccca cctccacctg agccccgagag ctccgaggac cccaccagcc     1380 ccctgagcc ccaggacttg agcagcagcg tctgcaaaga ggagaagatg cccagaggag     1440
```

```
gctcactgga gagcgacggc tgccccaagg agccagctaa gactcagccc gcggttgcca   1500
ccgccgccac ggccgcagaa aagtacaaac accgagggga gggagagcgc aaagacattg   1560
tttcatcctc catgccaagg ccaaacagag aggagcctgt ggacagccgg acgcccgtga   1620
ccgagagagt tagctgactt tacacggagc ggattgcaaa gcaaaccaac aagaataaag   1680
gcagctgttg tctcttctcc ttatgggtag ggctctgaca aagcttcccg attaactgaa   1740
ataaaaaata ttttttttc tttcagtaaa cttagagttt cgtggcttca gggtgggagt   1800
agttggagca ttggggatgt ttttcttacc gacaagcaca gtcaggttga agacctaacc   1860
agggccagaa gtagctttgc acttttctaa actaggctcc ttcaacaagg cttgctgcag   1920
atactactga ccagacaagc tgttgaccag gcacctcccc tcccgcccaa acctttcccc   1980
catgtggtcg ttagagacag agcgacagag cagttgagag gacactcccg ttttcggtgc   2040
catcagtgcc ccgtctacag ctcccccagc tcccccacc tcccccactc ccaaccacgt   2100
tgggacaggg aggtgtgagg caggagagac agttggattc tttagagaag atggatatga   2160
ccagtggcta tggcctgtgc gatcccaccc gtggtggctc aagtctggcc ccacaccagc   2220
cccaatccaa aactggcaag gacgcttcac aggacaggaa agtggcacct gtctgctcca   2280
gctctggcat ggctaggagg ggggagtccc ttgaactact gggtgtagac tggcctgaac   2340
cacaggagag gatgggccag ggtgaggtgg catggtccat tctcaaggga cgtcctccaa   2400
cgggtggcgc tagaggccat ggaggcagta ggacaaggtg caggcaggct ggcctggggt   2460
caggccgggc agagcacagc ggggtgagag ggattcctaa tcactcagag cagtctgtga   2520
cttagtggac aggggagggg gcaaaggggg aggagaagaa aatgttcttc cagttacttt   2580
ccaattctcc tttagggaca gcttagaatt atttgcacta ttgagtcttc atgttcccac   2640
ttcaaaacaa acagatgctc tgagagcaaa ctggcttgaa ttggtgacat ttagtccctc   2700
aagccaccag atgtgacagt gttgagaact acctggattt gtatatatac ctgcgcttgt   2760
tttaaagtgg gctcagcaca tagggttccc acgaagctcc gaaactctaa gtgtttgctg   2820
caattttata aggacttcct gattggtttc tcttctcccc ttccatttct gccttttgtt   2880
catttcatcc tttcacttct ttcccttcct ccgtcctcct ccttcctagt tcatcccttc   2940
tcttccaggc agccgcggtg cccaaccaca cttgtcggct ccagtcccca gaactctgcc   3000 tgcccttgt cctcctgctg ccagtaccag ccccaccctg ttttgagccc tgaggaggcc   3060
ttgggctctg ctgagtccga cctggcctgt ctgtgaagag caagagagca gcaaggtctt   3120
gctctcctag gtagccccct cttccctggt aagaaaaagc aaaaggcatt tcccaccctg   3180
aacaacgagc cttttcaccc ttctactcta gagaagtgga ctggaggagc tgggcccgat   3240
ttggtagttg aggaaagcac agaggcctcc tgtggcctgc cagtcatcga gtgcccaac    3300 agggggctcca tgccagccga ccttgacctc actcagaagt ccagagtcta gcgtagtgca   3360
gcagggcagt agcggtacca atgcagaact cccaagaccc gagctgggac cagtacctgg   3420
gtccccagcc cttcctctgc tcccccttt ccctcggagt tcttcttgaa tggcaatgtt   3480
ttgcttttgc tcgatgcaga caggggggcca gaacaccaca catttcactg tctgtctggt   3540
ccatagctgt ggtgtagggg cttagaggca tgggcttgct gtgggttttt aattgatcag   3600
ttttcatgtg ggatcccatc tttttaacct ctgttcagga agtccttatc tagctgcata   3660
tcttcatcat attggtatat cctttttctgt gtttacagag atgtctctta tatctaaatc   3720
tgtccaactg agaagtacct tatcaaagta gcaaatgaga cagcagtctt atgcttccag   3780
aaacacccac aggcatgtcc catgtgagct gctgccatga actgtcaagt gtgtgttgtc   3840
```

```
ttgtgtattt cagttattgt ccctggcttc cttactatgg tgtaatcatg aaggagtgaa    3900
acatcataga aactgtctag cacttccttg ccagtcttta gtgatcagga accatagttg    3960
acagttccaa tcagtagctt aagaaaaaac cgtgtttgtc tcttctggaa tggttagaag    4020
tgagggagtt tgccccgttc tgtttgtaga gtctcatagt tggactttct agcatatatg    4080
tgtccatttc cttatgctgt aaaagcaagt cctgcaacca aactcccatc agcccaatcc    4140
ctgatccctg atcccttcca cctgctctgc tgatgacccc cccagcttca cttctgactc    4200
ttccccagga agggaagggg ggtcagaaga gagggtgagt cctccagaac tcttcctcca    4260
aggacagaag gctcctgccc ccatagtggc ctcgaactcc tggcactacc aaaggacact    4320
tatccacgag agcgcagcat ccgaccaggt tgtcactgag aagatgttta ttttggtcag    4380
ttgggttttt atgtattata cttagtcaaa tgtaatgtgg cttctggaat cattgtccag    4440
agctgcttcc ccgtcacctg ggcgtcatct ggtcctggta agaggagtgc gtggcccacc    4500 aggccccct gtcacccatg acagttcatt cagggccgat ggggcagtcg tggttgggaa     4560
cacagcattt caagcgtcac tttatttcat tcgggcccca cctgcagctc cctcaaagag    4620
gcagttgccc agcctctttc ccttccagtt tattccagag ctgccagtgg ggcctgaggc    4680
tccttagggt tttctctcta tttccccctt tcttcctcat tccctcgtct ttcccaaagg    4740
catcacgagt cagtcgcctt tcagcaggca gccttggcgg tttatcgccc tggcaggcag    4800
gggccctgca gctctcatgc tgccctgcc ttggggtcag gttgacagga ggttggaggg     4860
aaagccttaa gctgcaggat tctcaccagc tgtgtccggc ccagttttgg ggtgtgacct    4920
caatttcaat tttgtctgta cttgaacatt atgaagatgg gggcctcttt cagtgaattt    4980
gtgaacagca gaattgaccg acagctttcc agtacccatg gggctaggtc attaaggcca    5040
catccacagt ctcccccacc cttgttccag ttgttagtta ctacctcctc tcctgacaat    5100
actgtatgtc gtcgagctcc ccccaggtct acccctcccg gccctgcctg ctggtgggct    5160
tgtcatagcc agtgggattg ccggtcttga cagctcagtg agctggagat acttggtcac    5220
agccaggcgc tagcacagct cccttctgtt gatgctgtat tcccatatca aaagacacag    5280
gggacaccca gaaacgccac atcccccaat ccatcagtgc caaactagcc aacggcccca    5340
gcttctcagc tcgctggatg gcggaagctg ctactcgtga gcgccagtgc gggtgcagac    5400
aatcttctgt tgggtggcat cattccaggc ccgaagcatg aacagtgcac ctgggacagg    5460
gagcagcccc aaattgtcac ctgcttctct gcccagcttt tcattgctgt gacagtgatg    5520
gcgaaagagg gtaataacca gacacaaact gccaagttgg gtggagaaag gagtttcttt    5580
agctgacaga atctctgaat tttaaatcac ttagtaagcg gctcaagccc aggagggagc    5640
agagggatac gagcggagtc ccctgcgcgg gaccatctgg aattggttta gcccaagtgg    5700
agcctgacag ccagaactct gtgtccccg tctaaccaca gctccttttc cagagcattc     5760
cagtcaggct ctctgggctg actgggccag gggaggttac aggtaccagt tctttaagaa    5820
gatctttggg catatacatt tttagcctgt gtcattgccc caaatggatt cctgtttcaa    5880
gttcacacct gcagattcta ggacctgtgt cctagacttc agggagtcag ctgtttctag    5940
agttcctacc atggagtggg tctggaggac ctgcccggtg ggggggcaga gccctgctcc    6000
ctccgggtct tcctactctt ctctctgctc tgacgggatt tgttgattct ctccattttg    6060
gtgtctttct cttttagata ttgtatcaat ctttagaaaa ggcatagtct acttgttata    6120
aatcgttagg atactgcctc ccccagggtc taaaattaca tattagaggg gaaaagctga    6180
```

```
acactgaagt cagttctcaa caatttagaa ggaaaaccta gaaaacattt ggcagaaaat    6240
tacatttcga tgttttgaa tgaatacgag caagctttta caacagtgct gatctaaaaa    6300
tacttagcac ttggcctgag atgcctggtg agcattacag gcaagggaa tctggaggta    6360
gccgacctga ggacatggct tctgaacctg tcttttggga gtggtatgga aggtggagcg    6420
ttcaccagtg acctgaagg cccagcacca ccctccttcc cactcttctc atcttgacag    6480
agcctgcccc agcgctgacg tgtcaggaaa acacccaggg aactaggaag gcacttctgc    6540
ctgaggggca gcctgccttg cccactcctg ctctgctcgc ctcggatcag ctgagccttc    6600
tgagctggcc tctcactgcc tccccaaggc cccctgcctg ccctgtcagg aggcagaagg    6660
aagcaggtgt gagggcagtg caaggaggga gcacaaccc cagctcccgc tccgggctcc    6720
gacttgtgca caggcagagc ccagaccctg gaggaaatcc tacctttgaa ttcaagaaca    6780
tttgggaat ttggaaatct ctttgccccc aaacccccat tctgtcctac ctttaatcag    6840
gtcctgctca gcagtgagag cagatgaggt gaaaaggcca agaggtttgg ctcctgccca    6900
ctgatagccc ctctccccgc agtgtttgtg tgtcaagtgg caaagctgtt cttcctggtg    6960
accctgatta tatccagtaa cacatagact gtgcgcatag gcctgctttg tctcctctat    7020
cctgggcttt tgttttgctt tttagttttg cttttagttt ttctgtccct tttatttaac    7080
gcaccgacta gacacacaaa gcagttgaat ttttatatat atatctgtat attgcacaat    7140
tataaactca ttttgcttgt ggctccacac acacaaaaaa agacctgtta aaattatacc    7200
tgttgcttaa ttacaatatt tctgataacc atagcatagg acaagggaaa ataaaaaaag    7260
aaaaaaaga aaaaaaaacg acaaatctgt ctgctggtca cttcttctgt ccaagcagat    7320
tcgtggtctt ttcctcgctt cttcaagg ctttcctgtg ccaggtgaag gaggctccag    7380
gcagcaccca ggttttgcac tcttgtttct cccgtgcttg tgaaagaggt cccaaggttc    7440
tgggtgcagg agcgctccct tgacctgctg aagtccggaa cgtagtcggc acagcctggt    7500
cgccttccac ctctgggagc tggagtccac tggggtggcc tgactccccc agtccccttc    7560
ccgtgacctg tcagggtga gcccatgtgg agtcagcctc gcaggcctcc ctgccagtag    7620
ggtccgagtg tgtttcatcc ttcccactct gtcgagcctg ggggctggag cggagacggg    7680
aggcctggcc tgtctcggaa cctgtgagct gcaccaggta gaacgccagg accccagaa    7740
tcatgtgcgt cagtccaagg ggtcccctcc aggagtagtg aagactccag aaatgtccct    7800
ttcttctccc ccatcctacg agtaattgca tttgcttttg taattcttaa tgagcaatat    7860
ctgctagaga gtttagctgt aacagttctt tttgatcatc ttttttaat aattagaaac    7920
accaaaaaaa tccagaaact tgttcttcca aagcagagag cattataatc accagggcca    7980
aaagcttccc tccctgctgt cattgcttct tctgaggcct gaatccaaaa gaaaaacagc    8040
cataggccct ttcagtggcc gggctacccg tgagcccttc ggaggaccag ggctggggca    8100
gcctctgggc ccacatccgg ggccagctcc ggcgtgtgtt cagtgttagc agtgggtcat    8160
gatgctcttt cccacccagc ctgggatagg ggcagaggag gcgaggaggc cgttgccgct    8220
gatgtttggc cgtgaacagg tgggtgtctg cgtgcgtcca cgtgcgtgtt ttctgactga    8280
catgaaatcg acgcccgagt tagcctcacc cggtgacctc tagccctgcc cggatggagc    8340
ggggcccacc cggttcagtg tttctgggga gctggacagt ggagtgcaaa aggcttgcag    8400
aacttgaagc ctgctccttc ccttgctacc acggcctcct ttccgtttga tttgtcactg    8460
cttcaatcaa taacagccgc tccagagtca gtagtcaatg aatatatgac caaatatcac    8520
caggactgtt actcaatgtg tgccgagccc ttgcccatgc tgggctcccg tgtatctgga    8580
```

```
cactgtaacg tgtgctgtgt ttgctcccct tccccttcct tctttgccct ttacttgtct    8640
ttctggggtt tttctgtttg ggtttggttt ggttttatt tctccttttg tgttccaaac    8700
atgaggttct ctctactggt cctcttaact gtggtgttga ggcttatatt tgtgtaattt    8760
ttggtgggtg aaaggaattt tgctaagtaa atctcttctg tgtttgaact gaagtctgta    8820
ttgtaactat gtttaaagta attgttccag agacaaatat ttctagacac tttttcttta    8880
caaacaaaag cattcggagg gaggggatg gtgactgaga tgagagggga gagctgaaca     8940
gatgacccct gcccagatca gccagaagcc acccaaagca gtggagccca ggagtcccac    9000
tccaagccag caagccgaat agctgatgtg ttgccacttt ccaagtcact gcaaaaccag    9060
gttttgttcc gcccagtgga ttcttgtttt gcttccctc cccccgagat tattaccac     9120 atcccgtgct tttaaggaaa ggcaagattg atgtttcctt gaggggagcc aggaggggat    9180
gtgtgtgtgc agagctgaag agctggggag aatggggctg gcccacccca agcaggaggc    9240
tgggacgctc tgctgtgggc acaggtcagg ctaatgttgg cagatgcagc tcttcctgga    9300
caggccaggt ggtgggcatt ctctctccaa ggtgtgcccc gtgggcatta ctgtttaaga    9360
cacttccgtc acatcccacc ccatcctcca gggctcaaca ctgtgacatc tctattcccc    9420
accctcccct tcccagggca ataaaatgac catggagggg gcttgcactc tcttggctgt    9480 caccccgatcg ccagcaaaac ttagatgtga gaaaacccct tcccattcca tggcgaaaac   9540
atctccttag aaaagccatt accctcatta ggcatggttt tgggctccca aaacacctga    9600
cagcccctcc ctcctctgag aggcggagag tgctgactgt agtgaccatt gcatgccggg    9660
tgcagcatct ggaagagcta ggcagggtgt ctgcccctc ctgagttgaa gtcatgctcc     9720
cctgtgccag cccagaggcc gagagctatg acagcattg ccagtaacac aggccaccct     9780
gtgcagaagg gagctggctc cagcctggaa acctgtctga ggttgggaga ggtgcacttg    9840
gggcacaggg agaggccggg acacacttag ctggagatgc tctaaaagc cctgtatcgt     9900 attccacttc agttttttgtg ttttgggaca attactttag aaaataagta ggtcgtttta    9960
aaaacaaaaa ttattgattg cttttttgta gtgttcagaa aaaaggttct ttgtgtatag    10020
ccaaatgact gaaagcactg atatatttaa aaacaaaagg caatttatta aggaaatttg    10080
taccatttca gtaaacctgt ctgaatgtac ctgtatacgt ttcaaaaaca cccccccccc    10140
actgaatccc tgtaacctat ttattatata aagagtttgc cttataaatt t             10191
```

<210> SEQ ID NO 26
<211> LENGTH: 10179
<212> TYPE: DNA
<213> ORGANISM: Homo sapiens

<400> SEQUENCE: 26

```
ccggaaaatg gccgccgccg ccgccgcgcc gagcggagga ggaggaggag gcgaggagga      60
gagactgctc cataaaaata cagactcacc agttcctgct ttgatgtgac atgtgactcc    120
ccagaataca ccttgcttct gtagaccagc tccaacagga ttccatggta gctgggatgt    180
tagggctcag ggaagaaaag tcagaagacc aggacctcca gggcctcaag acaaaccccc    240
tcaagtttaa aaaggtgaag aaagataaga agaagagaa agagggcaag catgagcccg    300
tgcagccatc agcccaccac tctgctgagc ccgcagaggc aggcaaagca gagacatcag    360
aagggtcagg ctccgccccg gctgtgccgg aagcttctgc ctcccccaaa cagcggcgct    420
ccatcatccg tgaccgggga cccatgtatg atgaccccac cctgcctgaa ggctggacac    480
```

```
ggaagcttaa gcaaaggaaa tctggccgct ctgctgggaa gtatgatgtg tatttgatca    540
atccccaggg aaaagccttt cgctctaaag tggagttgat tgcgtacttc gaaaaggtag    600
gcgacacatc cctggaccct aatgattttg acttcacggt aactgggaga gggagcccct    660
cccggcgaga gcagaaacca cctaagaagc ccaaatctcc caaagctcca ggaactggca    720
gaggccgggg acgccccaaa gggagcggca ccacgagacc caaggcggcc acgtcagagg    780
gtgtgcaggt gaaaagggtc ctggagaaaa gtcctgggaa gctccttgtc aagatgcctt    840
ttcaaacttc gccagggggc aaggctgagg ggggtggggc caccacatcc acccaggtca    900
tggtgatcaa acgcccggc aggaagcgaa agctgaggc cgaccctcag gccattccca    960
agaaacgggg ccgaaagccg ggagtgtgg tggcagccgc tgccgccgag gccaaaaaga   1020
aagccgtgaa ggagtcttct atccgatctg tgcaggagac cgtactcccc atcaagaagc   1080
gcaagacccg ggagacggtc agcatcgagg tcaaggaagt ggtgaagccc ctgctggtgt   1140
ccaccctcgg tgaagagagc gggaaaggac tgaagacctg taagagccct gggcggaaaa   1200
gcaaggagag cagccccaag gggcgcagca gcagcgcctc ctcaccccccc aagaaggagc   1260 accaccacca tcaccaccac tcagagtccc caaaggcccc cgtgccactg ctcccacccc   1320
tgcccccacc tccacctgag cccgagagct ccgaggaccc caccagcccc cctgagcccc   1380
aggacttgag cagcagcgtc tgcaaagagg agaagatgcc cagaggaggc tcactgagaa   1440
gcgacggctg ccccaaggag ccagctaaga ctcagcccgc ggttgccacc gccgccacgg   1500
ccgcagaaaa gtacaaacac cgaggggagg gagagcgcaa agacattgtt tcatcctcca   1560
tgccaaggcc aaacagagag gagcctgtgg acagccggac gcccgtgacc gagagagtta   1620
gctgacttta cacggagcgg attgcaaagc aaaccaacaa gaataaaggc agctgttgtc   1680
tcttctcctt atgggtaggg ctctgacaaa gcttcccgat taactgaaat aaaaaatatt   1740
ttttttcttt tcagtaaact tagagtttcg tggcttcagg gtgggagtag ttggagcatt   1800
ggggatgttt ttcttaccga caagcacagt caggttgaag acctaaccag ggccagaagt   1860
agctttgcac ttttctaaac taggctcctt caacaaggct tgctgcagat actactgacc   1920
agacaagctg ttgaccaggc acctcccctc ccgcccaaac ctttccccca tgtggtcgtt   1980
agagacagag cgacagagca gttgagagga cactcccgtt ttcggtgcca tcagtgcccc   2040
gtctacagct cccccagctc cccccacctc ccccactccc aaccacgttg ggacagggag   2100
gtgtgaggca ggagagacag ttggattctt tagagaagat ggatatgacc agtggctatg   2160
gcctgtgcga tcccacccgt ggtggctcaa gtctggcccc acaccagccc caatccaaaa   2220
ctggcaagga cgcttcacag gacaggaaag tggcacctgt ctgctccagc tctggcatgg   2280
ctaggagggg ggagtccctt gaactactgg gtgtagactg gcctgaacca caggagagga   2340
tggcccaggg tgaggtggca tggtccattc tcaagggacg tcctccaacg ggtggcgcta   2400
gaggccatga aggcagtagg acaaggtgca ggcaggctgg cctggggtca ggccgggcag   2460
agcacagcgg ggtgagaggg attcctaatc actcagagca gtctgtgact tagtggacag   2520 gggaggggc aaaggggag gagaagaaaa tgttcttcca gttactttcc aattctcctt   2580
tagggacagc ttagaattat ttgcactatt gagtcttcat gttcccactt caaaacaaac   2640
agatgctctg agagcaaact ggcttgaatt ggtgacattt agtccctcaa gccaccagat   2700
gtgacagtgt tgagaactac ctggatttgt atatatacct gcgcttgttt taaagtgggc   2760
tcagcacata gggttcccac gaagctccga aactctaagt gtttgctgca atttttataag   2820 gacttcctga ttggtttctc ttctcccctt ccatttctgc cttttgttca tttcatcctt   2880
```

-continued

```
tcacttctttt cccttcctcc gtcctcctcc ttcctagttc atcccttctc ttccaggcag    2940
ccgcggtgcc caaccacact tgtcggctcc agtccccaga actctgcctg ccctttgtcc    3000
tcctgctgcc agtaccagcc ccaccctgtt ttgagccctg aggaggcctt gggctctgct    3060
gagtccgacc tggcctgtct gtgaagagca agagagcagc aaggtcttgc tctcctaggt    3120
agcccctct  tccctggtaa gaaaaagcaa aaggcatttc ccaccctgaa caacgagcct    3180
tttcacccttt ctactctaga gaagtggact ggaggagctg ggcccgattt ggtagttgag    3240
gaaagcacag aggcctcctg tggcctgcca gtcatcgagt ggcccaacag gggctccatg    3300
ccagccgacc ttgacctcac tcagaagtcc agagtctagc gtagtgcagc agggcagtag    3360
cggtaccaat gcagaactcc caagacccga gctgggacca gtacctgggt ccccagccct    3420
tcctctgctc ccccttttcc ctcggagttc ttcttgaatg gcaatgtttt gcttttgctc    3480
gatgcagaca gggggccaga acaccacaca tttcactgtc tgtctggtcc atagctgtgg    3540
tgtaggggct tagaggcatg ggcttgctgt gggttttaa  ttgatcagtt ttcatgtggg    3600
atcccatctt tttaacctct gttcaggaag tccttatcta gctgcatatc ttcatcatat    3660
tggtatatcc ttttctgtgt ttacagagat gtctcttata tctaaatctg tccaactgag    3720
aagtaccttaa tcaaagtagc aaatgagaca gcagtcttat gcttccagaa acacccacag    3780
gcatgtccca tgtgagctgc tgccatgaac tgtcaagtgt gtgttgtctt gtgtatttca    3840
gttattgtcc ctggcttcct tactatggtt aatcatgaa  ggagtgaaac atcatagaaa    3900
ctgtctagca cttccttgcc agtctttagt gatcaggaac catagttgac agttccaatc    3960
agtagcttaa gaaaaaaccg tgtttgtctc ttctggaatg gttagaagtg agggagtttg    4020
cccccgttctg tttgtagagt ctcatagttg gactttctag catatatgtg tccatttcct    4080
tatgctgtaa aagcaagtcc tgcaaccaaa ctcccatcag cccaatccct gatccctgat    4140
cccttccacc tgctctgctg atgacccccc cagcttcact tctgactctt ccccaggaag    4200
ggaaggggg  tcagaagaga gggtgagtcc tccagaactc ttcctccaag gacagaaggc    4260
tcctgcccccc atagtggcct cgaactcctg gcactaccaa aggacactta tccacgagag    4320
cgcagcatcc gaccaggttg tcactgagaa gatgtttatt ttggtcagtt gggtttttat    4380
gtattatact tagtcaaatg taatgtggct tctggaatca ttgtccagag ctgcttcccc    4440
gtcacctggg cgtcatctgg tcctggtaag aggagtgcgt ggcccaccag gcccccctgt    4500
cacccatgac agttcattca gggccgatgg ggcagtcgtg gttgggaaca cagcatttca    4560
agcgtcactt tatttcattc gggccccacc tgcagctccc tcaaagaggc agttgcccag    4620
cctctttccc ttccagtttta ttccagagct gccagtgggg cctgaggctc cttagggttt    4680
tctctctatt tcccccttttc ttcctcattc cctcgtcttt cccaaaggca tcacgagtca    4740
gtcgcctttc agcaggcagc cttggcggtt tatcgccctg gcaggcaggg gccctgcagc    4800
tctcatgctg cccctgcctt ggggtcaggt tgacaggagg ttggagggaa agccttaagc    4860
tgcaggattc tcaccagctg tgtccggccc agttttgggg tgtgacctca atttcaattt    4920
tgtctgtact tgaacattat gaagatgggg gcctcttttca gtgaatttgt gaacagcaga    4980
attgaccgac agctttccag tacccatggg gctaggtcat taaggccaca tccacagtct    5040
ccccaccct  tgttccagtt gttagttact acctcctctc ctgacaatac tgtatgtcgt    5100
cgagctcccc ccaggtctac ccctcccggc cctgcctgct ggtgggcttg tcatagccag    5160
tgggattgcc ggtcttgaca gctcagtgag ctggagatac ttggtcacag ccaggcgcta    5220
```

```
gcacagctcc cttctgttga tgctgtattc ccatatcaaa agacacaggg gacacccaga    5280
aacgccacat cccccaatcc atcagtgcca aactagccaa cggccccagc ttctcagctc    5340
gctggatggc ggaagctgct actcgtgagc gccagtgcgg gtgcagacaa tcttctgttg    5400
ggtggcatca ttccaggccc gaagcatgaa cagtgcacct gggacaggga gcagcccaa     5460 attgtcacct gcttctctgc ccagcttttc attgctgtga cagtgatggc gaaagagggt    5520
aataaccaga cacaaactgc caagttgggt ggagaaagga gtttctttag ctgacagaat    5580
ctctgaattt taaatcactt agtaagcggc tcaagcccag gagggagcag agggatacga    5640
gcggagtccc ctgcgcggga ccatctggaa ttggtttagc ccaagtggag cctgacagcc    5700
agaactctgt gtccccgtc taaccacagc tccttttcca gagcattcca gtcaggctct     5760
ctgggctgac tgggccaggg gaggttacag gtaccagttc tttaagaaga tctttgggca    5820
tatacatttt tagcctgtgt cattgcccca aatggattcc tgtttcaagt tcacacctgc    5880
agattctagg acctgtgtcc tagacttcag ggagtcagct gtttctagag ttcctaccat    5940
ggagtgggtc tggaggacct gcccggtggg ggggcagagc cctgctccct ccgggtcttc    6000
ctactcttct ctctgctctg acgggatttg ttgattctct ccattttggt gtctttctct    6060
tttagatatt gtatcaatct ttagaaaagg catagtctac ttgttataaa tcgttaggat    6120
actgcctccc ccagggtcta aaattacata ttagagggga aaagctgaac actgaagtca    6180
gttctcaaca atttagaagg aaaacctaga aaacatttgg cagaaaatta catttcgatg    6240
tttttgaatg aatacgagca agcttttaca acagtgctga tctaaaaata cttagcactt    6300
ggcctgagat gcctggtgag cattacaggc aaggggaatc tggaggtagc cgacctgagg    6360
acatggcttc tgaacctgtc ttttgggagt ggtatggaag gtggagcgtt caccagtgac    6420
ctggaaggcc cagcaccacc ctccttccca ctcttctcat cttgacagag cctgccccag    6480
cgctgacgtg tcaggaaaac acccagggaa ctaggaaggc acttctgcct gaggggcagc    6540
ctgccttgcc cactcctgct ctgctcgcct cggatcagct gagccttctg agctggcctc    6600
tcactgcctc cccaaggccc cctgcctgcc ctgtcaggag gcagaaggaa gcaggtgtga    6660
gggcagtgca aggagggagc acaaccccca gctcccgctc cgggctccga cttgtgcaca    6720
ggcagagccc agaccctgga ggaaatccta cctttgaatt caagaacatt tgggaatt      6780 ggaaatctct ttgcccccaa accccattc tgtcctacct taatcaggt cctgctcagc      6840 agtgagagca gatgaggtga aaaggccaag aggtttggct cctgcccact gatagcccct    6900
ctccccgcag tgtttgtgtg tcaagtggca aagctgttct tcctggtgac cctgattata    6960
tccagtaaca catagactgt gcgcataggc ctgctttgtc tcctctatcc tgggcttttg    7020
ttttgctttt tagttttgct tttagttttt ctgtcccttt tatttaacgc accgactaga    7080
cacacaaagc agttgaattt ttatatatat atctgtatat tgcacaatta taaactcatt    7140
ttgcttgtgg ctccacacac acaaaaaaag acctgttaaa attatacctg ttgcttaatt    7200
acaatatttc tgataaccat agcataggac aagggaaaat aaaaaagaa aaaaagaaa      7260 aaaaacgac aaatctgtct gctggtcact tcttctgtcc aagcagattc gtggtctttt     7320
cctcgcttct ttcaagggct ttcctgtgcc aggtgaagga ggctccaggc agcacccagg    7380
ttttgcactc ttgtttctcc cgtgcttgtg aaagaggtcc caaggttctg ggtgcaggag    7440
cgctcccttg acctgctgaa gtccggaacg tagtcggcac agcctggtcg ccttccacct    7500
ctgggagctg gagtccactg gggtggcctg actcccccag tccccttccc gtgacctggt    7560
cagggtgagc ccatgtggag tcagcctcgc aggcctccct gccagtaggg tccgagtgtg    7620
```

-continued

```
tttcatcctt cccactctgt cgagcctggg ggctggagcg gagacgggag gcctggcctg    7680
tctcggaacc tgtgagctgc accaggtaga acgccaggga ccccagaatc atgtgcgtca    7740
gtccaagggg tcccctccag gagtagtgaa gactccagaa atgtcccttt cttctccccc    7800
atcctacgag taattgcatt tgcttttgta attcttaatg agcaatatct gctagagagt    7860
ttagctgtaa cagttctttt tgatcatctt tttttaataa ttagaaacac caaaaaaatc    7920
cagaaacttg ttcttccaaa gcagagagca ttataatcac cagggccaaa agcttccctc    7980
cctgctgtca ttgcttcttc tgaggcctga atccaaaaga aaaacagcca taggcccttt    8040
cagtggccgg gctacccgtg agcccttcgg aggaccaggg ctggggcagc tctgggccc    8100 acatccgggg ccagctccgg cgtgtgttca gtgttagcag tgggtcatga tgctctttcc    8160
cacccagcct gggatagggg cagaggaggc gaggaggccg ttgccgctga tgtttggccg    8220
tgaacaggtg ggtgtctgcg tgcgtccacg tgccgtgtttt ctgactgaca tgaaatcgac    8280
gcccgagtta gcctcacccg gtgacctcta gccctgcccg gatggagcgg ggcccacccg    8340
gttcagtgtt tctggggagc tggacagtgg agtgcaaaag gcttgcagaa cttgaagcct    8400
gctccttccc ttgctaccac ggcctccttt ccgtttgatt tgtcactgct tcaatcaata    8460
acagccgctc cagagtcagt agtcaatgaa tatatgacca aatatcacca ggactgttac    8520
tcaatgtgtg ccgagcccct tgcccatgctg ggctcccgtg tatctggaca ctgtaacgtg    8580
tgctgtgttt gctcccctttc cccttccttc tttgcccttt acttgtcttt ctggggtttt    8640
tctgtttggg tttggtttgg ttttatttc tccttttgtg ttccaaacat gaggttctct    8700
ctactggtcc tcttaactgt ggtgttgagg cttatatttg tgtaattttt ggtgggtgaa    8760
aggaattttg ctaagtaaat ctcttctgtg tttgaactga agtctgtatt gtaactatgt    8820
ttaaagtaat tgttccagag acaaatattt ctagacactt tttctttaca aacaaaagca    8880
ttcggaggga gggggatggt gactgagatg agaggggaga gctgaacaga tgaccccctgc    8940 ccagatcagc cagaagccac ccaaagcagt ggagcccagg agtcccactc caagccagca    9000
agccgaatag ctgatgtgtt gccactttcc aagtcactgc aaaaccaggt tttgttccgc    9060
ccagtggatt cttgttttgc ttcccctccc cccgagatta ttaccaccat cccgtgctttt    9120 taaggaaagg caagattgat gtttccttga ggggagccag gaggggatgt gtgtgtgcag    9180
agctgaagag ctggggagaa tggggctggg cccacccaag caggaggctg ggacgctctg    9240
ctgtgggcac aggtcaggct aatgttggca gatgcagctc ttcctggaca ggccaggtgg    9300
tgggcattct ctctccaagg tgtgccccgt gggcattact gtttaagaca cttccgtcac    9360
atcccacccc atcctccagg gctcaacact gtgacatctc tattcccac cctccccttc    9420 ccagggcaat aaaatgacca tggaggggc ttgcactctc ttggctgtca cccgatcgcc    9480
agcaaaactt agatgtgaga aaccccttc ccattccatg gcgaaaacat ctccttagaa    9540
aagccattac cctcattagg catggttttg ggctcccaaa acacctgaca gcccctccct    9600
cctctgagag gcggagagtg ctgactgtag tgaccattgc atgccgggtg cagcatctgg    9660
aagagctagg cagggtgtct gccccctcct gagttgaagt catgctcccc tgtgccagcc    9720
cagaggccga gagctatgga cagcattgcc agtaacacag gccaccctgt gcagaaggga    9780
gctggctcca gcctggaaac ctgtctgagg ttggagagg tgcactggg gcacagggag    9840 aggccgggac acacttagct ggagatgtct ctaaaagccc tgtatcgtat tcaccttcag    9900
tttttgtgtt ttgggacaat tactttagaa aataagtagg tcgttttaaa aacaaaaatt    9960
```

```
attgattgct tttttgtagt gttcagaaaa aaggttcttt gtgtatagcc aaatgactga      10020
aagcactgat atatttaaaa acaaaaggca atttattaag gaaatttgta ccatttcagt      10080
aaacctgtct gaatgtacct gtatacgttt caaaaacacc cccccccac tgaatccctg       10140 taacctattt attatataaa gagtttgcct tataaattt                              10179
```

```
<210> SEQ ID NO 27
<211> LENGTH: 10185
<212> TYPE: DNA
<213> ORGANISM: Homo sapiens

<400> SEQUENCE: 27
```

```
ccggaaaatg gccgccgccg ccgccgccgc gccgagcgga ggaggaggag gaggaggcga        60
ggaggagaga ctgctccata aaatacaga ctcaccagtt cctgctttga tgtgacatgt       120
gactccccag aatacacctt gcttctgtag accagctcca acaggattcc atggtagctg      180
ggatgttagg gctcagggaa gaaaagtcag aagaccagga cctccagggc ctcaaggaca      240 aaccccctcaa gtttaaaaag gtgaagaaag ataagaaaga agagaaagag ggcaagcatg     300
agcccgtgca gccatcagcc caccactctg ctgagcccgc agaggcaggc aaagcagaga      360
catcagaagg gtcaggctcc gccccggctg tgccggaagc ttctgcctcc cccaaacagc      420
ggcgctccat catccgtgac cggggaccca tgtatgatga ccccaccctg cctgaaggct      480
ggacacggaa gcttaagcaa aggaaatctg gccgctctgc tgggaagtat gatgtgtatt      540
tgatcaatcc ccagggaaaa gcctttcgct ctaaagtgga gttgattgcg tacttcgaaa      600
aggtaggcga cacatccctg gaccctaatg attttgactt cacggtaact gggagaggga     660 gccctcccg gcgagagcag aaaccaccta agaagcccaa atctcccaaa gctccaggaa       720
ctggcagagg ccggggacgc cccaaaggga gcggcaccac gagacccaag gcggccacgt      780
cagagggtgt gcaggtgaaa agggtcctgg agaaaagtcc tgggaagctc cttgtcaaga      840
tgccttttca aacttcgcca gggggcaagg ctgaggggg tggggccacc acatccaccc       900
aggtcatggt gatcaaacgc cccggcagga agcgaaaagc tgaggccgac cctcaggcca      960
ttcccaagaa acgggggcga aagccgggga gtgtggtggc agccgctgcc gccgaggcca     1020
aaaagaaagc cgtgaaggag tcttctatcc gatctgtgca ggagaccgta ctccccatca     1080
agaagcgcaa gaccgggag acggtcagca tcgaggtcaa ggaagtggtg aagcccctgc      1140
tggtgtccac cctcggtgag aagagcggga aaggactgaa gacctgtaag agccctgggc     1200
ggaaaagcaa ggagagcagc cccaaggggc gcagcagcag cgcctcctca cccccaaga      1260 aggagcacca ccaccatcac caccactcag agtcccaaa ggccccgtg ccactgctcc        1320 cacccctgcc cccacctcca cctgagcccg agagctccga ggaccccacc agccccctg      1380 agccccagga cttgagcagc agcgtctgca agaggagaa gatgccaga ggaggctcac       1440 tggagagcga cggctgccc aaggagccag ctaagactca gcccgcggtt gccaccgccg      1500
ccacggccgc agaaaagtac aaacaccgag gggaggaga gcgcaaagac attgtttcat     1560
cctccatgcc aaggccaaac agagaggagc ctgtggacag ccgacgccc gtgaccgaga      1620 gagttagctg actttacacg gagcggattg caaagcaaac caacaagaat aaaggcagct     1680
gttgtctctt ctcctatgg gtagggtctc tgacaaagctt cccgattaac tgaaataaaa     1740 aatattttt tttcttttcag taaacttaga gtttcgtggc ttcagggtgg gagtagttgg     1800
agcattgggg atgttttct taccgacaag cacagtcagg ttgaagacct aaccagggcc      1860
agaagtagct ttgcactttt ctaaactagg ctccttcaac aaggcttgct gcagatacta     1920
```

```
ctgaccagac aagctgttga ccaggcacct ccctcccgc ccaaacctt  ccccatgtg   1980
gtcgttagag acagagcgac agagcagttg agaggacact cccgttttcg gtgccatcag   2040
tgccccgtct acagctcccc cagctcccc  cacctcccc  actcccaacc acgttgggac   2100
agggaggtgt gaggcaggag agacagttgg attctttaga gaagatggat atgaccagtg   2160
gctatggcct gtgcgatccc acccgtggtg gctcaagtct ggccccacac cagccccaat   2220
ccaaaactgg caaggacgct tcacaggaca ggaaagtggc acctgtctgc tccagctctg   2280
gcatggctag gagggggag tcccttgaac tactgggtgt agactggcct gaaccacagg   2340
agaggatggc ccagggtgag gtggcatggt ccattctcaa gggacgtcct ccaacgggtg   2400
gcgctagagg ccatggaggc agtaggacaa ggtgcaggca ggctggcctg ggtcaggcc   2460
gggcagagca cagcggggtg agagggattc ctaatcactc agagcagtct gtgacttagt   2520
ggacagggga gggggcaaag ggggaggaga agaaaatgtt cttccagtta ctttccaatt   2580
ctcctttagg gacagcttag aattatttgc actattgagt cttcatgttc ccacttcaaa   2640
acaaacagat gctctgagag caaactggct tgaattggtg acatttagtc cctcaagcca   2700
ccagatgtga cagtgttgag aactacctgg atttgtatat atacctgcgc ttgttttaaa   2760
gtgggctcag cacataggt tcccacgaag ctccgaaact ctaagtgttt gctgcaattt   2820
tataaggact tcctgattgg tttctcttct cccttccat ttctgcctt  tgttcattc    2880
atcctttcac ttctttccct tcctccgtcc tcctccttcc tagttcatcc cttctcttcc   2940
aggcagccgc ggtgcccaac cacacttgtc ggctccagtc cccagaactc tgcctgccct   3000
ttgtcctcct gctgccagta ccagcccac cctgttttga gccctgagga ggccttgggc   3060
tctgctgagt ccgacctggc ctgtctgtga agagcaagag agcagcaagg tcttgctctc   3120
ctaggtagcc ccctcttccc tggtaagaaa agcaaaagg catttcccac cctgaacaac   3180
gagcctttc acccttctac tctagagaag tggactggag gagctgggcc cgatttggta   3240
gttgaggaaa gcacagaggc ctcctgtggc ctgccagtca tcgagtggcc caacaggggc   3300
tccatgccag ccgaccttga cctcactcag aagtccagag tctagcgtag tgcagcaggg   3360
cagtagcggt accaatgcag aactcccaag acccgagctg ggaccagtac ctgggtcccc   3420
agcccttcct ctgctccccc ttttccctcg gagttcttct tgaatggcaa tgttttgctt   3480
ttgctcgatg cagacagggg gccagaacac cacacatttc actgtctgtc tggtccatag   3540
ctgtggtgta gggcttaga  ggcatgggct tgctgtgggt ttttaattga tcagttttca   3600
tgtgggatcc catcttttta acctctgttc aggaagtcct tatctagctg catatcttca   3660
tcatattggt atatccttt  ctgtgtttac agagatgtct cttatatcta aatctgtcca   3720
actgagaagt accttatcaa agtagcaaat gagacagcag tcttatgctt ccagaaacac   3780
ccacaggcat gtcccatgtg agctgctgcc atgaactgtc aagtgtgtgt tgtcttgtgt   3840
atttcagtta ttgtccctgg cttccttact atggtgtaat catgaaggag tgaaacatca   3900
tagaaactgt ctagcacttc cttgccagtc tttagtgatc aggaaccata gttgacagtt   3960
ccaatcagta gcttaagaaa aaaccgtgtt tgtctcttct ggaatggtta aagtgaggg   4020
agtttgcccc gttctgtttg tagagtctca tagttggact ttctagcata tatgtgtcca   4080
tttccttatg ctgtaaaagc aagtcctgca accaaactcc catcagccca atccctgatc   4140
cctgatccct tccacctgct ctgctgatga cccccccagc ttcacttctg actcttcccc   4200
aggaagggaa gggggtcag  aagagagggt gagtcctcca gaactcttcc tccaaggaca   4260
```

```
gaaggctcct gccccatag tggcctcgaa ctcctggcac taccaaagga cacttatcca   4320
cgagagcgca gcatccgacc aggttgtcac tgagaagatg tttattttgg tcagttgggt   4380
ttttatgtat tatacttagt caaatgtaat gtggcttctg aatcattgt ccagagctgc   4440
ttccccgtca cctgggcgtc atctggtcct ggtaagagga gtgcgtggcc caccaggccc   4500
ccctgtcacc catgacagtt cattcagggc cgatggggca gtcgtggttg gaacacagc   4560
atttcaagcg tcactttatt tcattcgggc cccacctgca gctccctcaa agaggcagtt   4620
gcccagcctc tttcccttcc agtttattcc agagctgcca gtggggcctg aggctcctta   4680
gggttttctc tctatttccc ccttttcttcc tcattccctc gtctttccca aaggcatcac   4740
gagtcagtcg cctttcagca ggcagccttg gcggtttatc gccctggcag gcaggggccc   4800
tgcagctctc atgctgcccc tgccttgggg tcaggttgac aggaggttgg agggaaagcc   4860
ttaagctgca ggattctcac cagctgtgtc cggcccagtt ttggggtgtg acctcaattt   4920
caattttgtc tgtacttgaa cattatgaag atggggcct ctttcagtga atttgtgaac   4980
agcagaattg accgacagct ttccagtacc catgggcta ggtcattaag gccacatcca   5040
cagtctcccc caccccttgtt ccagttgtta gttactacct cctctcctga caatactgta   5100
tgtcgtcgag ctcccccag gtctacccct cccggccctg cctgctggtg ggcttgtcat   5160
agccagtggg attgccggtc ttgacagctc agtgagctgg agatacttgg tcacagccag   5220
gcgctagcac agctcccttc tgttgatgct gtattcccat atcaaaagac acagggagaca   5280
cccagaaacg ccacatcccc caatccatca gtgccaaact agccaacggc cccagcttct   5340
cagctcgctg gatggcggaa gctgctactc gtgagcgcca gtgcgggtgc agacaatctt   5400
ctgttgggtg gcatcattcc aggcccgaag catgaacagt gcacctggga cagggagcag   5460
ccccaaattg tcacctgctt ctctgcccag cttttcattg ctgtgacagt gatggcgaaa   5520
gagggtaata accagacaca aactgccaag ttgggtggag aaaggagttt ctttagctga   5580
cagaatctct gaattttaaa tcacttagta agcggctcaa gcccaggagg gagcagaggg   5640
atacgagcgg agtcccctgc gcgggaccat ctggaattgg tttagcccaa gtggagcctg   5700
acagccagaa ctctgtgtcc cccgtctaac cacagctcct tttccagagc attccagtca   5760
ggctctctgg gctgactggg ccaggggagg ttacaggtac cagttctttta agaagatctt   5820
tgggcatata cattttttagc ctgtgtcatt gccccaaatg gattcctgtt tcaagttcac   5880
acctgcagat tctaggacct gtgtcctaga cttcagggag tcagctgttt ctagagttcc   5940
taccatggag tgggtctgga ggacctgccc ggtggggggg cagagccctg ctccctccgg   6000
gtcttcctac tcttctctct gctctgacgg gatttgttga ttctctccat tttggtgtct   6060
ttctcttttta gatattgtat caatctttag aaaaggcata gtctacttgt tataaatcgt   6120
taggatactg cctcccccag ggtctaaaat tacatattag agggaaaag ctgaacactg   6180
aagtcagttc tcaacaattt agaaggaaaa cctagaaaac atttggcaga aaattacatt   6240
tcgatgtttt tgaatgaata cgagcaagct tttacaacag tgctgatcta aaaatactta   6300
gcacttggcc tgagatgcct ggtgagcatt acaggcaagg gaatctgga ggtagccgac   6360
ctgaggacat ggcttctgaa cctgtctttt gggagtggta tggaaggtgg agcgttcacc   6420
agtgacctga aaggcccagc accacccctcc ttcccactct tctcatcttg acagagcctg   6480
ccccagcgct gacgtgtcag gaaaacaccc agggaactag gaaggcactt ctgcctgagg   6540
ggcagcctgc cttgcccact cctgctctgc tcgcctcgga tcagctgagc cttctgagct   6600
ggcctctcac tgcctcccca aggcccctg cctgccctgt caggaggcag aaggaagcag   6660
```

```
gtgtgagggc agtgcaagga gggagcacaa ccccagctc ccgctccggg ctccgacttg    6720
tgcacaggca gagcccagac cctggaggaa atcctacctt tgaattcaag aacatttggg    6780
gaatttggaa atctctttgc ccccaaaccc ccattctgtc ctacctttaa tcaggtcctg    6840
ctcagcagtg agagcagatg aggtgaaaag gccaagaggt ttggctcctg cccactgata    6900
gcccctctcc ccgcagtgtt tgtgtgtcaa gtggcaaagc tgttcttcct ggtgaccctg    6960
attatatcca gtaacacata gactgtgcgc ataggcctgc tttgtctcct ctatcctggg    7020
cttttgtttt gcttttagt tttgctttta gttttctgt cccttttatt taacgcaccg     7080
actagacaca caaagcagtt gaatttttat atatatatct gtatattgca caattataaa    7140
ctcattttgc ttgtggctcc acacacacaa aaaagacct gttaaaatta tacctgttgc     7200
ttaattacaa tatttctgat aaccatagca taggacaagg gaaataaaaa aagaaaaaa    7260 aagaaaaaaa aacgacaaat ctgtctgctg gtcacttctt ctgtccaagc agattcgtgg    7320
tcttttcctc gcttctttca agggctttcc tgtgccaggt gaaggaggct ccaggcagca    7380
cccaggtttt gcactcttgt ttctcccgtc cttgtgaaag aggtcccaag gttctgggtg    7440
caggagcgct cccttgacct gctgaagtcc ggaacgtagt cggcacagcc tggtcgcctt    7500
ccacctctgg gagctggagt ccactggggt ggcctgactc ccccagtccc cttcccgtga    7560
cctggtcagg gtgagcccat gtggagtcag cctcgcaggc ctccctgcca gtagggtccg    7620
agtgtgtttc atccttccca ctctgtcgag cctgggggct ggagcggaga cgggaggcct    7680
ggcctgtctc ggaacctgtg agctgcacca ggtagaacgc cagggacccc agaatcatgt    7740
gcgtcagtcc aaggggtccc ctccaggagt agtgaagact ccagaaatgt ccctttcttc    7800
tcccccatcc tacgagtaat tgcatttgct tttgtaattc ttaatgagca atatctgcta    7860
gagagtttag ctgtaacagt tcttttgat catctttttt taataattag aaacaccaaa    7920
aaaatccaga aacttgttct tccaaagcag agagcattat aatcaccagg ccaaaagct    7980 tccctccctg ctgtcattgc ttcttctgag gcctgaatcc aaaagaaaaa cagccatagg    8040 cccttttcagt ggccgggcta cccgtgagcc cttcggagga ccaggctgg ggcagcctct    8100 gggcccacat ccggggccag ctccggcgtg tgttcagtgt tagcagtggg tcatgatgct    8160 cttttcccacc cagcctggga taggggcaga ggaggcgagg aggccgttgc cgctgatgtt    8220
tggccgtgaa caggtgggtg tctgcgtgcg tccacgtgcg tgttttctga ctgacatgaa    8280
atcgacgccc gagttagcct caccggtga cctctagccc tgcccggatg gagcggggcc     8340
cacccggttc agtgtttctg gggagctgga cagtggagtg caaaaggctt gcagaacttg    8400
aagcctgctc cttcccttgc taccacggcc tcctttccgt ttgatttgtc actgcttcaa    8460
tcaataacag ccgctccaga gtcagtagtc aatgaatata tgaccaaata tcaccaggac    8520
tgttactcaa tgtgtgccga gcccttgccc atgctgggct cccgtgtatc tggacactgt    8580
aacgtgtgct gtgtttgctc ccttccct tccttctttg ccctttactt gtctttctgg      8640 ggttttctg tttgggtttg gtttggtttt tattctcct tttgtgttcc aaacatgagg     8700
ttctctctac tggtcctctt aactgtggtg ttgaggctta tatttgtgta atttttggtg    8760
ggtgaaagga atttgctaa gtaaatctct tctgtgtttg aactgaagtc tgtattgtaa    8820
ctatgtttaa agtaattgtt ccagagacaa atatttctag acactttttc tttacaaaca    8880
aaagcattcg gagggagggg gatggtgact gagatgagag gggagagctg aacagatgac    8940
ccctgcccag atcagccaga agccaccaa agcagtggag cccaggagtc ccactccaag    9000
```

```
ccagcaagcc gaatagctga tgtgttgcca cttttccaagt cactgcaaaa ccaggttttg    9060
ttccgcccag tggattcttg ttttgcttcc cctcccccg agattattac caccatcccg    9120
tgcttttaag gaaaggcaag attgatgttt ccttgagggg agccaggagg ggatgtgtgt    9180
gtgcagagct gaagagctgg ggagaatggg gctgggccca cccaagcagg aggctgggac    9240
gctctgctgt gggcacaggt caggctaatt ttggcagatg cagctcttcc tggacaggcc    9300
aggtggtggg cattctctct ccaaggtgtg ccccgtgggc attactgttt aagacacttc    9360
cgtcacatcc caccccatcc tccagggctc aacactgtga catctctatt ccccacccctc   9420 cccttcccag ggcaataaaa tgaccatgga gggggcttgc actctcttgg ctgtcacccg    9480
atcgccagca aaacttagat gtgagaaaac cccttcccat tccatggcga aaacatctcc    9540
ttagaaaagc cattaccctc attaggcatg gttttgggct cccaaaacac ctgacagccc    9600
ctccctcctc tgagaggcgg agagtgctga ctgtagtgac cattgcatgc cgggtgcagc    9660
atctggaaga gctaggcagg gtgtctgccc cctcctgagt tgaagtcatg ctcccctgtg    9720
ccagcccaga ggccgagagc tatggacagc attgccagta acacaggcca ccctgtgcag    9780
aagggagctg gctccagcct ggaaacctgt ctgaggttgg gagaggtgca cttggggcac    9840
agggagaggc cgggacacac ttagctggag atgtctctaa aagccctgta tcgtattcac    9900
cttcagtttt tgtgttttgg gacaattact ttagaaaata agtaggtcgt tttaaaaaca    9960
aaaattattg attgcttttt tgtagtgttc agaaaaaagg ttctttgtgt atagccaaat   10020
gactgaaagc actgatatat ttaaaaacaa aaggcaattt attaaggaaa tttgtaccat   10080
ttcagtaaac ctgtctgaat gtacctgtat acgtttcaaa aacaccccc ccccactgaa    10140 tccctgtaac ctatttatta tataaagagt ttgccttata aattt                    10185

<210> SEQ ID NO 28
<211> LENGTH: 10227
<212> TYPE: DNA
<213> ORGANISM: Homo sapiens

<400> SEQUENCE: 28
gggcgcgcgc tccctcctct cggagagagg gctgtggtaa aagccgtccg gaaaatgcgc      60
cgccgccgcc gccgcgccga gcggaggagg aggaggaggc gaggaggaga gactgctcca    120
taaaatacaa gactcaccag ttcctgcttt gatgtgacat gtgactcccc agaatacacc    180
ttgcttctgt agaccagctc caacaggatt ccatggtagc tgggatgtta gggctcaggg    240
aagaaaagtc agaagaccag gacctccagg gcctcaagga caaacccctc aagtttaaaa    300
aggtgaagaa agataagaaa gaagagaaag agggcaagca tgagcccgtg cagccatcag    360
cccaccactc tgctgagccc gcagaggcag gcaaagcaga gacatcagaa gggtcaggct    420
ccgccccggc tgtgccggaa gcttctgcct cccccaaaca gcggcgctcc atcatccgtg    480 accgggggacc catgtatgat gaccccacc tgcctgaagg ctggacacgg aagcttaagc    540
aaaggaaatc tggccgctct gctgggaagt atgatgtgta tttgatcaat ccccagggaa    600
aagcctttcg ctctaaagtg gagttgattg cgtacttcga aaaggtaggc gacacatccc    660
tggaccctaa tgattttgac ttcacggtaa ctgggagagg gagccccctcc cggcgagagc    720 agaaaccacc taagaagccc aaatctccca aagctccagg aactggcaga ggccggggac    780
gccccaaagg gagcggcacc acgagaccca aggcggccac gtcagagggt gtgcaggtga    840
aaagggtcct ggagaaaagt cctgggaagc tccttgtcaa gatgcctttt caaacttcgc    900 caggggggcaa ggctgagggg ggtggggcca ccacatccac ccaggtcatg gtgatcaaac    960
```

```
gccccggcag gaagcgaaaa gctgaggccg accctcaggc cattcccaag aaacggggcc    1020
gaaagccggg gagtgtggtg gcagccgctg ccgccgaggc caaaaagaaa gccgtgaagg    1080
agtcttctat ccgatctgtg caggagaccg tactccccat caagaagcgc aagacccggg    1140
agacggtcag catcgaggtc aaggaagtgg tgaagcccct gctggtgtcc accctcggtg    1200
agaagagcgg gaaaggactg aagacctgta gagccctggg gcggaaaagc aaggagagca    1260
gccccaaggg gcgcagcagc agcgcctcct cacccccaa gaaggagcac caccaccatc    1320
accaccactc agagtcccca aaggcccccg tgccactgct cccacccctg ccccacctc    1380
cacctgagcc cgagagctcc gaggacccca ccagcccccc tgagcccag acttgagca    1440
gcagcgtctg caaagaggag aagatgccca gaggaggctc actggagagc gacggctgcc    1500
ccaaggagcc agctaagact cagcccgcgg ttgccaccgc cgccacggcc gcagaaaagt    1560
acaaacaccg aggggaggga gagcgcaaag acattgtttc atcctccatg ccaaggccaa    1620
acagagagga gcctgtggac agccggacgc ccgtgaccga gagagttagc tgactttaca    1680
cggagcggat tgcaaagcaa accaacaaga ataaaggcag ctgttgtctc ttctccttat    1740
gggtagggct ctgacaaagc ttcccgatta actgaaataa aaatatttt tttttctttc    1800
agtaaactta gagtttcgtg gcttcagggt gggagtagtt ggagcattgg ggatgttttt    1860
cttaccgaca agcacagtca ggttgaagac ctaaccaggg ccagaagtag ctttgcactt    1920
ttctaaacta ggctccttca acaaggcttg ctgcagatac tactgaccag acaagctgtt    1980
gaccaggcac ctcccctccc gcccaaacct ttccccatg tggtcgttag agacagagcg    2040
acagagcagt tgagaggaca ctcccgtttt cggtgccatc agtgccccgt ctacagctcc    2100
cccagctccc cccacctccc ccactcccaa ccacgttggg acaggaggt gtgaggcagg    2160
agagacagtt ggattcttta gagaagatgg atatgaccag tggctatggc ctgtgcgatc    2220
ccacccgtgg tggctcaagt ctggccccac accagcccca atccaaaact ggcaaggacg    2280
cttcacagga caggaaagtg gcacctgtct gctccagctc tggcatggct aggagggggg    2340
agtcccttga actactgggt gtagactggc ctgaaccaca ggagaggatg cccagggtg    2400
aggtggcatg gtccattctc aagggacgtc ctccaacggg tggcgctaga ggccatggag    2460
gcagtaggac aaggtgcagg caggctggcc tggggtcagg ccgggcagag cacagcgggg    2520
tgagagggat tcctaatcac tcagagcagt ctgtgactta gtggacaggg gagggggcaa    2580
agggggagga gaagaaaatg ttcttccagt tactttccaa ttctccttta gggacagctt    2640
agaattattt gcactattga gtcttcatgt tcccacttca aaacaaacag atgctctgag    2700
agcaaactgg cttgaattgg tgacatttag tccctcaagc caccagatgt gacagtgttg    2760
agaactacct ggatttgtat atatacctgc gcttgttta aagtgggctc agcacatagg    2820
gttcccacga agctccgaaa ctctaagtgt ttgctgcaat tttataagga cttcctgatt    2880
ggtttctctt ctccccttcc atttctgcct tttgttcatt tcatcctttc acttctttcc    2940
cttcctccgt cctcctcctt cctagttcat cccttctctt ccaggcagcc gcggtgccca    3000
accacacttg tcggctccag tccccagaac tctgcctgcc ctttgtcctc ctgctgccag    3060
taccagcccc accctgtttt gagccctgag gaggccttgg gctctgctga gtccgacctg    3120
gcctgtctgt gaagagcaag agagcagcaa ggtcttgctc tcctaggtag ccccctcttc    3180
cctggtaaga aaaagcaaaa ggcatttccc accctgaaca acgagccttt tcacccttct    3240
actctagaga agtggactgg aggagctggg cccgatttgg tagttgagga aagcacagag    3300
```

-continued

```
gcctcctgtg gcctgccagt catcgagtgg cccaacaggg gctccatgcc agccgacctt    3360
gacctcactc agaagtccag agtctagcgt agtgcagcag ggcagtagcg gtaccaatgc    3420
agaactccca agacccgagc tgggaccagt acctgggtcc ccagcccttc ctctgctccc    3480
ccttttccct cggagttctt cttgaatggc aatgttttgc ttttgctcga tgcagacagg    3540
gggccagaac accacacatt tcactgtctg tctggtccat agctgtggtg taggggctta    3600
gaggcatggg cttgctgtgg gttttttaatt gatcagtttt catgtgggat cccatctttt    3660
taacctctgt tcaggaagtc cttatctagc tgcatatctt catcatattg gtatatcctt    3720
ttctgtgttt acagagatgt ctcttatatc taaatctgtc caactgagaa gtaccttatc    3780
aaagtagcaa atgagacagc agtcttatgc ttccagaaac acccacaggc atgtcccatg    3840
tgagctgctg ccatgaactg tcaagtgtgt gttgtcttgt gtatttcagt tattgtccct    3900
ggcttcctta ctatggtgta atcatgaagg agtgaaacat catagaaact gtctagcact    3960
tccttgccag tctttagtga tcaggaacca tagttgacag ttccaatcag tagcttaaga    4020
aaaaaccgtg tttgtctctt ctggaatggt tagaagtgag ggagtttgcc ccgttctgtt    4080
tgtagagtct catagttgga ctttctagca tatatgtgtc catttcctta tgctgtaaaa    4140
gcaagtcctg caaccaaact cccatcagcc caatccctga tccctgatcc cttccacctg    4200
ctctgctgat gaccccccca gcttcacttc tgactcttcc ccaggaaggg aaggggggtc    4260
agaagagagg gtgagtcctc cagaactctt cctccaagga cagaaggctc ctgcccccat    4320
agtggcctcg aactcctggc actaccaaag gacacttatc cacgagagcg cagcatccga    4380
ccaggttgtc actgagaaga tgtttatttt ggtcagttgg gtttttatgt attatactta    4440
gtcaaatgta atgtggcttc tggaatcatt gtccagagct gcttcccgt cacctgggcg    4500 tcatctggtc ctggtaagag gagtgcgtgg cccaccaggc cccctgtca cccatgacag    4560 ttcattcagg gccgatgggg cagtcgtggt tgggaacaca gcatttcaag cgtcacttta    4620
tttcattcgg gccccacctg cagctccctc aaagaggcag ttgcccagcc tctttccctt    4680
ccagtttatt ccagagctgc cagtgggggcc tgaggctcct tagggttttc tctctatttc    4740 ccccttttctt cctcattccc tcgtctttcc caaaggcatc acgagtcagt cgcctttcag    4800
caggcagcct tggcggttta tcgccctggc aggcaggggc cctgcagctc tcatgctgcc    4860
cctgccttgg ggtcaggttg acaggaggtt ggagggaaag ccttaagctg caggattctc    4920
accagctgtg tccggcccag ttttggggtg tgacctcaat ttcaattttg tctgtacttg    4980
aacattatga agatgggggc ctctttcagt gaatttgtga acagcagaat tgaccgacag    5040
ctttccagta cccatggggc taggtcatta aggccacatc cacagtctcc cccacccttg    5100
ttccagttgt tagttactac ctcctctcct gacaatactg tatgtcgtcg agctccccc    5160 aggtctaccc ctcccggccc tgcctgctgg tgggcttgtc atagccagtg ggattgccgg    5220
tcttgacagc tcagtgagct ggagatactt ggtcacagcc aggcgctagc acagctccct    5280
tctgttgatg ctgtattccc atatcaaaag acacagggga cacccagaaa cgccacatcc    5340
cccaatccat cagtgccaaa ctagccaacg gccccagctt ctcagctcgc tggatggcgg    5400
aagctgctac tcgtgagcgc cagtgcgggt gcagacaatc ttctgttggg tggcatcatt    5460
ccaggcccga agcatgaaca gtgcacctgg gacagggagc agcccaaat tgtcacctgc    5520 ttctctgccc agcttttcat tgctgtgaca gtgatggcga aagagggtaa taaccagaca    5580
caaactgcca agttgggtgg agaaaggagt ttctttagct gacagaatct ctgaatttta    5640
aatcacttag taagcggctc aagcccagga gggagcagag ggatacgagc ggagtcccct    5700
```

```
gcgcgggacc atctggaatt ggtttagccc aagtggagcc tgacagccag aactctgtgt    5760 ccccgtcta accacagctc cttttccaga gcattccagt caggctctct gggctgactg     5820
ggccagggga ggttacaggt accagttctt taagaagatc tttgggcata tacattttta    5880
gcctgtgtca ttgccccaaa tggattcctg tttcaagttc acacctgcag attctaggac    5940
ctgtgtccta gacttcaggg agtcagctgt ttctagagtt cctaccatgg agtgggtctg    6000
gaggacctgc ccggtggggg ggcagagccc tgctccctcc gggtcttcct actcttctct    6060
ctgctctgac gggatttgtt gattctctcc attttggtgt cttctctctt tagatattgt    6120
atcaatcttt agaaaaggca tagtctactt gttataaatc gttaggatac tgcctccccc    6180
agggtctaaa attacatatt agaggggaaa agctgaacac tgaagtcagt tctcaacaat    6240
ttagaaggaa aacctagaaa acatttggca gaaaattaca tttcgatgtt tttgaatgaa    6300
tacgagcaag cttttacaac agtgctgatc taaaaatact tagcacttgg cctgagatgc    6360
ctggtgagca ttacaggcaa ggggaatctg gaggtagccg acctgaggac atggcttctg    6420
aacctgtctt tgggagtgg tatggaaggt ggagcgttca ccagtgacct ggaaggccca     6480
gcaccaccct ccttcccact cttctcatct tgacagagcc tgccccagcg ctgacgtgtc    6540
aggaaaacac ccagggaact aggaaggcac ttctgcctga ggggcagcct gccttgccca    6600
ctcctgctct gctcgcctcg gatcagctga gccttctgag ctggcctctc actgcctccc    6660
caaggccccc tgcctgccct gtcaggaggc agaaggaagc aggtgtgagg gcagtgcaag    6720
gagggagcac aaccccagc tcccgctccg ggctccgact tgtgcacagg cagagcccag     6780
accctggagg aaatcctacc tttgaattca agaacatttg gggaatttgg aaatctcttt    6840
gcccccaaac ccccattctg tcctaccttt aatcaggtcc tgctcagcag tgagagcaga    6900
tgaggtgaaa aggccaagag gtttggctcc tgcccactga tagcccctct ccccgcagtg    6960
tttgtgtgtc aagtggcaaa gctgttcttc ctggtgaccc tgattatatc cagtaacaca    7020
tagactgtgc gcataggcct gctttgtctc ctctatcctg ggcttttgtt ttgcttttta    7080
gttttgcttt tagttttttct gtccctttta tttaacgcac cgactagaca cacaaagcag    7140 ttgaatttttt atatatatat ctgtatattg cacaattata aactcatttt gcttgtggct    7200
ccacacacac aaaaaaagac ctgttaaaat tatacctgtt gcttaattac aatatttctg    7260
ataaccatag cataggacaa gggaaaataa aaaagaaaaa aaaagaaaaa aaaacgacaa    7320
atctgtctgc tggtcacttc ttctgtccaa gcagattcgt ggtcttttcc tcgcttcttt    7380
caagggcttt cctgtgccag gtgaaggagg ctccaggcag cacccaggtt ttgcactctt    7440
gtttctcccg tgcttgtgaa agaggtccca aggttctggg tgcaggagcg ctcccttgac    7500
ctgctgaagt ccggaacgta gtcggcacag cctggtcgcc ttccacctct gggagctgga    7560
gtccactggg gtggcctgac tcccccagtc cccttcccgt gacctggtca gggtgagccc    7620
atgtggagtc agcctcgcag gcctccctgc cagtagggtc cgagtgtgtt tcatccttcc    7680
cactctgtcg agcctggggg ctggagcgga gacgggaggc ctggcctgtc tcggaacctg    7740
tgagctgcac caggtagaac gccagggacc ccagaatcat gtgcgtcagt ccaagggtc     7800 ccctccagga gtagtgaaga ctccagaaat gtcccttctt ctcccccat cctacgagta     7860 attgcatttg cttttgtaat tcttaatgag caatatctgc tagagagttt agctgtaaca    7920
gttctttttg atcatctttt tttaataatt agaaacacca aaaaaatcca gaaacttgtt    7980
cttccaaagc agagagcatt ataatcacca gggccaaaag cttccctccc tgctgtcatt    8040
```

```
gcttcttctg aggcctgaat ccaaaagaaa aacagccata ggccctttca gtggccgggc   8100
tacccgtgag cccttcggag gaccagggct ggggcagcct ctgggcccac atccggggcc   8160
agctccggcg tgtgttcagt gttagcagtg ggtcatgatg ctctttccca cccagcctgg   8220
gatagggcca gaggaggcga ggaggccgtt gccgctgatg tttggccgtg aacaggtggg   8280
tgtctgcgtg cgtccacgtg cgtgttttct gactgacatg aaatcgacgc ccgagttagc   8340
ctcacccggt gacctctagc cctgcccgga tggagcgggg cccacccggt tcagtgtttc   8400
tggggagctg gacagtggag tgcaaaaggc ttgcagaact tgaagcctgc tccttcccct   8460
gctaccacgg cctcctttcc gtttgatttg tcactgcttc aatcaataac agccgctcca   8520
gagtcagtag tcaatgaata tatgaccaaa tatcaccagg actgttactc aatgtgtgcc   8580
gagcccttgc ccatgctggg ctcccgtgta tctggacact gtaacgtgtg ctgtgtttgc   8640
tccccttccc cttccttctt tgcccttttac ttgtctttct ggggttttt c tgtttgggtt   8700
tggtttggtt tttatttctc cttttgtgtt ccaaacatga ggttctctct actggtcctc   8760
ttaactgtgg tgttgaggct tatatttgtg taattttttgg tgggtgaaag gaattttgct   8820
aagtaaatct cttctgtgtt tgaactgaag tctgtattgt aactatgttt aaagtaattg   8880
ttccagagac aaatatttct agacactttt tctttacaaa caaaagcatt cggagggagg   8940
gggatggtga ctgagatgag aggggagagc tgaacagatg accctgccc agatcagcca   9000
gaagccaccc aaagcagtgg agcccaggag tcccactcca agccagcaag ccgaatagct   9060
gatgtgttgc cactttccaa gtcactgcaa aaccaggttt tgttccgccc agtggattct   9120
tgttttgctt ccctccccc cgagattatt accaccatcc cgtgcttttta aggaaaggca   9180
agattgatgt ttccttgagg ggagccagga ggggatgtgt gtgtgcagag ctgaagagct   9240
ggggagaatg gggctgggcc cacccaagca ggaggctggg acgctctgct gtgggcacag   9300
gtcaggctaa tgttggcaga tgcagctctt cctggacagg ccaggtggtg ggcattctct   9360
ctccaaggtg tgccccgtgg gcattactgt ttaagacact tccgtcacat cccacccat    9420
cctccagggc tcaacactgt gacatctcta ttccccaccc tccccttccc agggcaataa   9480
aatgaccatg gagggggctt gcactctctt ggctgtcacc cgatcgccag caaaacttag   9540
atgtgagaaa accccttccc attccatggc gaaaacatct ccttagaaaa gccattaccc   9600
tcattaggca tggttttggg ctcccaaaac acctgacagc ccctccctcc tctgagaggc   9660
ggagagtgct gactgtagtg accattgcat gccgggtgca gcatctggaa gagctaggca   9720
gggtgtctgc ccctcctga gttgaagtca tgctcccctg tgccagccca gaggccgaga   9780
gctatggaca gcattgccag taacacaggc caccctgtgc agaagggagc tggctccagc   9840
ctggaaacct gtctgaggtt gggagaggtg cacttggggc acaggagag gccgggacac    9900
acttagctgg agatgtctct aaaagccctg tatcgtattc accttcagtt tttgtgtttt   9960
gggacaatta cttagaaaa taagtaggtc gttttaaaaa caaaaattat tgattgcttt   10020
tttgtagtgt tcagaaaaaa ggttctttgt gtatagccaa atgactgaaa gcactgatat   10080
atttaaaaac aaaaggcaat ttattaagga aatttgtacc atttcagtaa acctgtctga   10140
atgtacctgt atacgtttca aaaacacccc ccccccactg aatccctgta acctatttat   10200
tatataaaga gtttgcctta taaattt                                       10227
```

<210> SEQ ID NO 29
<211> LENGTH: 10227
<212> TYPE: DNA
<213> ORGANISM: Homo sapiens

<400> SEQUENCE: 29

```
gggcgcgcgc gctccctcct ctcggagagg gctgtggtaa aagccgtccg gaaaatggcc      60
gccgccgccg ccgccgccga gcggaggagg aggaggaggc gaggaggaga gactgctcca     120
taaaaataca gactcaccag ttcctgcttt gatgtgacat gtgactcccc agaatacacc     180
ttgcttctgt agaccagctc aacaggatt ccatggtagc tgggatgtta gggctcaggg      240
aagaaaagtc agaagaccag gacctccagg gcctcaagga caaacccctc aagtttaaaa     300
aggtgaagaa agataagaaa gaagagaaag agggcaagca tgagcccgtg cagccatcag     360
cccaccactc tgctgagccc gcagaggcag gcaaagcaga gacatcagaa gggtcaggct     420
ccgcccggc tgtgccggaa gcttctgcct ccccaaaca gcggcgctcc atcatccgtg       480
accggggacc catgtatgat gaccccaccc tgcctgaagg ctggacacgg aagcttaagc     540
aaaggaaatc tggccgctct gctgggaagt atgatgtgta tttgatcaat ccccagggaa     600
aagcctttcg ctctaaagtg gagttgattg cgtacttcga aaaggtaggc gacacatccc     660
tggaccctaa tgattttgac ttcacggtaa ctgggagagg gagcccctcc cggcgagagc     720
agaaaccacc taagaagccc aaatctccca agctccagg aactggcaga ggccggggac     780
gccccaaagg gagcggcacc acgagaccca aggcggccac gtcagagggt gtgcaggtga     840
aaagggtcct ggagaaaagt cctgggaagc tccttgtcaa gatgcctttt caaacttcgc     900
caggggcaa ggctgagggg ggtggggcca ccacatccac ccaggtcatg gtgatcaaac      960
gccccggcag gaagcgaaaa gctgaggccg accctcaggc cattcccaag aaacggggcc    1020
gaaagccggg gagtgtggtg gcagccgctg ccgccgaggc caaaaagaaa gccgtgaagg    1080
agtcttctat ccgatctgtg caggagaccg tactccccat caagaagcgc aagacccggg    1140
agacggtcag catcgaggtc aaggaagtgg tgaagcccct gctggtgtcc accctcggtg    1200
agaagagcgg gaaaggactg aagacctgta agagccctgg gcggaaaagc aaggagagca    1260
gccccaaggg gcgcagcagc agcgcctcct caccccccaa gaaggagcac caccaccatc    1320
accaccactc agagtcccca aaggccccg tgccactgct cccaccctg cccccaccctc     1380
cacctgagcc cgagagctcc gaggacccca ccagcccccc tgagcccag gacttgagca    1440
gcagcgtctg caaagaggag aagatgccca gaggaggctc actggagagc gacggctgcc    1500
ccaaggagcc agctaagact cagcccgcgg ttgccaccgc cgccacggcc gcagaaaagt    1560
acaaacaccg aggggaggga gagcgcaaag acattgtttc atcctccatg ccaaggccaa    1620
acagagagga gcctgtggac agccggacgc ccgtgaccga gagagttagc tgactttaca    1680
cggagcggat tgcaaagcaa accaacaaga ataaaggcag ctgttgtctc ttctccttat    1740
gggtagggct ctgacaaagc ttcccgatta actgaaataa aaatatttt tttttctttc     1800
agtaaactta gagtttcgtg gcttcagggt gggagtagtt ggagcattgg ggatgttttt    1860
cttaccgaca agcacagtca ggttgaagac ctaaccaggg ccagaagtag ctttgcactt    1920
ttctaaacta ggctccttca acaaggcttg ctgcagatac tactgaccag acaagctgtt    1980
gaccaggcac ctcccctccc gcccaaacct ttccccatg tggtcgttag agacagagcg     2040
acagagcagt tgagaggaca ctcccgtttt cggtgccatc agtgcccgt ctacagctcc     2100
cccagctccc cccacctccc ccactcccaa ccacgttggg acagggaggt gtgaggcagg    2160
agagacagtt ggattcttta gagaagatgg atatgaccag tggctatggc ctgtgcgatc    2220
ccacccgtgg tggctcaagt ctggccccac accagcccca atccaaaact ggcaaggacg    2280
```

```
cttcacagga caggaaagtg gcacctgtct gctccagctc tggcatggct aggaggggggg    2340 agtcccttga actactgggt gtagactggc ctgaaccaca ggagaggatg gcccagggtg    2400
aggtggcatg gtccattctc aagggacgtc ctccaacggg tggcgctaga ggccatggag    2460
gcagtaggac aaggtgcagg caggctggcc tggggtcagg ccgggcagag cacagcgggg    2520
tgagagggat tcctaatcac tcagagcagt ctgtgactta gtggacaggg gaggggcaa     2580 aggggggagga gaagaaaatg ttcttccagt tactttccaa ttctcctta gggacagctt    2640 agaattattt gcactattga gtcttcatgt tcccacttca aaacaaacag atgctctgag    2700
agcaaactgg cttgaattgg tgacatttag tccctcaagc caccagatgt gacagtgttg    2760
agaactacct ggatttgtat atatacctgc gcttgtttta aagtgggctc agcacatagg    2820
gttcccacga agctccgaaa ctctaagtgt ttgctgcaat tttataagga cttcctgatt    2880
ggtttctctt ctccccttcc atttctgcct tttgttcatt tcatcctttc acttctttcc    2940
cttcctccgt cctcctcctt cctagttcat cccttctctt ccaggcagcc gcggtgccca    3000
accacacttg tcggctccag tccccagaac tctgcctgcc ctttgtcctc ctgctgccag    3060
taccagcccc accctgtttt gagccctgag gaggccttgg gctctgctga gtccgacctg    3120
gcctgtctgt gaagagcaag agagcagcaa ggtcttgctc tcctaggtag ccccctcttc    3180
cctggtaaga aaaagcaaaa ggcatttccc accctgaaca acgagccttt tcacccttct    3240
actctagaga agtggactgg aggagctggg cccgatttgg tagttgagga aagcacagag    3300
gcctcctgtg gcctgccagt catcgagtgg cccaacaggg gctccatgcc agccgacctt    3360
gacctcactc agaagtccag agtctagcgt agtgcagcag ggcagtagcg gtaccaatgc    3420
agaactccca agacccgagc tgggaccagt acctgggtcc ccagcccttc ctctgctccc    3480
ccttttccct cggagttctt cttgaatggc aatgttttgc ttttgctcga tgcagacagg    3540
gggccagaac accacacatt tcactgtctg tctggtccat agctgtggtg taggggctta    3600
gaggcatggg cttgctgtgg gttttttaatt gatcagtttt catgtgggat cccatctttt    3660
taacctctgt tcaggaagtc cttatctagc tgcatatctt catcatattg gtatatcctt    3720
ttctgtgttt acagagatgt ctcttatatc taaatctgtc caactgagaa gtaccttatc    3780
aaagtagcaa atgagacagc agtcttatgc ttccagaaac acccacaggc atgtcccatg    3840
tgagctgctg ccatgaactg tcaagtgtgt gttgtcttgt gtatttcagt tattgtccct    3900
ggcttcctta ctatggtgta atcatgaagg agtgaaacat catagaaact gtctagcact    3960
tccttgccag tctttagtga tcaggaacca tagttgacag ttccaatcag tagcttaaga    4020
aaaaaccgtg tttgtctctt ctggaatggt tagaagtgag ggagtttgcc ccgttctgtt    4080
tgtagagtct catagttgga cttctagca tatatgtgtc catttcctta tgctgtaaaa     4140
gcaagtcctg caaccaaact cccatcagcc caatccctga tccctgatcc cttccacctg    4200
ctctgctgat gacccccca gcttcacttc tgactcttcc ccaggaaggg aagggggggtc    4260 agaagagagg gtgagtcctc cagaactctt cctccaagga cagaaggctc ctgcccccat    4320
agtggcctcg aactcctggc actaccaaag gacacttatc cacgagagcg cagcatccga    4380
ccaggttgtc actgagaaga tgtttatttt ggtcagttgg ggtttttatgt attatactta    4440 gtcaaatgta atgtggcttc tggaatcatt gtccagagct gcttcccccgt cacctgggcg    4500 tcatctggtc ctggtaagag gagtgcgtgg cccaccaggc cccctgtca cccatgacag    4560 ttcattcagg gccgatgggg cagtcgtggt tgggaacaca gcatttcaag cgtcacttta    4620
tttcattcgg gccccacctg cagctccctc aaagaggcag ttgcccagcc tctttccctt    4680
```

```
ccagtttatt ccagagctgc cagtggggcc tgaggctcct tagggttttc tctctatttc    4740
cccctttctt cctcattccc tcgtctttcc caaaggcatc acgagtcagt cgcctttcag    4800
caggcagcct tggcggttta tcgccctggc aggcaggggc cctgcagctc tcatgctgcc    4860
cctgccttgg ggtcaggttg acaggaggtt ggagggaaag ccttaagctg caggattctc    4920
accagctgtg tccggcccag ttttggggtg tgacctcaat ttcaattttg tctgtacttg    4980
aacattatga agatgggggc ctctttcagt gaatttgtga acagcagaat tgaccgacag    5040 cttttccagta cccatgggc taggtcatta aggccacatc cacagtctcc cccacccttg    5100
ttccagttgt tagttactac ctcctctcct gacaatactg tatgtcgtcg agctcccccc    5160
aggtctaccc ctcccggccc tgcctgctgg tgggcttgtc atagccagtg ggattgccgg    5220
tcttgacagc tcagtgagct ggagatactt ggtcacagcc aggcgctagc acagctccct    5280
tctgttgatg ctgtattccc atatcaaaag acacagggga cacccagaaa cgccacatcc    5340
cccaatccat cagtgccaaa ctagccaacg gccccagctt ctcagctcgc tggatggcgg    5400
aagctgctac tcgtgagcgc cagtgcgggt gcagacaatc ttctgttggg tggcatcatt    5460
ccaggcccga agcatgaaca gtgcacctgg gacagggagc agccccaaat tgtcacctgc    5520
ttctctgccc agcttttcat tgctgtgaca gtgatggcga agagggtaa taaccagaca    5580 caaactgcca agttgggtgg agaaaggagt ttctttagct gacagaatct ctgaattta    5640 aatcacttag taagcggctc aagcccagga gggagcagag ggatacgagc ggagtcccct    5700
gcgcgggacc atctggaatt ggtttagccc aagtggagcc tgacagccag aactctgtgt    5760
cccccgtcta accacagctc cttttccaga gcattccagt caggctctct gggctgactg    5820
ggccagggga ggttacaggt accagttctt taagaagatc tttgggcata cattttta    5880 gcctgtgtca ttgccccaaa tggattcctg tttcaagttc acacctgcag attctaggac    5940
ctgtgtccta gacttcaggg agtcagctgt ttctagagtt cctaccatgg agtgggtctg    6000
gaggacctgc ccggtggggg ggcagagccc tgctccctcc gggtcttcct actcttctct    6060
ctgctctgac gggatttgtt gattctctcc attttggtgt ctttctcttt tagatattgt    6120
atcaatcttt agaaaaggca tagtctactt gttataaatc gttaggatac tgcctccccc    6180
agggtctaaa attacatatt agaggggaaa agctgaacac tgaagtcagt tctcaacaat    6240
ttagaaggaa aacctagaaa acatttggca gaaaattaca tttcgatgtt tttgaatgaa    6300
tacgagcaag cttttacaac agtgctgatc taaaaatact tagcacttgg cctgagatgc    6360
ctggtgagca ttacaggcaa ggggaatctg gaggtagccg acctgaggac atggcttctg    6420
aacctgtctt tgggagtgg tatggaaggt ggagcgttca ccagtgacct ggaaggccca    6480
gcaccaccct ccttcccact cttctcatct tgacagagcc tgccccagcg ctgacgtgtc    6540
aggaaaacac ccagggaact aggaaggcac ttctgcctga ggggcagcct gccttgccca    6600
ctcctgctct gctcgcctcg gatcagctga gccttctgag ctggcctctc actgcctccc    6660
caaggccccc tgcctgccct gtcaggaggc agaaggaagc aggtgtgagg gcagtgcaag    6720
gagggagcac aaccccagc tcccgctccg ggctccgact tgtgcacagg cagagcccag    6780
accctggagg aaatcctacc tttgaattca agaacatttg gggaatttgg aaatctcttt    6840
gcccccaaac ccccattctg tcctaccttt aatcaggtcc tgctcagcag tgagagcaga    6900
tgaggtgaaa aggccaagag gtttggctcc tgcccactga tagcccctct ccccgcagtg    6960
tttgtgtgtc aagtggcaaa gctgttcttc ctggtgaccc tgattatatc cagtaacaca    7020
```

```
tagactgtgc gcataggcct gctttgtctc ctctatcctg ggcttttgtt ttgcttttta    7080
gttttgcttt tagtttttct gtccctttta tttaacgcac cgactagaca cacaaagcag    7140 ttgaatttt atatatatat ctgtatattg cacaattata aactcatttt gcttgtggct    7200
ccacacacac aaaaaaagac ctgttaaaat tatacctgtt gcttaattac aatatttctg    7260
ataaccatag cataggacaa gggaaaataa aaaagaaaa aaaagaaaaa aaacgacaa     7320 atctgtctgc tggtcacttc ttctgtccaa gcagattcgt ggtctttcc tcgcttcttt    7380 caagggcttt cctgtgccag gtgaaggagg ctccaggcag cacccaggtt ttgcactctt    7440
gtttctcccg tgcttgtgaa agaggtccca aggttctggg tgcaggagcg ctcccttgac    7500
ctgctgaagt ccggaacgta gtcggcacag cctggtcgcc ttccacctct gggagctgga    7560
gtccactggg gtggcctgac tcccccagtc cccttcccgt gacctggtca gggtgagccc    7620
atgtggagtc agcctcgcag gcctccctgc cagtagggtc cgagtgtgtt tcatccttcc    7680
cactctgtcg agcctggggg ctggagcgga gacgggaggc ctggcctgtc tcggaacctg    7740
tgagctgcac caggtagaac gccagggacc ccagaatcat gtgcgtcagt ccaaggggtc    7800
ccctccagga gtagtgaaga ctccagaaat gtccctttct tctcccccat cctacgagta    7860
attgcatttg cttttgtaat tcttaatgag caatatctgc tagagagttt agctgtaaca    7920 gttcttttg atcatctttt tttaataatt agaaacacca aaaaaatcca gaaacttgtt    7980
cttccaaagc agagagcatt ataatcacca gggccaaaag cttccctccc tgctgtcatt    8040
gcttcttctg aggcctgaat ccaaaagaaa aacagccata gcccctttca gtggccgggc    8100
tacccgtgag cccttcggag gaccagggct ggggcagcct ctgggcccac atccggggcc    8160
agctccggcg tgtgttcagt gttagcagtg ggtcatgatg ctctttccca cccagcctgg    8220
gataggggca gaggaggcga ggaggccgtt gccgctgatg tttggccgtg aacaggtggg    8280
tgtctgcgtg cgtccacgtg cgtgtttct gactgacatg aaatcgacgc ccagagttagc    8340 ctcacccggt gacctctagc cctgcccgga tggagcgggg cccacccggt tcagtgtttc    8400
tggggagctg gacagtggag tgcaaaaggc ttgcagaact tgaagcctgc tccttccctt    8460
gctaccacgg cctcctttcc gtttgatttg tcactgcttc aatcaataac agccgctcca    8520
gagtcagtag tcaatgaata tatgaccaaa tatcaccagg actgttactc aatgtgtgcc    8580
gagcccttgc ccatgctggg ctcccgtgta tctggacact gtaacgtgtg ctgtgtttgc    8640
tccccttccc cttccttctt tgcccttttac ttgtctttct ggggttttc tgtttgggtt    8700 tggtttggtt tttatttctc cttttgtgtt ccaaacatga ggttctctct actggtcctc    8760
ttaactgtgg tgttgaggct tatatttgtg taattttgg tgggtgaaag gaattttgct     8820
aagtaaatct cttctgtgtt tgaactgaag tctgtattgt aactatgttt aaagtaattg    8880
ttccagagac aaatatttct agacactttt tctttacaaa caaaagcatt cggagggagg    8940
gggatggtga ctgagatgag aggggagagc tgaacagatg ccctgccc agatcagcca     9000 gaagccaccc aaagcagtgg agcccaggag tcccactcca agccagcaag ccgaatagct    9060
gatgtgttgc cactttccaa gtcactgcaa aaccaggttt gttccgccc agtggattct     9120 tgttttgctt cccctccccc cgagattatt accaccatcc cgtgctttta aggaaaggca    9180
agattgatgt tccttgagg ggagccagga ggggatgtgt gtgtgcagag ctgaagagct     9240 gggggagaatg gggctgggcc cacccaagca ggaggctggg acgctctgct gtgggcacag    9300
gtcaggctaa tgttggcaga tgcagctctt cctggacagg ccaggtggtg ggcattctct    9360
ctccaaggtg tgccccgtgg gcattactgt ttaagacact tccgtcacat cccaccccat    9420
```

```
cctccagggc tcaacactgt gacatctcta ttccccaccc tcccctteec agggcaataa    9480 aatgaccatg gagggggctt gcactctctt ggctgtcacc cgatcgccag caaaacttag    9540
atgtgagaaa accccttccc attccatggc gaaaacatct ccttagaaaa gccattaccc    9600
tcattaggca tggttttggg ctcccaaaac acctgacagc ccctccctcc tctgagaggc    9660
ggagagtgct gactgtagtg accattgcat gccgggtgca gcatctggaa gagctaggca    9720
gggtgtctgc cccctcctga gttgaagtca tgctcccctg tgccagccca gaggccgaga    9780
gctatggaca gcattgccag taacacaggc caccctgtgc agaagggagc tggctccagc    9840
ctggaaacct gtctgaggtt gggagaggtg cacttggggc acagggagag gccgggacac    9900
acttagctgg agatgtctct aaaagccctg tatcgtattc accttcagtt tttgtgtttt    9960
gggacaatta ctttagaaaa taagtaggtc gttttaaaaa caaaaattat tgattgcttt   10020
tttgtagtgt tcagaaaaaa ggttctttgt gtatagccaa atgactgaaa gcactgatat   10080
atttaaaaac aaaaggcaat ttattaagga aatttgtacc atttcagtaa acctgtctga   10140
atgtacctgt atacgtttca aaaacacccc cccccactg aatccctgta acctatttat   10200
tatataaaga gtttgcctta taaattt                                       10227
```